(12) United States Patent
Basude et al.

(10) Patent No.: US 11,723,769 B2
(45) Date of Patent: Aug. 15, 2023

(54) TISSUE GRASPING DEVICES AND RELATED METHODS

(71) Applicant: MEDFREE, INC., Fremont, CA (US)

(72) Inventors: Raghuveer Basude, Fremont, CA (US); Shri Krishna Basude, Fremont, CA (US)

(73) Assignee: MedFree, Inc., Newark, CA (US)

( * ) Notice: Subject to any disclaimer, the term of this patent is extended or adjusted under 35 U.S.C. 154(b) by 323 days.

(21) Appl. No.: 16/905,788

(22) Filed: Jun. 18, 2020

(65) Prior Publication Data

US 2020/0383782 A1 Dec. 10, 2020

Related U.S. Application Data

(63) Continuation of application No. PCT/US2019/013853, filed on Jan. 16, 2019.

(Continued)

(51) Int. Cl.
*A61F 2/24* (2006.01)
*A61B 17/00* (2006.01)
(Continued)

(52) U.S. Cl.
CPC .......... *A61F 2/2439* (2013.01); *A61F 2/246* (2013.01); *A61B 17/0401* (2013.01);
(Continued)

(58) Field of Classification Search
CPC ...... A61F 2/2439; A61F 2/246; A61F 2/2454; A61F 2/2466; A61F 2/2427; A61F 2/243;
(Continued)

(56) References Cited

U.S. PATENT DOCUMENTS 3,671,979 A 6/1972 Moulopoulos et al.
3,874,338 A 4/1975 Happel
(Continued)

FOREIGN PATENT DOCUMENTS

CN 106420113 A 2/2017
JP 2006528911 A 12/2006
(Continued)

OTHER PUBLICATIONS

Co-pending U.S. Appl. No. 17/497,373, inventor Basude; Raghuveer, filed Oct. 8, 2021.
(Continued)

*Primary Examiner* — Timothy J Neal
*Assistant Examiner* — Mitchell Brian Hoag
(74) *Attorney, Agent, or Firm* — Wilson Sonsini Goodrich & Rosati

(57) ABSTRACT

A clip for immobilizing leaflets of a cardiac or venous valve includes a hub having a pair of tangle resistant spring-biased outer arms coupled to an inferior end of the hub and a pair of tangle resistant spring-biased inner arms adjacent to the outer arms and coupled to a superior end of the hub. A delivery catheter may be used to position the valve clip adjacent a target valve while the outer and inner arms are biased in an opened position relative to each other. After the valve leaflets are located between the opened outer and inner arms, the biasing forces may be released to allow the clip to self-close the clip over the valve leaflets.

20 Claims, 61 Drawing Sheets

Related U.S. Application Data

(60) Provisional application No. 62/617,946, filed on Jan. 16, 2018.

(51) Int. Cl.
*A61B 17/04* (2006.01)
*A61B 17/122* (2006.01)
*A61B 17/128* (2006.01)

(52) U.S. Cl.
CPC ....... *A61B 17/1227* (2013.01); *A61B 17/1285* (2013.01); *A61B 2017/00243* (2013.01); *A61B 2017/0427* (2013.01); *A61B 2017/0464* (2013.01); *A61F 2/243* (2013.01); *A61F 2/2427* (2013.01); *A61F 2/2454* (2013.01); *A61F 2/2466* (2013.01)

(58) Field of Classification Search
CPC ............ A61B 17/0401; A61B 17/1285; A61B 2017/00243; A61B 2017/0427; A61B 2017/0464; A61B 17/1227
See application file for complete search history.

(56) References Cited

U.S. PATENT DOCUMENTS

| | | | |
|---|---|---|---|
| 4,056,854 A | 11/1977 | Boretos et al. | |
| 4,484,579 A | 11/1984 | Meno et al. | |
| 4,917,089 A | 4/1990 | Sideris | |
| 4,994,077 A | 2/1991 | Dobben | |
| 5,332,402 A | 7/1994 | Teitelbaum | |
| 5,411,552 A | 5/1995 | Andersen et al. | |
| 5,478,344 A | 12/1995 | Stone et al. | |
| 5,554,185 A | 9/1996 | Block et al. | |
| 5,718,725 A | 2/1998 | Sterman et al. | |
| 5,769,812 A | 6/1998 | Stevens et al. | |
| 5,797,960 A | 8/1998 | Stevens et al. | |
| 5,823,956 A | 10/1998 | Roth et al. | |
| 5,829,447 A | 11/1998 | Stevens et al. | |
| 5,840,081 A | 11/1998 | Andersen et al. | |
| 5,855,614 A | 1/1999 | Stevens et al. | |
| 6,117,144 A | 9/2000 | Nobles et al. | |
| 6,269,819 B1 | 8/2001 | Oz et al. | |
| 6,461,366 B1 | 10/2002 | Seguin | |
| 6,629,534 B1 | 10/2003 | St. et al. | |
| 6,752,813 B2 | 6/2004 | Goldfarb et al. | |
| 7,226,467 B2 | 6/2007 | Lucatero et al. | |
| 7,316,706 B2 | 1/2008 | Bloom et al. | |
| 7,449,024 B2 | 11/2008 | Stafford | |
| 7,464,712 B2 | 12/2008 | Oz et al. | |
| 7,509,959 B2 | 3/2009 | Oz et al. | |
| 7,563,267 B2 | 7/2009 | Goldfarb et al. | |
| 7,563,273 B2 | 7/2009 | Goldfarb et al. | |
| 7,604,646 B2 | 10/2009 | Goldfarb et al. | |
| 7,608,091 B2 | 10/2009 | St. et al. | |
| 7,635,329 B2 | 12/2009 | Goldfarb et al. | |
| 7,655,015 B2 | 2/2010 | Goldfarb et al. | |
| 7,666,204 B2 | 2/2010 | Thornton et al. | |
| 7,682,319 B2 | 3/2010 | Martin et al. | |
| 7,704,269 B2 | 4/2010 | St. et al. | |
| 7,736,388 B2 | 6/2010 | Goldfarb et al. | |
| 7,758,596 B2 | 7/2010 | Oz et al. | |
| 7,811,296 B2 | 10/2010 | Goldfarb et al. | |
| 7,938,827 B2 | 5/2011 | Hauck et al. | |
| 7,981,139 B2 | 7/2011 | Martin et al. | |
| 7,998,151 B2 | 8/2011 | St. et al. | |
| 8,029,518 B2 | 10/2011 | Goldfarb et al. | |
| 8,052,592 B2 | 11/2011 | Goldfarb et al. | |
| 8,057,493 B2 | 11/2011 | Goldfarb et al. | |
| 8,123,703 B2 | 2/2012 | Martin et al. | |
| 8,133,239 B2 | 3/2012 | Oz et al. | |
| 8,187,299 B2 | 5/2012 | St. et al. | |
| 8,216,230 B2 | 7/2012 | Hauck et al. | |
| 8,216,256 B2 | 7/2012 | Raschdorf, Jr. et al. | |
| 8,303,608 B2 | 11/2012 | Goldfarb et al. | |
| 8,323,334 B2 | 12/2012 | Deem et al. | |
| 8,343,174 B2 | 1/2013 | Goldfarb et al. | |
| 8,409,273 B2 | 4/2013 | Thornton et al. | |
| 8,470,028 B2 | 6/2013 | Thornton et al. | |
| 8,721,665 B2 | 5/2014 | Oz et al. | |
| 8,734,505 B2 | 5/2014 | St. et al. | |
| 8,740,918 B2 | 6/2014 | Seguin | |
| 8,740,920 B2 | 6/2014 | Goldfarb et al. | |
| 10,137,019 B2 * | 11/2018 | Berreklouw ............ A61F 2/962 |
| 10,159,570 B1 | 12/2018 | Metchik et al. | |
| 2004/0049207 A1 | 3/2004 | Goldfarb et al. | |
| 2008/0167750 A1 | 7/2008 | Stahler et al. | |
| 2008/0221672 A1 * | 9/2008 | Lamphere ............ A61F 2/2439 |
| | | | 623/2.12 |
| 2009/0054902 A1 | 2/2009 | Mickiewicz et al. | |
| 2012/0022633 A1 * | 1/2012 | Olson .................... A61F 2/2439 |
| | | | 623/2.11 |
| 2012/0065464 A1 | 3/2012 | Ellis et al. | |
| 2013/0066341 A1 | 3/2013 | Ketai et al. | |
| 2013/0150710 A1 | 6/2013 | Zentgraf et al. | |
| 2013/0282059 A1 | 10/2013 | Ketai et al. | |
| 2013/0338764 A1 | 12/2013 | Thornton et al. | |
| 2014/0236187 A1 | 8/2014 | Seguin et al. | |
| 2014/0236198 A1 | 8/2014 | Goldfarb et al. | |
| 2015/0182223 A1 * | 7/2015 | Ketai ..................... A61B 17/10 |
| | | | 606/151 |
| 2015/0223793 A1 | 8/2015 | Goldfarb et al. | |
| 2015/0257877 A1 | 9/2015 | Hernandez | |
| 2015/0257883 A1 | 9/2015 | Basude et al. | |
| 2016/0143731 A1 * | 5/2016 | Backus .................. A61F 2/243 |
| | | | 623/2.17 |
| 2016/0157862 A1 * | 6/2016 | Hernandez ......... A61B 17/1285 |
| | | | 606/151 |
| 2016/0338716 A1 * | 11/2016 | Aslinia .................. A61B 10/04 |
| 2017/0020521 A1 * | 1/2017 | Krone ..................... A61F 2/246 |
| 2017/0333187 A1 * | 11/2017 | Hariton ................... A61F 2/243 |
| 2018/0146964 A1 * | 5/2018 | Garcia .............. A61B 17/1285 |
| 2018/0296325 A1 * | 10/2018 | McLean ................ A61F 2/2436 |
| 2018/0296334 A1 * | 10/2018 | Dixon ..................... A61F 2/246 |
| 2018/0325661 A1 * | 11/2018 | Delgado ............ A61B 17/1285 |
| 2019/0030285 A1 | 1/2019 | Prabhu et al. | |
| 2019/0142589 A1 | 5/2019 | Raghuveer | |
| 2020/0138578 A1 * | 5/2020 | Thornton ............... A61F 2/2466 |
| 2020/0229806 A1 | 7/2020 | Goldfarb et al. | |

FOREIGN PATENT DOCUMENTS

| | | |
|---|---|---|
| WO | WO-9101689 A1 | 2/1991 |
| WO | WO-9835638 A1 | 8/1998 |
| WO | WO-9900059 A1 | 1/1999 |
| WO | WO-9901377 A1 | 1/1999 |
| WO | WO-0003759 A3 | 4/2000 |
| WO | WO-0060995 A2 | 10/2000 |
| WO | WO-0060995 A3 | 4/2001 |
| WO | WO-2004103162 A3 | 8/2005 |
| WO | WO-2014136056 A1 | 9/2014 |
| WO | WO-2016133950 A1 | 8/2016 |
| WO | WO-2017015288 A2 | 1/2017 |
| WO | WO-2018013856 A1 * | 1/2018 ........... A61B 17/122 |
| WO | WO-2019010370 A1 | 1/2019 |
| WO | WO-2019143726 A1 | 7/2019 |

OTHER PUBLICATIONS

EP17828492.3 Extended European Search Report dated Jun. 24, 2020.
EP19741513.6 Extended Search Report dated Sep. 23, 2021.
Office action dated Jan. 12, 2021 for U.S. Appl. No. 16/246,866.
PCT/US2017/042003 International Search Report and Written Opinion dated Sep. 29, 2017.
U.S. Appl. No. 16/246,866 Notice of Allowance dated Jul. 21, 2021.
Abe, et al. De Vega's annuloplasty for acquired tricuspid disease: Early and late results in 110 patients. The Annals of thoracic surgery 48.5 (1989): 670-676.
Alvarez, et al. Repairing the degenerative mitral valve: ten-to fifteen-year follow-up. The Journal of Thoracic and Cardiovascular Surgery112.2 (1996): 238-247.

(56) References Cited

OTHER PUBLICATIONS

Bach, et al. Early improvement in congestive heart failure after correction of secondary mitral regurgitation in end-stage cardiomyopathy. American heart journal129.6 (1995): 1165-1170.

Bach, et al. Improvement following correction of secondary mitral regurgitation in end-stage cardiomyopathy with mitral annuloplasty. The American journal of cardiology 78.8 (1996): 966-969.

Bolling, et al. Early outcome of mitral valve reconstruction in patients with end-stage cardiomyopathy. The Journal of thoracic and cardiovascular surgery 109.4 (1995): 676-683.

Cosgrove, et al. Tricuspid valve repair with the Cosgrove-Edwards annuloplasty system. The Annals of thoracic surgery 64.1 (1997): 267-268.

Dec, et al. Idiopathic dilated cardiomyopathy. New England Journal of Medicine 331.23 (1994): 1564-1575.

Fucci, et al. Improved results with mitral valve repair using new surgical techniques. European journal of cardio-thoracic surgery 9.11 (1995): 621-627.

International Search Report and Written Opinion for PCT/US2019/013853 dated Apr. 11, 2019.

Kameda, et al. Annuloplasty for severe mitral regurgitation due to dilated cardiomyopathy. The Annals of thoracic surgery 61.6 (1996): 1829-1832.

Khan, et al. Blade atrial septostomy: experience with the first 50 procedures. Catheterization and cardiovascular diagnosis 23.4 (1991): 257-262.

Maisano, et al. The edge-to-edge technique: a simplified method to correct mitral insufficiency. European Journal of Cardio-thoracic Surgery 13.3 (1998): 240-246.

Meritmedical. HeartSpan® Steerable Sheath Introducer, https://www.merit.com/cardiac-intervention/ep-and-crm/electrophysiology/heartspan-steerable-sheath-introducer/. Downloaded Apr. 29, 2019. 5 pages.

Park, et al. Clinical use of blade atrial septostomy. Circulation 58.4 (1978): 600-606.

Ricchi, et al. Linear segmental annuloplasty for mitral valve repair. The Annals of thoracic surgery 63.6 (1997): 1805-1806.

Tager, et al. Long-term follow-up of rheumatic patients undergoing left-sided valve replacement with tricuspid annuloplasty—validity of preoperative echocardiographic criteria in the decision to perform tricuspid annuloplasty. The American journal of cardiology 81.8 (1998): 1013-1016.

Uchida, et al. Percutaneous cardiomyotomy and valvulotomy with angioscopic guidance. American heart journal 121.4 (1991): 1221-1224.

Umana, et al. "Bow-tie" mitral valve repair: an adjuvant technique for ischemic mitral regurgitation. The Annals of Thoracic Surgery 66.5 (1998): 1640-1645.

* cited by examiner

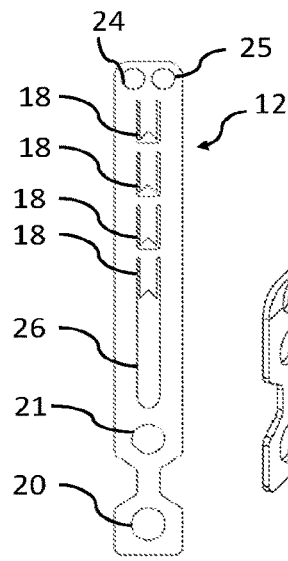
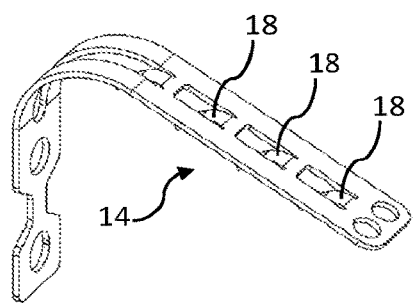
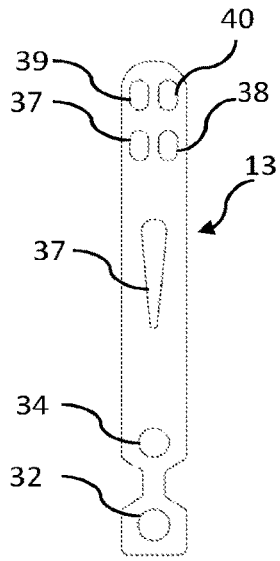
FIG. 14  FIG. 15  FIG. 16  FIG. 17
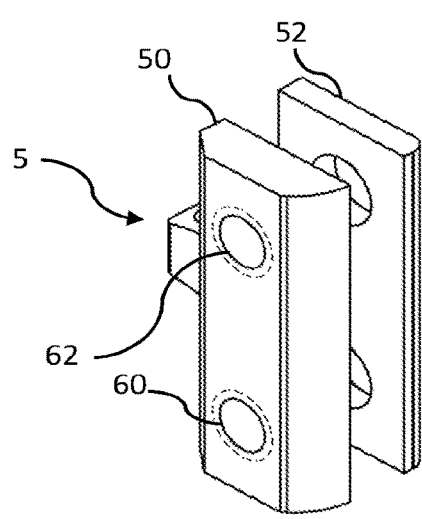
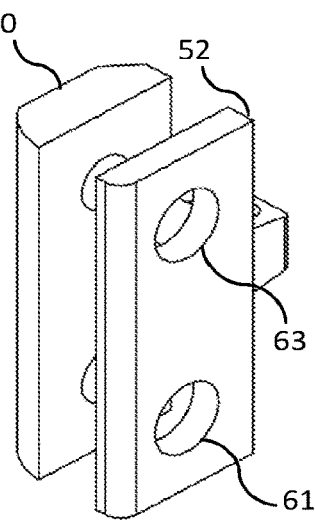
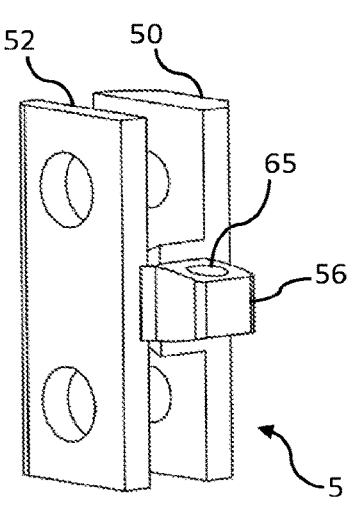
FIG. 18  FIG. 19  FIG. 20

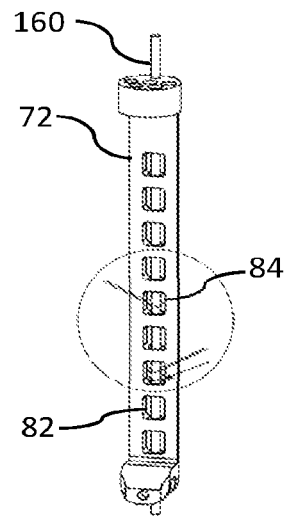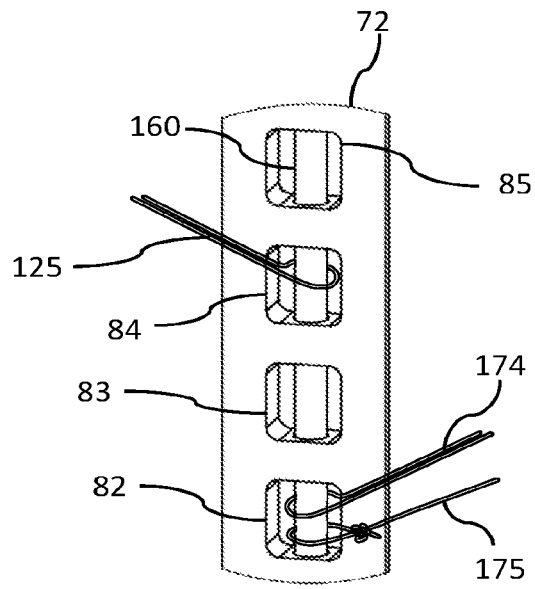
FIG. 44                FIG. 45
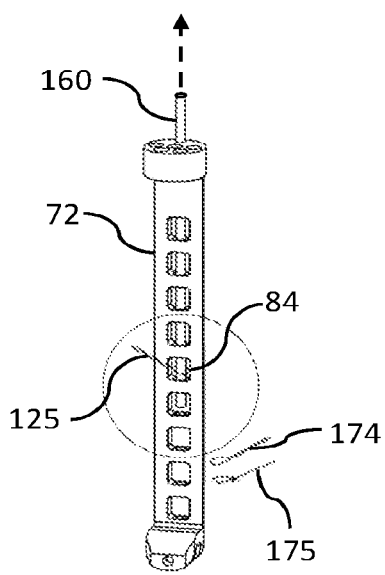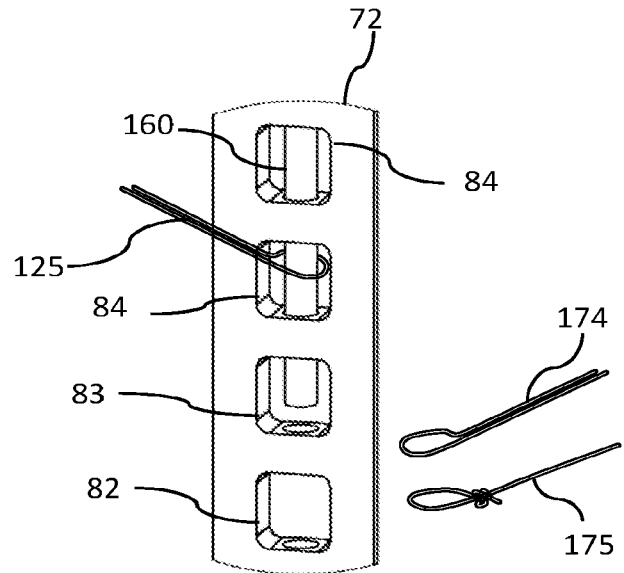
FIG. 46                FIG. 47

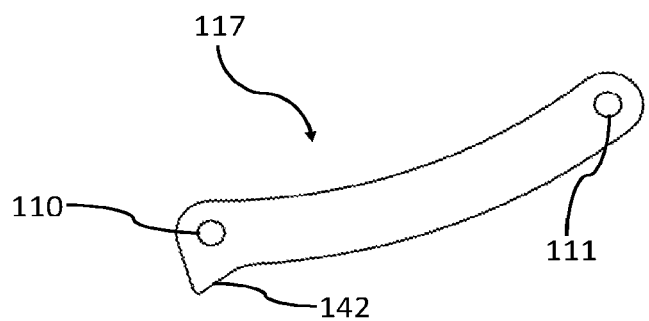
FIG. 48
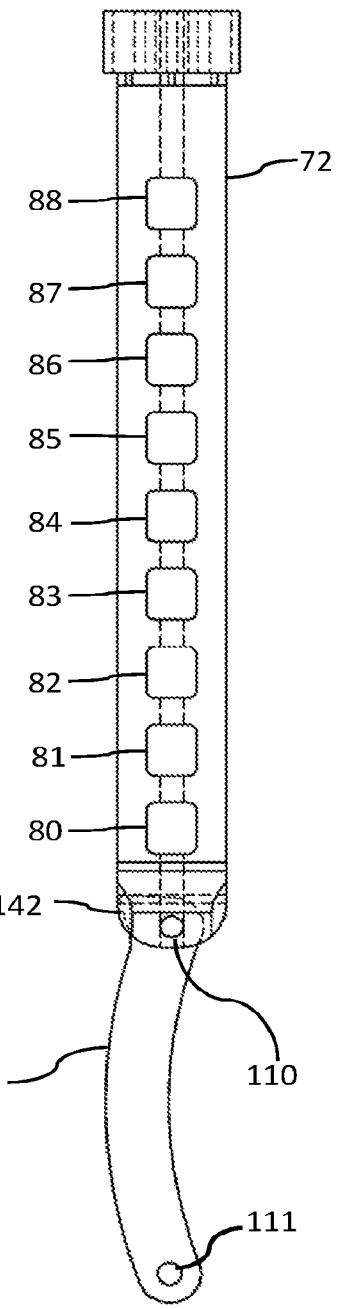
FIG. 49
FIG. 50

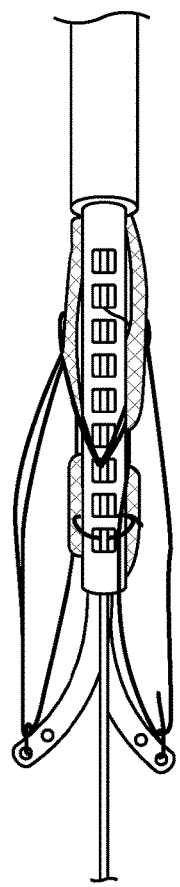 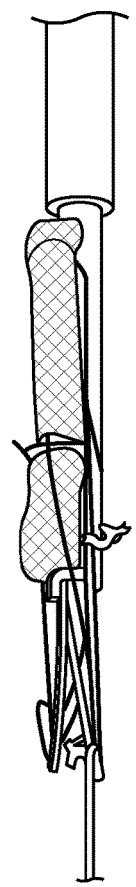
FIG. 58  FIG. 59
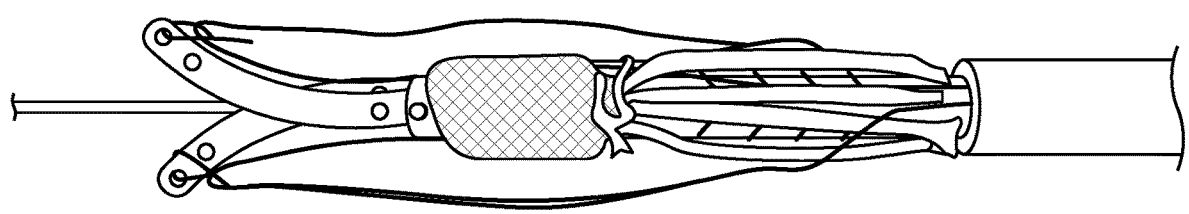
FIG. 60

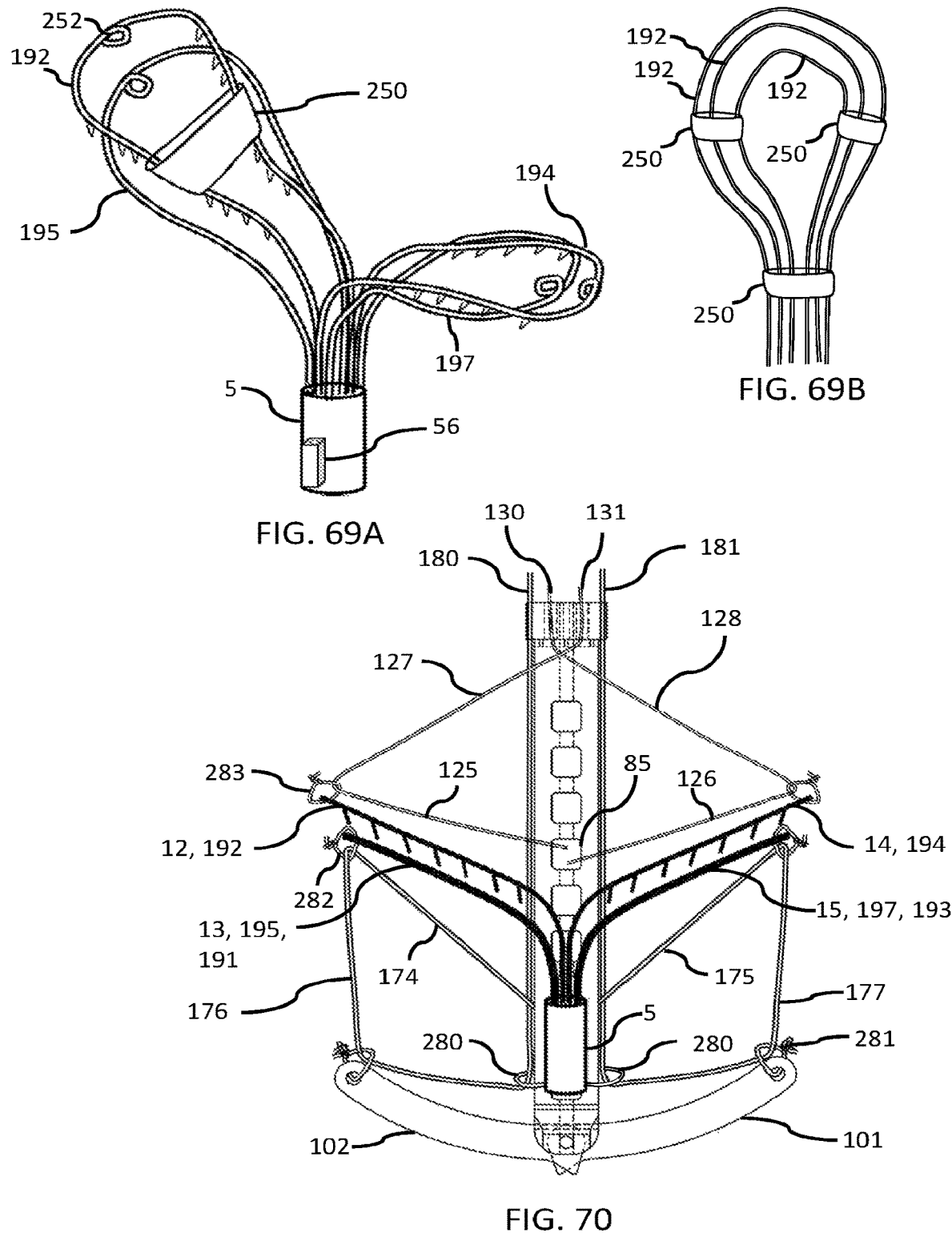

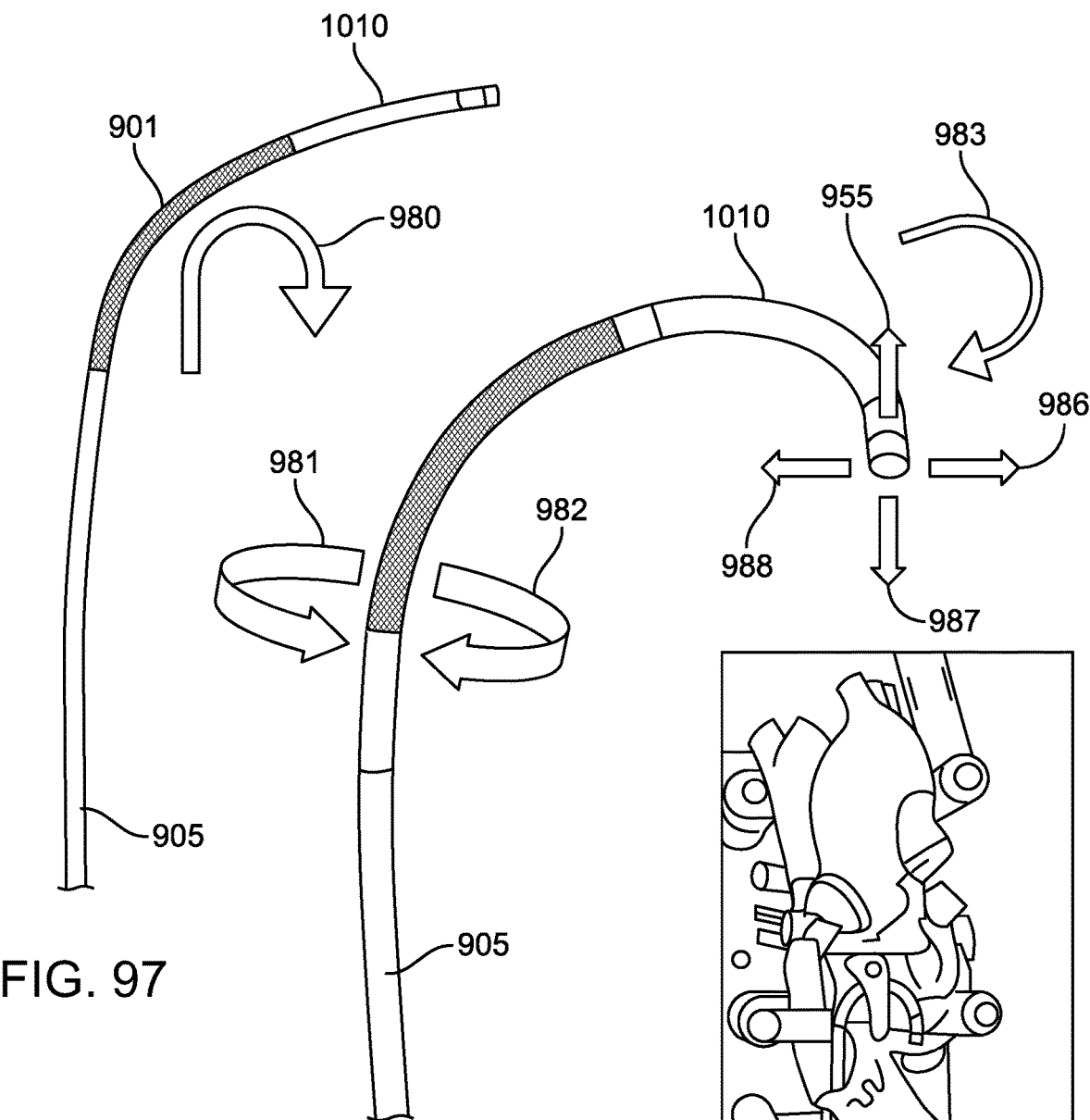
FIG. 97
FIG. 98
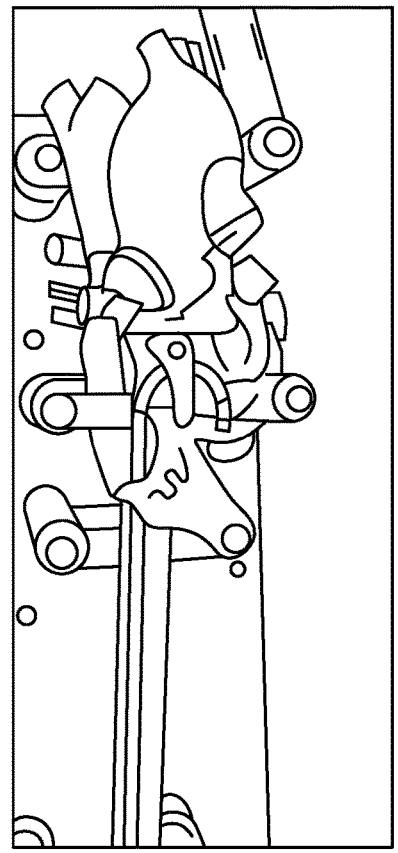
FIG. 99

TISSUE GRASPING DEVICES AND RELATED METHODS

CROSS-REFERENCE TO RELATED APPLICATIONS

This application is a continuation of PCT Application No. PCT/US2019/13853, filed Jan. 16, 2019, which claims the benefit of Provisional Application No. 62/617,946, filed Jan. 16, 2018, the entire content of which is incorporated herein by reference.

The disclosure of this application is related to that of PCT International Application Number PCT/US2017/042003 titled "TISSUE GRASPING DEVICES AND RELATED METHODS" filed on Jul. 13, 2017, the entire disclosure of which is incorporated herein by reference.

BACKGROUND OF THE INVENTION

1. Field of the Invention

The present invention relates generally to medical methods, devices, and systems. In particular, the present invention relates to methods, devices, and systems for the endovascular, percutaneous, or minimally invasive surgical treatment of bodily tissues, such as tissue approximation or valve repair. More particularly, the present invention relates to methods and devices for the repair of mitral and tricuspid heart valves, venous valves, and other tissue structure through minimally invasive and other procedures.

Surgical repair of bodily tissues often involves tissue approximation and fastening of such tissues in the approximated arrangement. When repairing valves, tissue approximation often includes coapting the leaflets of the valves in a therapeutic arrangement which may then be maintained by fastening or fixing the leaflets. Such fixation of the leaflets can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves, or the left ventricular wall may be damaged or otherwise dysfunctional. Commonly, the valve annulus may be damaged, dilated, or weakened, limiting the ability of the mitral valve to close adequately against the high pressures of the left ventricle during systole.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and is associated with high mortality and morbidity.

In some patients, a fixation device can be installed into the heart using minimally invasive techniques. The fixation device can hold the adjacent segments of the opposed valve leaflets together to reduce mitral valve regurgitation. One such device used to clip the anterior and posterior leaflets of the mitral valve together is the MitraClip® fixation device, sold by Abbott Vascular, Santa Clara, Calif., USA.

Fixation devices such as the MitraClip® valve leaflet fixation device often include clips designed to grip and hold valve tissue as the clip arms are moved and positioned against the tissue at the treatment site and then closed against the tissue. Such clips are designed to be closed into a final position and then mechanically lock into that position in order to continue gripping the tissue.

In addition, the act of grasping and closing into final position causes the leaflet and potentially the annulus to cinch. Considering that the MitraClip® is a relatively stiff device with steel (Elgiloy®) arms that are mechanically locked, the natural expansion and contraction of the annulus is altered.

Furthermore, in order to achieve bailout to remove or reposition the device, it is required to flex the device at extreme angles (to the point of inversion) to release the grasp. This extreme moving and deforming components of the fixation device during pre-deployment, positioning, closure and bailout of the device can lead to the weakening and premature degradation of the fixation device. In addition, it makes the device extremely complex with multiple components, and contributes to a relatively large overall size of the device, and therefore a correspondingly large (~24 Fr for MitraClip® fixation device) delivery system. This large catheter size presents additional trauma to the patients. In comparison, typical transseptal introducer sheaths are 8.5 Fr to 12 Fr (inner diameter) and 9 Fr to 16 Fr (outer diameter).

Some tissue fixation treatments require that the fixation device maintain a degree of flexibility and mobility to allow for a range of physiological movement even after the device has been properly deployed and the target tissue has been properly fixed into the desired position. This can increase the risk of premature failure of the device's complex locking mechanism as continued deformation of the flexing components (e.g., from the continuous opening and closing of valve leaflets) leads to unfavorable degradation of the device.

Depending on the anatomy and disease state of the valves, there can be variations in the coapting lengths and dissimilarities in leaflet shape in general (for example dissimilarities between anterior and posterior mitral valve leaflets). However, current devices and market leader MitraClip® fixation device came only one size and very recently added another size to the mix. However, the shape of the device is same, which is primarily optimized for degenerate mitral regurgitation. This can create issues for physicians when presented with various valve sizes, coapting lengths, frailty, and various functional and degenerative valve defects to be treated.

The ability to bailout and reposition is an important safety consideration for a majority of medical devices. The current market leader MitraClip® fixation device possesses these attributes to some extent, as it allows for bailout and repositioning. However, the barbs are on the sides the gripping arms, which creates a safety risk wherein tissue or delivery mechanisms may become caught in the barbs of the tissue grabbing features.

Finally, visualization during and after the procedure plays a critical role in the successful delivery of the device and outcome of the result. The current state-of-the-art device relies on fluoroscopy and transesophageal echocardiogram (TEE). It is TEE that primarily requires general anesthesia, adding significant risk to the old and frail patient population on whom this type of repair procedure is typically performed on.

For at least these aforementioned reasons, there is an ongoing need for:

a) Simpler device with fewer components: alternative and/or additional methods, devices, and systems for tissue fixation that may provide beneficial elasticity and durability of the flexing components without increasing the safety and manufacturing risks associated with numerous and complex components.

b) Lock-less device: a need for a simpler device to eliminate procedural risks related to locking of the device and the risks associated with failure of locking mechanisms post deployment.

c) Elastic and resilient device: a need for a device that gently cinches the annulus (or leaflets) while preserving some natural expansion and contraction of the annulus (or leaflets).

d) Smaller catheter size/profile: considering that most patients undergoing these treatments may be old and frail with multiple comorbidities, there is also a need to make the delivery device much smaller than 24 Fr to lower risk associated with vascular access.

e) Multiple device sizes: to provide such methods, devices, and systems in a manner that does not limit the tissue gripping ability of the fixation device. For example, to address small coaptation length and/or frail leaflets there may be a need for the ability to grasp beyond the coapting region of the leaflet, while conforming to the shape and length of the leaflets.

f) Tangle free design: The current market leader Mitra-Clip® fixation device has barbs exposed on both sides of the tissue grabbing feature. Tendons, tissue and device delivery mechanisms can become trapped by such exposed barbs. Hence, there is a need to improve on the safety of bailout and repositioning of the device that further mitigates the risk of tissue or delivery mechanisms getting stuck in the device during the procedure.

g) Visualization: there is need for improved visualization and feedback to perform the procedure safely and successfully with minimal trauma to the patient.

h) Local anesthesia: An ideal procedure would be under local anesthesia without the use of general anesthesia. This mitigates higher risks associated with general anesthesia.

At least some of these objectives will be met by the inventions and embodiments set forth below.

2. Description of the Background Art

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759; WO 2000/060995; WO 2004/103162. Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorne. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorne. Cardiovasc. Surg. 112:238-247 are review articles discussing the nature of and treatments for dilated cardiomyopathy.

Mitral valve annuloplasty is described in the following publications: Bach and Bolling (1996) Am. J. Cardiol. 78:966-969; Kameda et al. (1996) Ann. Thorne. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorne. Surg. 63:1805-1806. Tri-cuspid valve annuloplasty is described in McCarthy and Cos-grove (1997) Ann. Thorne. Surg. 64:267-268; Tager et al. (1998) Am. J. Cardiol. 81:1013-1016; and Abe et al. (1989) Ann. Thome. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262. Endovascular cardiac valve replacement is described in U.S. Pat. Nos. 5,840,081; 5,411,552; 5,554,185; 5,332,402; 4,994,077; and 4,056,854. U.S. Pat. No. 3,671,979 describes a catheter for temporary placement of an artificial heart valve.

Other percutaneous and endovascular cardiac repair procedures are described in U.S. Pat. Nos. 4,917,089; 4,484, 579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769, 812; and 5,718,725.

MitraClip® fixation devices, systems and methods of engaging tissue are described in U.S. Pat. Nos. 8,057,493; 7,226,467; and 10,159,570.

U.S. Patent Publication Nos. 2015/0257883 and PCT Publications WO2019/010370; WO2018/013856; and WO2017/015288 are of particular relevance to the present application where the lead inventor is the inventor herein.

SUMMARY OF THE INVENTION

This invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, particularly those in which the instruments utilized must negotiate long, narrow, and tortuous pathways to the treatment site. In addition, many of the devices and systems of the invention are adapted to be reversible and removable from the patient at any point without interference with or trauma to internal tissues.

In preferred embodiments, the devices, systems and methods of the invention are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation yet does not require open surgery through the chest and heart wall as in conventional approaches. In addition, the position of the leaflets may vary in diseased mitral valves depending upon the type and degree of disease, such as calcification, prolapse or flail. These types of diseases can result in one leaflet being more mobile than the other (e.g. more difficult to capture), and therefore more difficult to grasp symmetrically in the same grasp with the other leaflet. The features of the present invention allow the fixation devices to be adapted to meet the challenges of unpredictable target tissue geometry, as well as providing a more robust grasp on the tissue once it is captured. Additionally, the invention optionally incorporates visualization techniques to enable the device placement procedure to be performed without the use of general anesthesia.

The devices, systems and methods of the invention are centered on variety of devices which may be used individually or in a variety of combinations to form interventional systems. In preferred embodiments, the interventional system includes a multi-catheter guiding system, a delivery catheter and an interventional device. Each of these components will be discussed herein.

In an exemplary embodiment, the invention provides a fixation device having a pair of arms (or fixation elements), each arm having a free end and an engagement surface for engaging the tissue, wherein the arms are moveable between a first position for capturing the tissue and a second position for fixing the tissue. Preferably, the engagement surfaces are spaced apart in the first position and are closer together and generally face toward each other in the second position. Preferably, the arms are resiliently biased towards each other. The arms may have frictional elements such as barbs or teeth and in a preferred embodiment, the barbs or teeth may be saw-tooth shaped. The fixation device preferably comprises of one or two or three or more pair of arms and is delivered to a target location in a patient's body by a delivery catheter having an elongated shaft, a proximal end and a distal end, the delivery catheter being configured to be positioned at the target location from a remote access point such as a vascular puncture or cut-down or a surgical penetration. In a preferred embodiment, the target location is a valve in the heart. In a preferred embodiment, a pair of arms as described above comprises of an inner arm that captures the leaflet from the atrial side and an opposing outer arm that captures the leaflet from the ventricular side. The arms may have frictional elements such as barbs or teeth and in a preferred embodiment, only the inner arm has frictional elements.

A particular advantage of the present invention is its ability to coapt the leaflets of the mitral valve (or any other tissue with which it is used) in a parallel or vertical relationship using two pair of arms. In other words, the leaflets may be captured, drawn together and fixed such that their proximal upstream surfaces are disposed parallel to each other and generally aligned with the direction of flow through the valve at the point of coaptation. In some embodiments of the fixation device, the use of sufficiently stiff outer arms, highly frictional and flexible inner arms and a passive closure mechanism enables the leaflets to be grasped in a spaced-apart relationship and then drawn together in a coapted relationship while keeping the leaflets vertical (aligned with blood flow) to achieve the optimal coapted configuration.

A particular advantage of the present invention is its ability to coapt the leaflets of the mitral valve (or any other tissue with which it is used) in a parallel or vertical relationship while grasping alongside the anatomical contours of the leaflets. In other words, the leaflets may be captured, drawn together, and fixed such that their proximal upstream surfaces are disposed parallel to each other and generally aligned with the direction of flow through the valve at the point of coaptation, while additionally grasping alongside the anatomical contours away from the coaptation. In some embodiments of the fixation device, the use of sufficiently flexible outer arms, highly frictional, compressive and/or flexible inner arms and a passive closure mechanism enables the leaflets to be grasped in a spaced-apart relationship and then drawn together in a coapted relationship while keeping the leaflets vertical (aligned with blood flow) to achieve the optimal coapted configuration.

A particular advantage of the present invention is its ability to coapt the leaflets of the mitral valve (or any other tissue with which it is used) in a close anatomical relationship of the leaflet shape, while grasping alongside the anatomical contours of the leaflets. In other words, the leaflets may be captured, drawn together and fixed such that their natural anatomical shape is retained. In some embodiments of the fixation device, the use of sufficiently flexible outer arms, highly frictional and flexible inner arms and a passive closure mechanism enables the leaflets to be grasped in a spaced-apart relationship and then drawn together in a coapted relationship while keeping sufficient length of the leaflets vertical (aligned with blood flow) to achieve the optimal coapted configuration, while grasping the leaflets alongside the natural contours beyond the coaptation length.

The fixation device is preferably delivered with the outer arms in a delivery position configured to minimize the profile of the device. When approaching the mitral valve from the atrial side, some embodiments of the fixation device allow the device to be delivered with the free ends of the outer arms pointing in a generally proximal direction forming an angle of less than about 90°, preferably less than about 20°, relative to the longitudinal axis of the delivery device shaft. In this position the engagement surfaces are facing generally toward each other, being disposed at an angle of less than about 180°, and preferably less than about 40°, relative to each other. For ventricular approaches, in the delivery position the free ends of the outer arms are pointing in a generally distal direction and form an angle of less than about 90°, preferably less than about 20° relative to the longitudinal axis of the delivery device shaft. In this position, the engagement surfaces are facing generally toward each other, usually being disposed at an angle of less than about 180°, and preferably less than about 90°, relative to each other. Alternatively, in some ventricular approaches, it may be preferred to have the free ends of the fixation elements pointing in a generally proximal direction and the engagement surfaces facing away from each other in the delivery position.

In order to provide for the reversibility and removability of the devices and systems of the invention, the leaflets are lifted off the sufficiently flexible outer arms using sutures or actuating wires to effectively mimic inversion of the outer arms, which minimizes entanglement and interferences with surrounding tissues should the device be desired to be withdrawn. In mitral repair applications, this is particularly important due to the presence of chordae tendineae, valve leaflets and other tissues with which devices may become entangled. For approaches from the atrial side of the mitral valve (in the mimicked inverted position), the sutures or wires are disposed at an angle of more than about 180°, and preferably more than 270° relative to each other. For ventricular approaches to the valve in the mimicked inverted position, the suture or wires will be pointing in a distal direction relative to the catheter shaft and the engagement surfaces will be facing generally toward each other, usually being disposed at an angle of less than about 180°, and preferably less than 90° relative to each other.

A particular advantage of this invention is that it allows for inversion of arms with the use of inverters, by enabling the direction of the pull force exerted by the sutures or actuating wires. One example of inverters used in this invention are lever arms that swing close to allow for low profile during passage through the catheter system and swing apart to provide the increased lever arm necessary to invert the arms.

In the open position the engagement surfaces of the outer arms preferably form an angle of up to 180° relative to each other so as to maximize the area in which to capture the valve leaflets or other target tissue. The outer arms are preferably flexible to a closed position in which the engagement surfaces engage each other or form an angle as small as 0° or less relative to each other. The outer arms are configured to be flexible and left permanently in any of various positions while exerting a compressive force that is same or exceeding the forces of the opposing inner arms to allow for the fixation of tissues of various thickness, geometry, and spacing.

A particular advantage of this invention is that both outer and inner arms are sufficiently superelastic and flexible to exert persistent and gentle (atraumatic) opposing forces on the tissue, while allowing for small movements to conform with a) anatomical shape of the leaflet and b) physiological forces on the leaflets.

A particular advantage of this invention is that both outer and inner arms are sufficiently superelastic, resilient and flexible, which on capturing the leaflets in an open state to closed final configuration, exert a gentle therapeutic cinch on the annulus (directly or via the leaflets), while preserving some natural expansion during diastole and aiding natural contraction of the annulus during systole. This gentle cinch on the annulus potentially promotes positive remodeling of the annulus, especially in dilated annulus of enlarged hearts. Additionally, it better preserves the natural annulus expansion during diastole, which in turn increases the orifice area of the valve for enhanced blood flow from atria to ventricles during diastole. While the valve clips of the present invention will be less traumatic and more flexible than the MitraClip® device, the clips will still be sufficiently robust to firmly clamp and immobilize the valve leaflets so that they can function as desired to improve flow control through the treated valve.

A particular advantage of this invention is that it is possible to have various sizes and shapes of arms or pairs of arms that can be attached to the same catheter delivery system. A particular advantage of this invention is that the opposing forces of inner and outer arms can be configured to desired specifications by varying material, thickness, width, length, shape, cut pattern of each of the inner arm or its corresponding outer arm. For example, the opposing forces of the outer arm can be same, less or more than the inner arm. In a preferred embodiment, the opposing forces of the outer arm is either 1, 1.2, 1.5, 2, 3, 5, 10, 20, 30 or more times than that of the inner arm.

Another particular advantage of this invention is that the frictional elements (barbs) are placed medially along the long axis of the arm body and confined by continuous and solid side surface. Unlike in the MitraClip® device, the barbs are not exposed along the sides. This is advantageous as it significantly reduces the risk of entanglement of chordae tendineae, valve leaflets and other tissues with which devices may become entangled. Further, this feature reduces the risk of entanglement or sutures or wires or other such delivery catheter elements that may potentially come in contact with the fixation device.

A particular advantage of this invention is that in configurations where the barbs are on the side (as in MitraClip® device), side guard rail like feature or plugs along the side of the barbs are used to prevent unintended entanglements.

In a preferred embodiment, the fixation device of the invention will further include at least one inner arm (or gripping element) and one outer arm (or coapting element). Each inner arm and outer arm will be movable relative to each other and configured to capture tissue between the inner arm and the engagement surface of the outer arm. Preferably, the outer arms and inner arms are independently movable but, in some embodiments, may be movable with the same mechanism. The inner arm may be preferably biased toward the engagement surface of the fixation element and vice-versa to provide a compressive force against tissue captured there between.

In a preferred configuration comprising of two pair of arms, the outer arms are positioned at each side and the two inner arms are sandwiched between them, and the outer arms are configured to have exert more apposing force than the inner arms. This not only provides additional compressive force against the captured tissue, but also forcefully coapts the tissue captured between each pair of arms. One particular advantage of this invention is that the coapting force can be preconfigured to a desired force, by configuring thickness, size, width, shape, profile, material, Af, coldwork and/or other features of the arms. One particular advantage of this invention is that this coapting force can additionally be used to cinch of the anulus, when used on a valve.

In another aspect, the invention provides a fixation device comprising of a coupling member configured for coupling to a catheter and a pair of outer arms connected to the coupling member, in which each outer arm holds an engagement surface in order to grasp the tissue.

In some applications such as the repair of the mitral valve, the fixation device is adapted to be detached from the delivery catheter and left permanently in the patient. In such applications, it is often desirable to promote tissue growth around the fixation device. For this purpose, some or all of the components of the fixation device are preferably covered with a covering or coating to promote tissue growth and improve biocompatibility. In one embodiment, a biocompatible fabric cover is positioned over the outer arms and/or the inner arms. The cover may optionally be impregnated or coated with various therapeutic agents, including tissue growth promoters, anti-biotics, anti-clotting, blood thinning, and other agents. Alternatively, or in addition, some or all of the fixation element and/or covering may be comprised of a bioerodible, biodegradable, or bioabsorbable material so that it may degrade or be absorbed by the body after the repaired tissues have grown together. In a preferred embodiment, the coating and/or covering can be used to limit or eliminate leachables (for example nickel ion leaching in nitinol) to further improve biocompatibility (and/or mitigate allergic reactions).

In some applications such as the repair of the mitral valve, the fixation device is adapted to be detached from the delivery catheter and left temporarily in the patient. In such applications, it is often desirable to not promote tissue growth around the fixation device, while providing a hemocompatible and biocompatible surface. For this purpose, some or all of the components of the fixation device are preferably covered with a covering or coating to promote hemocompatibility without tissue growth. In one embodiment, a biocompatible fabric cover is positioned over the outer arms and/or the inner arms. The cover may optionally be impregnated or coated with various therapeutic agents, including tissue growth inhibitors, anti-biotics, anti-clotting, blood thinning, and other agents. Alternatively, or in addition, some or all of the fixation element and/or covering may be comprised of a bioerodible, biodegradable, or bioabsorbable material so that it may degrade or be absorbed by the body after the repaired tissues have grown together.

The outer arms and inner arms will be configured to provide sufficiently high retention force so that the fixation device remains securely fastened to the target tissue throughout the cardiac cycle. At the same time, the outer and inner arms will be configured to minimize any acute trauma to the tissue engaged by them. This allows the fixation device to be removed from the tissue after initial application without creating clinically significant injury to the tissue. In order to enhance retention without creating significant trauma, the inner arms and/or the outer arms may have friction-enhancing features on their surfaces that engage the target tissue. Such friction-enhancing features may include barbs, bumps, grooves, openings, channels, surface roughening, coverings, and coatings, among others. Preferably, the friction-enhancing features will be configured to increase the retention force of the distal and inner arms on the tissue, while not leaving significant injury or scarring if the device is removed. For example, instead of long and sharp pointed barb, the barb tip may have tiny tooth or teeth that limit complete penetration of the barb into the tissue, thereby mitigating risk of tissue perforation.

The outer and inner arms may further have a shape and flexibility to maximize retention force and minimize trauma to the target tissue. In a preferred embodiment, the engagement surfaces of the outer arms have a concave shape configured to allow the inner arms, along with the target tissue, to be nested or recessed within the outer arms. This increases the surface area of the tissue engaged by the outer arms and creates a geometry of tissue engagement that has a higher retention force than a planar engagement surface. To minimize trauma, the longitudinal edges as well as the free ends of the outer arms are preferably curved outwardly away from the engagement surface so that these edges present a rounded surface against the target tissue. The outer arms and/or the inner arms may also be flexible so that they deflect to some degree in response to forces against the tissue engaged thereby, reducing the chances that the tissue will tear or be damaged in response to such forces.

The fixation device will include an actuation mechanism for moving the outer arms between the open, closed, and inverted positions. A variety of actuation mechanisms and inverters may be used. In an exemplary embodiment, sutures or strings or wires or levers that are controllable by the delivery system handles by the user, maybe used to raise and lower the outer or inner arms to capture the leaflets.

A particular advantage of this invention is the ability to move all arms independently to capture the tissue one at a time or simultaneously between each pair of arms.

The fixation device of the invention preferably includes a coupling member that is detachably connectable to the delivery catheter. The coupling member may have various constructions, but in an exemplary embodiment comprises a flexible rod, wire or stylet of sufficient tensile strength, that coaxially and slidably extends from the handle to the fixation device. When the user(s) desires, they manipulate the handle safety release mechanisms that allows for retraction of the coupling member or release rod. This in turns cause the coupling member to slide out of the engaging elements between the delivery system and the fixation device. The delivery catheter will be configured to detachably connect to both the coupling member and fixation device. In one embodiment, the delivery catheter has a round hole through an elongated member and a rod/wire/stylet slidably disposed in the hole of the elongated member. The junction of the coupling member, elongated member and the fixation device comprises a mating surface which may have a variety of shapes including sigmoid curves or angular or planar surfaces. The release rod/wire/stylet extends from the delivery catheter through the axial channel in the outer member to maintain its connection with the fixation device. The rod/wire/stylet may be connected by various connection structures, including threaded connections. Detachment and retraction of the release rod/wire/stylet back into the delivery catheter decouples the delivery catheter (including actuation sutures/wires) to allow deployment of the fixation device. Further, by strategically configuring the device and suture attachment points with delivery system, the extent and rate of device decoupling can be controlled by the amount of retraction of the release rod by the user.

The delivery device of the present invention delivers interventional devices to a target location with a body. Such interventional devices particularly include fixation devices or any devices which approximate tissue, such as valve leaflets. The delivery devices and systems direct the interventional device to the target location through a minimally invasive approach, such as through the patient's vasculature, and provide for manipulation of the interventional device at the target location, such as to approximate tissue. Optionally, the delivery devices and systems may provide for decoupling of the interventional device, allowing the interventional device to be left behind as an implant.

In an aspect of the present invention, a delivery device is provided comprising an elongated flexible shaft preferably suitable for introduction through tortuous passageways in the body. The elongated shaft has a proximal end, a distal end, and a main lumen there between. Included in the delivery device is at least one elongated body, particularly at least one flexible tubular guide, extending through the main lumen. In some embodiments, the tubular guide is fixed to the shaft near the proximal end and near the distal end and is unconstrained relative to the shaft there between so as to be laterally moveable within the main lumen. Alternatively, the tubular guide may be unconstrained in only a distal portion of the shaft so as to provide greater flexibility of that portion.

In some embodiments, two flexible tubular guides are present. However, three, four, five, six or more flexible guides may alternatively be present. The tubular guides may be comprised of any suitable material which provides lateral flexibility while providing strength under compression, such as a metallic or polymeric coil. In addition, other elongated bodies may be present, such as rods, tubes, wires, sutures, stylets to provide additional strength or elasticity. In some embodiments, the main lumen is occupied by fluid so that the elongated bodies are surrounded by such fluid. In some element, nitinol rods may be used to keep the catheter shaft straight (when unrestrained), despite passing through tortuous anatomical curves.

In an aspect of the present invention, the delivery device includes an actuation element movably disposed in at least one of the flexible tubular guides and extending between the proximal and distal ends. The actuation element is adapted for coupling with a movable component of an interventional element so that movement of the actuation element moves the movable element. Such an interventional element is typically removably coupled to the distal end of the shaft. The moveable component may have any of a variety of functions, including grasping, approximating, cutting, ablating, stapling or otherwise engaging tissue. In one embodiment, the moveable component provides for approximation of tissue, such as coaptation of valve leaflets. In preferred embodiments, the interventional element has first and second tissue engaging elements adapted for engaging tissue there between. Thus, in these embodiments, the actuation element is used to move the tissue engaging elements to engage the tissue. Further, in some embodiments, the shaft and interventional element are adapted for positioning through a blood vessel.

In an aspect of the present invention, a system is provided for approximating tissue at a treatment site. In some embodiments, the system comprises an elongated flexible shaft having a proximal end, a distal end, a main lumen there between, and at least one flexible tubular guide extending through the main lumen. Again, in preferred embodiments the tubular guide is fixed to the shaft near the proximal end and near the distal end and is unconstrained in at least a portion of the main lumen there between so as to be laterally movable within the main lumen. Nitinol wires, rods, springs, and/or tubes or other elastic, superelastic and/or shape memory materials may be used in this unconstrained section to keep them resiliently straight. In some embodiments, the system also includes an actuation element movably disposed in the tubular guide, and an approximation device coupled to the distal end of the shaft, the approximation device having first and second engaging elements for engaging tissue there between, at least one of the engaging elements being movable and coupled to the actuation element.

The delivery device of the invention is adapted to allow the user to deliver the fixation device to the target site from a remote access point (whether through endovascular or surgical approaches), align the device with the target tissue, and to selectively close, open, invert, lock, or unlock the outer arm. The delivery device will preferably have a highly flexible, kink and torsion resistant shaft with minimal elongation and high tensile and compressive strength. The delivery device will also have the movable components and associated actuators used to move the arms between the lowered and raised positions, to move the arms into engagement with the target tissue, and to detach the outer arm from the delivery catheter. A plurality of tubular guides, preferably in the form of coils, tubes or multi-lumen tubes preferably with low coefficient of friction, extend through the inner lumen of the shaft and are fixed to the shaft near its proximal and distal ends but are unrestrained there between, providing a highly flexible and kink-resistant construction. In a preferred embodiment, a multilumen braided shaft with varying durometer may be used. Further, superelastic, elastic and/or shape memory materials are used, particularly in the unconstrained region immediately proximal to the device attachment for increased flexibility with resilience to remain straight (when unconstrained). Lines/rods for actuating the arms and the deployment mechanism of the fixation device extend through these tubular guides and are detachably coupled to the arm and the device. In an exemplary embodiment, the lines/wires/sutures allow the ability to pull only. In an exemplary embodiment, the lines are fully or partially combined with rods (for example a suture loop crimped to the end of a rod) or reinforced with a tube/braid to allow for ability to pull as well as push. The ability to push is desired to overcome the friction of sliding of the lines/wires within the catheter lumens or to further actuate the device.

The delivery catheter may additionally include a tether comprised of a suture or wire or flexible rod that is detachably coupled to a portion of the fixation device for purposes of retrieval of the device following detachment from the delivery catheter. The tether may be a separate flexible filament extending from the delivery catheter to the fixation device, but alternatively may be the same line used to actuate the arms or device. In either case, the tether will be detachable from the fixation device so that it may be detached once the device has been deployed successfully.

In some embodiments, the delivery device further includes an actuation element movably disposed in at least one flexible tubular guide, and a fixation device coupled to the distal end of the shaft and adapted for positioning in the chamber of the heart. Typically, the fixation device is releasably coupled to the shaft. In some embodiments, the fixation device has at least one inner arm and at least one outer arm adapted to engage a valve leaflet between them, wherein at least one of the inner and outer arms is movable and coupled to the actuation element. Alternatively, or additionally, the actuation element comprises a flexible line such as a suture loop and optionally an inverter.

The system may further comprise first and second flexible tubular guides extending from the proximal end to the distal end through the main lumen. The first and second tubular guides are preferably fixed to the shaft near the proximal end and near the distal end and are unconstrained in at least a portion of the main lumen there between so as to be laterally movable within the main lumen. Further, the first movable element extends through the first tubular guide and the second movable element is movably disposed in the second tubular guide.

The system may also further comprise an actuator handle connected to the proximal end of the shaft, the actuator handle having a body and first, second and third actuation elements movably coupled thereto, the first, second and third actuation elements being coupled to the first, second and third movable elements.

Systems of the invention may additionally include a guide that facilitates introduction and navigation of the delivery catheter and fixation device to the target location. The guide is preferably tubular with a channel extending between its proximal and distal ends in which the delivery catheter and fixation device may be slidably positioned. The distal end of the guide is steerable, usually being deflectable about at least one axis, and preferably about two axes or 4 axes. The guide may have more than one such deflectable distal segments in tandem or with some spacing. The guide will have a size, material, flexibility and other characteristics suitable for the application in which it is being used. For mitral valve repair, the guide is preferably configured to be introduced in a femoral vein and advanced through the inferior vena cava into the heart, across a penetration in the interatrial septum, and into alignment with the mitral valve in the left atrium.

Alternatively, the guide may be configured to be introduced in a brachiocephalic or axillary or carotid vein (neck/shoulder access) and advanced through the superior vena cava into the heart, across a penetration in the interatrial septum, and into alignment with the mitral valve in the left atrium.

Alternatively, the guide may be configured for introduction in a femoral, axillary, or brachiocephalic artery and advancement through the aorta and aortic valve into the ventricle where it is steered into alignment with the mitral valve. In a further alternative, the guide may be configured for introduction through a puncture or incision in the chest wall and through an incision in the wall of the heart to approach the mitral valve.

In an exemplary embodiment, the guide comprises a multi-catheter guiding system which has two components, including an inner tubular member or inner guide catheter and an outer tubular member or outer guide catheter. The outer tubular member has a distal end deflectable about an axis. The inner tubular member has a distal end deflectable about an additional axis. Further, the distal end of inner tubular member may be angularly deflectable. Mobility in additional directions and about additional axes may optionally be provided.

The invention further provides methods of performing therapeutic interventions at a tissue site. In one embodiment, the method includes the steps of advancing an interventional tool having a proximal end, a distal end and a fixation device near the distal end to a location within a patient's body, wherein the fixation device includes a pair of outer arms each having a free end and an engagement surface; moving the outer arms to an open position wherein the free ends are spaced apart; positioning the outer arms such that the engagement surfaces engage tissue at the tissue site; and detaching the fixation device from the interventional tool. Preferably, the method further includes the step of decoupling the leaflets off the outer arms, to allow for bailout or re-attempt the procedure.

At least one embodiment of the present disclosure relates to a tissue gripping device including: a base section; and a first outer arm having a free end and a fixed end that is coupled to the base, and a first inner arm having a free end and a fixed end that is coupled to the base, followed by second outer arm and a second inner arm that are similarly coupled to the base in a modular fashion; wherein, the tissue is grasped between the outer and inner arms; and wherein the outer and inner arms are formed of an elastic-plastic material or rheological material or shape-memory material configured to exhibit superelasticity in a physiological environment, and the base is formed of elastic/plastic material or shape-memory material configured to exhibit superelasticity in a physiological environment. In an alternative embodiment, each pair of inner and outer arms are coupled to a different bases, with an ability to cinch or attach or bond the two bases together, pre, post, and/or during the procedure.

At least one embodiment of the present disclosure relates to a tissue fixation system configured for intravascular delivery and for use in joining mitral valve (or tricuspid valve) tissue during treatment of the mitral valve (or tricuspid valve), the system including: the tissue gripping device including: a base section; and a first outer arm having a free end and a fixed end that is coupled to the base, and a first proximal arm having a free end and a fixed end that is coupled to the base, followed by second outer arm and a second proximal arm that are similarly coupled to the base in a modular fashion; wherein, the tissue is grasped between the inner and outer arms; and wherein the inner and outer arms are formed of a shape-memory material configured to exhibit superelasticity in a physiological environment, and the inner and outer arms are independently movable, and the base is formed of titanium, stainless steel, metal, plastic, ceramic, elastic/plastic material and/or shape-memory material configured to exhibit superelasticity in a physiological environment.

At least one embodiment of the inner or outer arms have barbs that are encompassed within smooth outside edges or barriers or plugs on either side of the barbs, to limit the risk of tissue or delivery mechanisms getting stuck in the barbs; and wherein, the barbs are formed of an elastic-plastic material or rheological material or shape-memory material configured to exhibit superelasticity in a physiological environment. At least one embodiment of the inner or outer arms have barbs that limits the full-length penetration to mitigate trauma or perforation of the tissue (for example, using a v-shaped barb tip that prevents tissue to penetrate beyond the depth of barb)

In at least one embodiment of the fixation device delivery system, there is a provision for a standalone or a dedicated probe built into the delivery system that incorporates an active ultrasonic probe; wherein the probe is retractable, translatable, rotatable, steerable, and has at least one or more features such as and not limited to: 2-D imaging, Doppler, 3D imaging, 4-D imaging, multimodality imaging features, with or without the use of ultrasonic markers or contrast agents; in-synchronization or out of synchronization to limit physiological artifacts (caused by for example and not limited to heartbeat and breathing); to help assist, identify, and navigate pre-procedure, during procedure, and post-procedure.

At least one embodiment of the fixation device delivery system, there is a provision for a standalone or a dedicated probe built into the delivery system that incorporates an passive ultrasonic probe; wherein the probe is retractable, translatable, rotatable, steerable, and has at least one or more multimodality imaging enabling features such as and not limited to: 2-D imaging, Doppler, 3D imaging, 4-D imaging, with or without the use of ultrasonic markers or contrast agents; in-synchronization or out of synchronization to limit physiological artifacts (caused by for example and not limited to heartbeat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an active Optical Coherence Tomography (OCT) probe; wherein the probe is retractable, translatable, rotatable, steerable, and has at least one or more enabling features such as and not limited to: 2-D imaging, Doppler, 3D imaging, 4-D imaging, multimodality imaging features, with or without the use of OCT markers or contrast agents; in-synchronization or out of synchronization to limit physiological artifacts (caused by for example and not limited to heartbeat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an passive Optical Coherence Tomography (OCT) probe; wherein the probe is retractable, translatable, rotatable, steerable, and has at least one or more features such as and not limited to: 2-D imaging, Doppler, 3D imaging, 4-D imaging, multimodality imaging features, with or without the use of OCT markers or contrast agents; in-synchronization or out of synchronization to limit physiological artifacts (caused by for example and not limited to heartbeat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an active optical camera based imaging system housed inside a balloon; wherein, the balloon maybe filled with fluid (gas or liquid) that allows for visualization when the balloon is either in contact or vicinity of the target tissue; wherein the probe is retractable, translatable, rotatable, steerable, and has at least one or more enabling features such as and not limited to: 2-D imaging, Doppler, 3D imaging, 4-D imaging, multimodality imaging features, with or without the use of optical markers or contrast agents; in-synchronization or out of synchronization to limit physiological artifacts (caused by for example and not limited to heartbeat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an passive optical camera based imaging system (for example and not limited to optical fiber imaging system) housed inside a balloon; wherein, the balloon maybe filled with fluid (gas or liquid) that allows for visualization when the balloon is either in contact or vicinity of the target tissue; wherein the probe is retractable, translatable, rotatable, steerable, and has at least one or more features such as and not limited to: 2-D imaging, Doppler, 3D imaging, 4-D imaging, multimodality imaging features, with or without the use of optical markers or contrast agents; in-synchronization or out of synchronization to limit physiological artifacts (caused by for example and not limited to heartbeat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an active sensor/transducer/actuator system; wherein the probe is retractable, translatable, rotatable, steerable, and has at least one or more enabling features such as and not limited to: pressure, strain, stress, ECG, EMG, 2-D imaging, Doppler, 3D imaging, 4-D imaging, multimodality imaging features, with or without the use of markers or contrast agents; in-synchronization or out of synchronization to limit physiological artifacts (caused by for example and not limited to heartbeat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an passive sensor/transducer/actuator system (for example and not limited to RFID based systems); wherein the probe is retractable, translatable, rotatable, steerable, and has at least one or more enabling features such as and not limited to: pressure, strain, stress, ECG, EMG, 2-D imaging, Doppler, 3D imaging, 4-D imaging, multimodality sensing/transducing features, with or without the use of markers or contrast agents; in-synchronization or out of synchronization to limit physiological artifacts (caused by for example and not limited to heartbeat and breathing); to help assist, identify, and navigate pre-procedure, and/or during procedure, and/or post-procedure.

At least one embodiment of the fixation device delivery system, there is a provision for the device to coated to enhance biocompatibility and tissue interface, wherein, the coating maybe with metals (for example and not limited to: titanium, tantalum, gold, platinum, iridium, tungsten or their combination), and/or ceramics, and/or polymers for example and not limited to: fluoropolymers (PTFE, PFA, FEP, ECTFE, ETFE), parylene, polyester, PER, polypropylene, PEEK, PVDF, HDPE, LDPE, UHMWPE, Phosphorylcholine, hydroxyapatite, CaP, THV, biodegradable materials (polylactic acid, polyglycolic acid), Bioerodible materials such as polydioxanone, poly(ε-caprolactone), polyanhydride, poly(ortho ester), copoly(ether-ester), polyamide, polylactone, poly(propylene fumarate) and/or their combinations; wherein, these coatings may be hydrophilic or hydrophobic.

At least one embodiment of the fixation device delivery system, there is a provision for the device to coated to enhance biocompatibility and tissue interface, wherein, the coating may be with metals (for example and not limited to: titanium, tantalum, gold, platinum, iridium, tungsten or their combination), and/or ceramics, and/or polymers for example and not limited to: fluoropolymers (PTFE, PFA, FEP, ECTFE, ETFE), parylene, polyester, PER, polypropylene, polyurethane, PEEK, PVDF, HDPE, LDPE, UHMWPE, Phosphorylcholine, hydroxyapatite, CaP, THV, and biodegradable materials (polylactic acid, polyglycolic acid), Bioerodible materials such as polydioxanone, poly(ε-caprolactone), polyanhydride, poly(ortho ester), copoly(ether-ester), polyamide, polylactone, poly(propylene fumarate) and/or their combinations; wherein, these coatings may be hydrophilic or hydrophobic.

At least one embodiment of the present disclosure relates to a method of gripping tissue, the method including: positioning a tissue gripping device near a target tissue, the tissue gripping device being formed from a shape-memory material and including a base section and a first arm and a second arm, each arm having a first end coupled to the base section and a free end extending from the base section, the first and second arms being disposed opposite one another; and moving the tissue gripping device from a pre-deployed configuration toward a deployed configuration, the first and second arms being configured to resiliently flex toward a relaxed configuration in a distal direction as the tissue gripping device is moved from a pre-deployed configuration toward a deployed configuration.

At least one embodiment of the present disclosure relates to a method of manufacturing a tissue gripping device, the method including: cutting one or more structural features into a strip or sheet stock material of a shape-memory alloy, the one or more structural features including a plurality of slotted recesses disposed at one or more sites away from side edges of the stock material; and heat shape setting one or more bend features into the stock material.

In a first specific aspect, a valve clip according to the present invention comprises a hub, a first pair of leaflet capture arms comprising a first inner arm and a first outer arm coupled to the hub, and a second pair of leaflet capture arms comprising a second inner arm and a second outer arm coupled to the hub. The outer and inner arms are configured to be biased apart to create a leaflet capture space therebetween and to self-close over a valve leaflet when unbiased after the leaflet has been captured The hub is typically configured to be removably attached to a deployment shaft, and at least some of the leaf capture arms are typically formed as a leaf spring. An outer surface of each inner arm is positioned adjacent to an inner surface of each outer arm, and an inferior end of each arm is coupled to the hub, with the inferior ends of each inner arms typically being superior to the inferior ends of each outer arm. The terms "inferior" and "superior" are defined relevant to the patient anatomy in which the valve clip will be implanted. For example, when implanted in a mitral valve, superior refers to the side of the clip facing the atrium while inferior refers to the side of the clip facing the ventricle. When planted in a vein, superior will refer to the upstream direction while inferior refers to the downstream direction.

The spring-biased outer and inner arms are configured to be "opened" to initially capture a pair of valve leaflets and to self-close over the valve leaflets after the leaflets have been captured. By "opened" it is meant that the individual arms can be bent or biased so that they are moved out of their normal, unbiased configurations, i.e. when they are free from deformation due to the application of an external force.

In particular embodiments, at least some of the outer and inner arms of the valve clip are formed as "leaf springs" with a resilient base and a less-resilient (more rigid) valve-grasping element. The resilient base will usually provide most or all of the resilience or bending capability for the leaf spring structure and is configured so that it may be attached directly or indirectly to the hub and. The valve-grasping element (for example and not limited to barbs), in contrast, will usually experience little or no bending when deployed over the leaflets of a target valve. Usually all of the outer and inner arms will have the configurations as described.

In other specific embodiments, the adjacent outer and inner arms of the valve clip will have generally congruent shapes. By generally congruent, it is meant that the outer and inner arms will have the same or complementary shapes and will be able to "nest" when attached to the hub and in their unbiased configurations. There will usually be a small distance or gap between the inferior surfaces of the inner arms and the superior surfaces of the outer arms, typically from 0 mm to 6 mm, preferably from 0.5 mm to 2.5 mm, when the outer and inner arms are in their unbiased configurations to accommodate the valve leaflets therebetween when the valve leaflets are captured by the valve clip. These gap values accommodate a typical thickness of a single leaflet between inner and outer arms. In other specific embodiments wherein two or more leaflets are captured between the pair of arms, these gap values may be increased two or three-fold. While there can be a minimum gap, the spring-bias of the arms may be sufficient by itself to accommodate a full range of leaflet wall thicknesses.

In a first illustrated embodiment, the valve-grasping elements of the valve clip will diverge from a common axis through the hub to form a V-shape when the outer and inner arms are unbiased. Typically, the resilient base is curved, and the valve-grasping elements are straight in both the outer and inner arms. Still more typically, the resilient bases on the outer arms have an S-shaped curve selected to offset or separate the superior surfaces of the outer arms from inferior surfaces of the inner arms in order to provide the gap or separation to accommodate the valve leaflets as described previously. Alternatively, a spacer may be used in between the arms to create space to accommodate the leaflets.

In other illustrated embodiments, the valve-grasping elements are parallel to a common axis through the when the outer and inner arms are unbiased. In such instances the inner arms are generally straight, but the bases of the outer arms have a curve selected to separate superior surfaces of the outer arms from inferior surfaces of the inner arms in order to accommodate the valve leaflets there between.

In a second aspect of the present invention, a system for delivering valve clip to a heart or venous valve will comprise any of the valve clip designs described above or elsewhere or herein. The systems will further comprise a deployment shaft configured to be removably attached to the hub of the valve clip.

In particular embodiments of the systems of the present invention, the deployment shaft may extend from the hub in a superior direction along an axis of symmetry through the hub and between right-side outer and inner arms and left-side outer and inner arms.

In exemplary embodiments, the system further comprises a steerable deployment catheter removably or fixedly coupled to the deployment shaft. In some instances, an inferior end of the deployment shaft is configured to be coupled to the steerable deployment catheter. In other instances, a superior end of the deployment shaft is configured to be coupled to the steerable deployment catheter.

In still further embodiments, the steerable catheter may include an imaging component to allow real-time visualization of an implantation procedure. The imaging component may include one or more of optical imaging components, ultrasound imaging components, OCT imaging components, or the like. The imaging components will be positioned on the deployment catheter so that they may visualize both the target anatomical valve and the valve clip as the valve clip is being manipulated for implantation over the valve leaflets. In still further embodiments, the delivery system and/or the fixation device may contain radiopaque and/or echogenic mechanical indicators that change position when the leaflets are fully inserted thereby allowing the user to confirm the insertion of the leaflets by visualizing via conventional fluoroscopy or ultrasound imaging.

In still other embodiments of the systems of the present inventions, the steerable catheters will include mechanisms for selectively applying biasing forces to the outer and/or inner arms of the valve clip in order to open the arms in order to create the gap or space for receiving and capturing the valve leaflets. In the illustrated embodiments, a first set of tethers may be positioned on or through the delivery catheter and coupled to the outer arms so that the tethers may be tensioned to selectively bias the outer arms into a valve leaflet capture position. 281. Both sets of tethers will typically be further configured to selectively unbias the outer arms and the inner arms either individually or simultaneously so that the outer and inner arms are allowed to self-close toward and over the valve leaflets in order to immobilize the leaflets for treatment of any of the conditions described herein and above.

In a third specific aspect, the present invention provides methods for clipping an anatomical valve to immobilize the leaflets of that valve for treating a variety of conditions. For example, the leaflets of a mitral valve may be clipped in order to treat mitral valve regurgitation. In another example, the leaflets of a venous valve may be clipped in order to treat venous insufficiency.

The methods of the present invention comprise advancing a valve clip having a pair of outer arms and a pair of inner arms to a location adjacent to the target anatomical valve. At least one of (1) the pair of outer arms and (2) the pair of inner arms is biased to open a valve leaflets capture space or gap between adjacent outer and inner arms. The valve clip is then positioned so that one valve leaflet is located or captured in the gap or space between the left outer and inner arms another valve leaflet is positioned in the gap or space between the right outer and inner arms. The valve leaflets may then be immobilized by releasing a biasing force or tension on the at least one pair of outer or inner arms to that the left outer and inner arms and the right outer and inner arms self-close over the valve leaflets, thus securing the leaflets together.

In particular embodiments of the methods of the present invention, both the pair of outer arms and the pair of inner arms will be initially biased in order to effect opening of the valve leaflet capture gaps or spaces therebetween. Biasing is typically accomplished by drawing on tethers attached to at least one of the pair of outer and inner arms, typically with separate tether structures attached to each pair of outer and inner arms. The tethers may be tensioned in order to bias the outer and inner arms so that they move away from each other to create the valve leaflet capture gap or space therebetween. After the outer and inner arms have been biased open and the valve leaflets captured, tension on the tethers may be released so that the outer and inner arms self-close over the valve leaflets.

As an alternative to the use of tethers, biasing may comprise advancing a pair of posts or other engagement members against at least one pair of the outer and inner arms. The posts may engage at least the two lower arms or at least the two upper arms to selectively open the lower and upper arms into a valve leaflet capture position. In some instances, the posts may engage an upper surface of each outer arm such that advancing the posts in an inferior direction opens the outer arms relative to the inner arms. The inner arms may optionally be configured to remain stationary as the posts are advanced. In other instances, the posts may engage a lower surface of each inner arm such that advancing the posts in a superior direction opens the inner arms relative to the outer arms. The outer arms may optionally be configured to remain stationary as the posts are advanced.

In other embodiments of the methods herein, positioning the valve clip comprises manipulating a delivery catheter where the valve clip is releasably attached to a distal end of the delivery catheter. Positioning may further comprise observing the anatomical valve and the valve clip by observing the mechanical valve position indicators (as described above) and/or using an imaging component on the delivery catheter as the valve clip is being positioned.

A particular advantage of this invention is multiple sizes and shapes of the fixation device. The fixation device can be configured attach to a small section of the leaflet (the where the leaflets coapt together form a parallel seal) or in a preferred embodiment, a larger section that includes the parallel coapted section as well as curved contoured section of the leaflets. Longer and contoured arms allow for easier capture of the leaflets.

Another particular advantage of this invention is that the fixation device is lock-less, by using super-elastic and sufficiently flexible inner and outer arms.

Another particular advantage of this invention is that the fixation device is made of sufficiently flexible inner and outer arms that grasp the tissue securely yet atraumatically while allowing for sufficient dynamic movement of the leaflets under physiological forces.

Another particular advantage of this invention is that inner and outer arms' frictional elements are recessed and barricaded on the sides, which mitigates risk of entanglement with chordae, tissue or delivery system.

Another particular advantage of this invention includes modular manufacturing and/or assembly of both outer and inner arms. Various shapes and sizes of inner and outer arm combinations can be interchangeably manufactured and/or assembled in a modular manner, to suit patient/user clinical treatment needs. For example, one side of the inner and outer arms may be longer to grasp larger anterior mitral valve leaflet, while a shorter inner and outer arm combination maybe used to grasp shorter posterior mitral valve leaflet.

Another particular advantage of this invention is elimination of large and increased movements of the fixation device during bailout, such as the inversion of the leaflet grasping arms. This is achieved by use of sutures, strings, or wires to lift the leaflets away from the grasping arms. In alternate embodiments that enable inversion of the arms, it is done so by simply flexing the arms furthermore.

Another particular advantage of this invention is the relatively simple and compact size of the fixation device. This allows the use of smaller diameter catheters, thus making deployment less traumatic to the patient. For example, MitraClip® device uses a 24 Fr outer diameter guide catheter. In a preferred embodiment, the current invention uses a 12 Fr guide catheter.

Another particular advantage of this invention is compatibility with commercially available transseptal introducer sheath. This is achieved by making the delivery device compatible with standard commercially available fixed or steerable transseptal introducer sheaths. Some examples of commercial introducer sheaths sizes include and not limited to: 7 Fr, 7.5 Fr, 8 Fr, 8.5 Fr, 9 Fr, 9.5 Fr, 10 Fr, 10.5 Fr, 11 Fr, 11.5 Fr and 12 Fr internal diameters. Some examples (and not limited to these examples) of commercially available introducers are: HeartSpan Fixed Curve Braided Transseptal Sheath and HeartSpan Steerable Sheath Introducer by Merit Medical Systems, Inc. UT; DIREX™ and Zurpaz™ Steerable Sheath by Boston Scientific Corporation, MA and; Agilis NxT™ by St. Jude Medical, MN; and Composer® Deflectable Catheter Handle Platform, Freudenberg Medical Minimally Invasive Solutions, Inc., IN.

Another advantage of this invention is the potential of performing the procedure under local anesthesia, thus eliminating the risks of general anesthesia. This is achieved by incorporating visualization techniques within or in conjunction with the delivery catheter system that replace the need for transesophageal echocardiography (TEE).

Other objects and advantages of the present invention will become apparent from the detailed description to follow, together with the accompanying drawings.

A particular advantage of this invention is that the atraumatic frictional elements (barbs) are placed medially along the long axis of the arm body and confined by continuous and solid side surface. Unlike in the MitraClip® device, the barbs are not exposed along the sides. This is advantageous as it significantly reduces the risk of entanglement of chordae tendineae, valve leaflets and other tissues with which devices may become entangled. Further, this feature reduces the risk of entanglement or sutures or wires or other such delivery catheter elements that may potentially come in contact with the fixation device.

In an exemplary variation to the above, the frictional elements (barbs) are placed medially along the long axis of the arm body and or towards lateral sides, however, the barbs may be protected or confined by staggered or continuous wire or spring like members that provide a barrier to prevent tissue to chordae or sutures from getting untangled with the barbs.

In an exemplary variation to the above, the frictional elements (barbs) are placed medially along the long axis of the arm body and or lateral sides, however, below or above the barbs may be wires, flat-tube, balloon or other mechanisms that can eject an entangled tissue, chordae, suture etc. on demand. For example (and not limited to this example), flat-tube balloon may be placed along the barbs. When deflated, the barbs protrude and can grasp tissue or leaflets as designed. However, on inflating, the flat-tube balloon extends beyond the barbs, thus ejecting the captured tissue or chordae or suture.

The atraumatic advantage comes from the design that resists complete penetration of the barb within the tissue, thus reducing the risk of tissue perforations. In one preferred embodiment, the length of the barb is about 1 mm and the tip of the barb has a v-shaped tooth that is 0.25 mm deep. In another preferred embodiment, the length of the barb is about 1.5 mm and the v-shaped teeth depth is about 0.25 mm. Therefore, in both exemplary embodiments, the depth of tissue penetration is about 0.25 mm in general, which is much less than the typical thickness of the mitral valve leaflets. Additionally, the v-shaped teeth are sufficiently blunt, while providing the required gripping friction. Although, a v-shaped tooth was used as an example, any such tissue penetration design obvious to those skilled in art, may be used.

Another advantage of this invention is the ability to deploy a single pair of inner and outer arm comprising of a base with an adjustable tether that can be either left implanted temporarily or permanently or detached during or post deployment. Further, multiple such pairs can be deployed. In one exemplary embodiment, two such pairs are deployed, and their bases are pulled or cinched together using the adjustable tether, during or post deployment. The adjustable tethers can be left implanted temporarily or permanently. Alternatively, two or more adjustable tethers can be fixed distally (close to the device) and the proximal section detached. Any or all following exemplary methods may be used to fix the distal implanted segments of the adjustable tethers, such as locking in a tortuous polymer, gluing, bonding, welding, tying, knotting, crimping, clamping, squeezing.

An advantage of the above invention is to mitigate the mitral valve regurgitation by adjusting the tether using one, two, three or more pairs of devices. In one exemplary embodiment, a leaflet with broken chordae is grasped and the tether is used to stabilize the leaflet and/or mitigate regurgitation. In an alternate exemplary embodiment, two such pairs will be used to grasp each leaflet, and the tethers with be used to fully or partially coapt and/or approximate the leaflets creating an edge-to-edge repair, wherein, the extent of coaptation or approximation can be varied or progressively increased during or post deployment. In an alternate exemplary embodiment, two such pairs are used on the same leaflet to close a cleft, tear, and/or cinch to mitigate regurgitation. In an alternate exemplary embodiment, three such pairs are used, the first and second pair on the anterior leaflet to cinch and close a cleft and the third on the posterior leaflet to coapt with the first pair, to create an edge to edge Alfieri repair.

An alternate advantage of this invention as described above is to the two or more pair to tethered arms to grasp leaflets close to anulus and/or grasp anulus, wherein, the adjustable tethers can then be used to cinch the anulus laterally, circumferentially and/or radially to mitigate regurgitation.

An exemplary embodiment of above described invention of a tissue grabbing device with an adjustable tether comprises a set of issue grabbing elements such as leafsprings or clamps (for example c-clamps) or graspers (for example rat tooth graspers) that comprise of sheet metal components, single or multiple loops of wires, tubes with stent like patterns, machined components, molded metals or polymers or ceramics, active or passive sensors and transducers, coatings and/or fabric covering, a base, and an adjustable tether. One exemplary method of deploying such device in a valve comprises of deploying a first set of leaflets grabbing elements, deploying a second set of leaflets grabbing elements adjustably connected to first leaflet grabbing elements, adjusting the distance between the two elements to mitigate valve regurgitation.

In alternate methods, the present invention further comprises adjusting the distance between the two sets of leaflets grabbing elements of the tissue grabbing device before insertion in the heart and deploying the first and second elements sequentially.

In an alternate method for the above invention with tissue grabbing device, deploying a first leaflet grabbing elements connected to a tether, sliding the second leaflet grabbing pair along/over the tether, deploying the second leaflet grabbing elements onto the leaflet and onto the tether, cinching the wire to adjust the space between the two leaflet grabbing pairs during or post procedure and fixing the space in between the two leaflet grabbing elements and detaching and removing the excess tether during or post procedure.

The following numbered clauses describe other examples, aspects, and embodiments of the inventions described herein:

1. A tissue grasping device comprising: a hub configured to be removably attached to a deployment shaft; a first pair of tissue grasping arms comprising a first inner arm and a first outer arm coupled to the hub; and a second pair of tissue grasping arms comprising a second inner arm and a second outer arm coupled to the hub; wherein each pair of outer and inner arms are configured to be biased apart to create a tissue capture space therebetween and to resiliently self-close over the tissue when unbiased after the tissue has been captured/grasped.

2. A valve repair leaflet grasping device comprising: a hub configured to be removably attached to a deployment shaft; a first pair of leaflet capture arms comprising a first inner arm and a first outer arm coupled to the hub; and a second pair of leaflet capture arms comprising a second inner arm and a second outer arm coupled to the hub; wherein each pair of the outer and inner arms are configured to be biased apart to create a leaflet capture space therebetween and to resiliently self-close over the leaflet when unbiased after the leaflet has been captured.

3. A valve repair leaflet grasping device comprising: a hub configured to be removably attached to a deployment shaft; a first pair of leaflet capture arms comprising a first inner arm and a first outer arm coupled to the hub; and a second pair of leaflet capture arms comprising a second inner arm and a second outer arm coupled to the hub; and a third pair of leaflet capture arms comprising a third inner arm and a third outer arm coupled to the hub; wherein each pair of outer and inner arms are configured to be biased apart to create a leaflet capture space therebetween and to resiliently self-close over the leaflet when unbiased after the leaflet has been captured.

4. A tissue grasping device comprising: a hub configured to be removably attached to a deployment shaft; the deployment shaft comprising of a pair of inverters, release rod, actuations sutures and multiple slots; and a first pair of tissue grasping arms comprising a first inner arm and a first outer arm coupled to the hub; and a second pair of tissue grasping arms comprising a second inner arm and a second outer arm coupled to the hub; wherein each pair of outer and inner arms are individually configured to be biased apart to create a tissue capture space therebetween using actuation sutures; and to resiliently self-close sequentially or simultaneously over the tissue when unbiased after the tissue has been captured/grasped/stabilized in the tissue capture space; wherein, the inner arm actuation sutures being removably looped through one or more slots and the release rod passing through the slots and configured to lift/raise the inner arm off the tissue; the outer arm actuation sutures being removably looped through the inverter and through one or more slots; configured to create tissue grasping space and/or to invert the arms to enable bailout; and to deploy the device after the tissue capture and on removal of the release rod from the deployment shaft.

5. A valve repair leaflet grasping device comprising: a hub configured to be removably attached to a deployment shaft; the deployment shaft comprising of a pair of inverters, release rod, actuations sutures and multiple slots; and a first pair of leaflet grasping arms comprising a first inner arm and a first outer arm coupled to the hub; and a second pair of leaflet grasping arms comprising a second inner arm and a second outer arm coupled to the hub; wherein each pair of outer and inner arms are individually configured to be biased apart to create a leaflet capture space therebetween using actuation sutures; and to resiliently self-close over the leaflet when unbiased sequentially or simultaneously using the actuation sutures after the leaflet has been captured in the leaflet capture space; wherein, the inner arm actuation sutures being removably looped through one or more slots and the release rod passing through the slots and configured to lift/raise the inner arm off the tissue; the outer arm actuation sutures being removably looped through the inverter and through one or more slots; configured to create tissue grasping space and/or to invert the arms to enable bailout; and to deploy the device after leaflet capture on removal of the release rod from the deployment shaft.

6. A valve repair leaflet grasping device comprising: a hub configured to be removably attached to a deployment shaft; the deployment shaft comprising of a pair of inverters, release rod, actuations sutures and multiple slots; and a first pair of leaflet grasping arms comprising a first inner arm and a first outer arm coupled to the hub; and a second pair of leaflet grasping arms comprising a second inner arm and a second outer arm coupled to the hub; and a third pair of leaflet grasping arms comprising a third inner arm and a third outer arm coupled to the hub; wherein each pair of outer and inner arms are individually configured to be biased apart to create a leaflet capture space therebetween using actuation sutures; and to resiliently self-close sequentially or simultaneously over the leaflet when unbiased after the leaflet has been captured/grasped/stabilized in the leaflet capture space; wherein, the inner arm actuation sutures being removably looped through one or more slots and the release rod passing through the slots and configured to lift/raise the inner arm off the tissue; the outer arm actuation sutures being removably looped through the inverter and through one or more slots; configured to create tissue grasping space and/or to invert the arms to enable bailout; and to deploy the device after leaflet capture on removal of the release rod from the deployment shaft.

7. A repair device in clauses 1-6, wherein, the device is configured to enable edge-to-edge repair of mitral valve.

8. A repair device in clauses 1-6, wherein, the device is configured to enable edge-to-edge repair of tricuspid valve.

9. A repair device in clauses 1-6, wherein, the device is configured to enable edge-to-edge repair of a cleft leaflet in a mitral valve 10. A repair device in clauses 1-6, wherein, the device is configured to enable edge-to-edge repair of a cleft leaflet in a tricuspid valve.

11. A tissue grasping device comprising: at least a pair of arms that are configured to resiliently flex towards each other; a hub; and an adjustable tether; wherein at least one arm has tissue grasping elements and each of the arm is connected at one end to the hub; and the hub is configured to be detachably connected to the delivery device; and the adjustable tether is configured to be temporarily or permanently implantable; and the free ends of the arms are configured to be biased using the delivery system to create a tissue capture space therebetween and to resiliently self-close over the tissue when unbiased after the tissue has been captured; and the adjustable tether is used to coapt or approximate or cinch the tissue.

12. A method of repairing a mitral valve, comprising deploying at least two pairs of tissue grasping devices as in clause 11, wherein, the first pair of device is used to grasp the edge of anterior leaflet; the second pair of the device is used to grasp the edge of the posterior leaflet; using the adjustable tether for cinching and/or apposing the two devices to coapt the leaflets; creating an Alfieri edge-to-edge repair.

13. A method of repairing a tricuspid valve, comprising deploying at least three pairs of tissue grasping devices as in clause 11, wherein, the first pair of device is used to grasp the edge of first leaflet; the second pair of the device is used to grasp the edge of the second leaflet; the third pair of the device is used to grasp the edge of the third leaflet; using the adjustable tether for cinching and/or apposing the two devices to coapt the leaflets; creating an Alfieri edge-to-edge repair.

14. A method of repairing a valve, comprising deploying at least two pairs of tissue grasping devices as in clause 11, wherein, the first pair of device is used to grasp the edge of a first leaflet; the second pair of the device is used to grasp the papillary muscle or chordae or ventricular tissue; using the adjustable tether for cinching and/or apposing the two devices to coapt the leaflets; creating a chordal repair.

15. A method of repairing a valve, comprising deploying at least two pairs of tissue grasping devices as in clause 11, wherein, the first pair of device is used to grasp the body of a first leaflet; the second pair of the device is used to grasp the body of a second leaflet; using the adjustable tether for cinching and/or apposing the two devices to coapt the leaflets; creating an annulus repair.

16. A method of repairing a valve, comprising deploying at least two pairs of tissue grasping devices as in clause 11, wherein, the first pair of device is used to grasp the annulus at one site; the second pair of the device is used to grasp the annulus at a second site; using the adjustable tether for cinching and/or apposing the two devices to coapt the leaflets; creating an annulus repair.

17. A method of repairing a valve, comprising deploying at least two pairs of tissue grasping devices as in clause 11, wherein, the first pair of device is used to grasp the body or edge of a leaflet; the second pair of the device is used to grasp the body or edge of the leaflet across the cleft; using the adjustable tether for cinching and/or apposing the two devices to coapt or appose the leaflets; creating a cleft repair.

18. A method of repairing a valve, comprising deploying at least two pairs of tissue grasping devices as in clause 11, wherein, the first pair of device is used to grasp the atrial or ventricular tissue at one site; the second pair of the device is used to grasp the atrial or ventricular tissue at a second site; using the adjustable tether for cinching and/or apposing the two devices.

19. A method of the repairing a mitral valve as in clauses 11-18, wherein: the tethers are temporarily implanted in the body to adjust the coaptation during the device implantation procedure; and removing excess tether to finalize the adjustment.

20. A method of repairing a mitral valve as in clauses 11-18, wherein: the tethers are temporarily implanted in the body after initial adjustment during the device implantation procedure; and performing at least a second procedure at a later time or date to make additional fine adjustment; and removing excess tether to finalize the adjustment.

21. A method of clauses 11-19, for removing excess tether after finalizing the adjustment using the delivery catheter or a second catheter specifically designed for fastening, trimming and removing the excess length.

22. A valve clip or method as in clauses 1-21, wherein the clip coapts the captured pair of leaflets or tissue.

23. A valve clip or method as in clauses 1-22, wherein, the clip coapts the captured pair of leaflets and also cinches the leaflets together.

24. A valve clip or method as in clauses 1-23, wherein, the clip cinches and/or coapts 100%, 90%, 80%, 70%, 60%, 50%, 40%, 30%, 20%, 10%, 5% and/or 0% of the captured segment of the leaflets 25. A valve clip or method as in clauses 1-24, wherein the final profile of the leaflets in the grasped region is essentially straight and/or curved.

26. A valve clip or method as in clauses 1-25, wherein the arms capture the leaflets along its anatomical curve, from the edge up to annulus or from the annulus to up to edge.

27. A valve clip or method as in clauses 1-26, wherein the implanted clip is 100%, 90%, 80%, 70%, 60%, 50%, 40%, 30%, 20%, 10%, 5% and/or 0% below and/or above the coaptation line.

28. A valve clip as in clauses 27, wherein the implanted clip is 100%, 90%, 80%, 70%, 60%, 50%, 40%, 30%, 20%, 10%, 5% and/or 0% within or below and/or above the zone of apposition.

29. A valve clip or method as in clauses 1-28, wherein the final position of the inner arms is essentially parallel and/or coapted.

30. A valve clip or method as in clauses 1-29, wherein the final position of the inner arms is partially parallel or coapted.

31. A valve clip or method as in clauses 1-30, wherein the final position of the inner arms is partially curved and point away from each other.

32. A valve clip or method as in clauses 1-28, wherein the final position of the outer arms is essentially parallel and/or coapted.

33. A valve clip or method as in clauses 1-29, wherein the final position of the outer arms is partially parallel or coapted.

34. A valve clip or method as in clauses 1-29, wherein the final position of the outer arms is partially curved and point away from each other.

35. A valve clip or method as in clauses 1-34, wherein both arms capture the same leaflet.

36. A valve clip or method as in clauses 1-35, wherein at least some of the leaflet capture arms are formed as a leaf spring or a cantilever.

37. A valve clip or method as in clauses 1-36, wherein at least some of the outer and inner arms are formed as a leaf spring or cantilever with a resilient base attached to the hub and a less-resilient valve-grasping element extending from the base.

38. A valve clip or method as in clauses 1-37, wherein each of the outer and inner arms is formed as a leaf spring or cantilever with a resilient base attached to the hub and a less, same, or more resilient valve-grasping element extending from the base.

39. A valve clip or method as in clauses 1-38, wherein each of the outer and inner arms is formed as a leaf spring or cantilever wherein: the outer arm is much more resilient than the inner arm.

40. A valve clip or method as in clauses 1-39, wherein each of the outer and inner arms is formed as a leaf spring or cantilever wherein: the outer arm is same or less resilient than the inner arm.

41. A valve clip or method as in clauses 1-40, wherein the arms have valve-grasping barbs or features that diverge from a common axis to form a V or W or tooth shaped and/or claw shaped.

42. A valve clip or method as in clauses 1-41, wherein the inner and/or outer arms have a C or S-shaped curve to separate superior surfaces of the inner arms from inferior surfaces of the outer arms, wherein such a separation accommodates the valve leaflets.

43. A valve clip or method as in clauses 1-41, wherein the valve-grasping elements are parallel or curved to a common axis when the outer and inner arms are unbiased.

44. A valve clip or method as in clauses 1-43, wherein the valve-grasping elements diverge from a common axis to form a curved shape that closely contours the native leaflet shape when the outer and inner arms are unbiased.

45. A valve clip or method as in clauses 1-44, wherein the inner and outer arm are configured to capture leaflets within coapting segments of the leaflets.

46. A valve clip or method as in clauses 1-45, wherein the inner and outer arm capture leaflets in the coapting segments and non-coapting segments of the leaflets.

47. A valve clip or method as in clauses 1-46, wherein the inner arm and outer arm are configured to capture leaflets in the coapting segments and non-coapting segments along the contours of the native leaflets as well as the annulus.

48. A valve clip or method as in clauses 1-47, wherein the inner and outer arms are configured to capture leaflets simultaneously.

49. A valve clip or method as in clauses 1-48, wherein the inner and outer arms are configured to capture leaflets sequentially.

50. A valve clip or method as in clauses 1-49, wherein the inner arm and outer arm are configured to capture leaflets independently.

51. A valve clip, tissue gripping device, or method of any of the clauses, wherein the thickness of the outer arm is same or greater than the inner arm.

52. A valve clip, tissue gripping device, or method of any of the clauses, wherein the thickness of the outer arm is same or less than the inner arm.

53. A valve clip, tissue gripping device, or method of any of the clauses, wherein the thickness of the outer arm is >0.0055" and is preferably between 0.008" and 0.020"; and is preferably 0.010", 0.012", or 0.014"

54. A valve clip, tissue gripping device, or method of any of the clauses, wherein the thickness of the inner arm is >0.0055" and is preferably between 0.007" and 0.090"; and is preferably 0.008", 0.009", or 0.010"

55. A valve clip or tissue gripping device of any of the clauses, wherein the thickness of the inner arm is >0.0055" and is preferably between 0.007" and 0.090"; and is preferably 0.008", 0.009", or 0.010"

56. A valve clip, tissue gripping device, or method of any of the clauses, wherein each arm can be actuated or moved independently.

57. A valve clip, tissue gripping device, or method of any of the clauses, comprising more than one pair of arms.

58. A valve clip, tissue gripping device, or method of any of the clauses, comprising two pairs of arms that are configured to grab anterior and/or posterior leaflets of a mitral valve.

59. A valve clip, tissue gripping device, or method of any of the clauses, comprising more than one pairs of arms that are configured to grab the same valve leaflet or tissue.

60. A valve clip, tissue gripping device, or method of any of the clauses, comprising three pairs of arms that are configured to grab the three leaflets of a tricuspid valve.

61. A valve clip, tissue gripping device, or method of any of the clauses, wherein each pair is configured relative to the other pair, so as to reduce regurgitation between the captured tissues.

62. A valve clip, tissue gripping device, or method of any of the clauses, wherein each pair is configured with to exhibit resilient bias towards with the other pair, so as to reduce regurgitation between the captured tissues.

63. A valve clip, tissue gripping device, or method of any of the clauses, wherein each pair is formed of arms having same or varying thickness, size, length, shape, resilience and/or bias force (acute or chronic).

64. A valve clip, tissue gripping device, or method of any of the clauses, wherein each pair is having same or varying thickness, size, length, shape, resilience and/or bias force (acute or chronic).

65. A valve clip, tissue gripping device, or method of any of the clauses, wherein the arms comprise of shape-memory material.

66. A valve clip, tissue gripping device, or method of any of the clauses, wherein the shape-memory material is comprised of one or more of a shape-memory alloy or shape-memory polymer.

67. A valve clip, tissue gripping device, or method of any of the clauses, wherein the shape-memory material is a shape-memory alloy selected from the group consisting of: copper-zinc-aluminum; copper-aluminum-nickel; nickel-titanium; nickel-titanium platinum; and nickel-titanium palladium alloys.

68. A valve clip, tissue gripping device, or method of any of the clauses, wherein the shape-memory material is a nickel titanium alloy.

69. A valve clip, tissue gripping device, or method of any of the clauses, wherein the shape-memory material is a shape-memory polymer selected from the group consisting of: oligo(e-caprolactone)diol, oligo(p-dioxanone)diol, polynorborene, polyisoprene, styrene butadiene, polyurethane-based materials, and vinyl acetate-polyester-based compounds.

70. A valve clip, tissue gripping device, or method of any of the clauses, wherein each pair of arms are configured to capture a leaflet or tissue.

71. A valve clip, tissue gripping device, or method of any of the clauses, wherein each pair captures leaflets from both atrial and ventricular sides.

72. A valve clip, tissue gripping device, or method of any of the clauses, wherein said device is configured such that upon being positioned in a deployed state against a leaflet of the mitral valve, an arm of the tissue gripping device exerts a force (acute and/or chronic) of about 0.06 to about 0.10 pounds against the leaflet.

73. A valve clip, tissue gripping device, or method of any of the clauses, wherein said device is configured such that upon being positioned in a deployed state against a leaflet of the mitral valve, an arm of the tissue gripping device exerts a force (acute and/or chronic) of about 0.001 to about 0.06 pounds against the leaflet.

74. A valve clip, tissue gripping device, or method of any of the clauses, wherein said device is configured such that upon being positioned in a deployed state against a leaflet of the mitral valve, an arm of the tissue gripping device exerts a force (acute and/or chronic) of about 0.1 to about 1.0 pounds against the leaflet.

75. A valve clip, tissue gripping device, or method of any of the clauses, wherein said device is configured such that upon being positioned in a deployed state against a leaflet of the mitral valve, an arm of the tissue gripping device exerts a force (acute and/or chronic) of about 0.10 to about 5 pounds against the leaflet.

76. A valve clip, tissue gripping device, or method of any of the clauses, wherein said device is configured such that upon being positioned in a deployed state against a leaflet of the mitral valve, an arm of the tissue gripping device exerts a force (acute and/or chronic) of about 0.10 to about 50 pounds against the leaflet.

77. A valve clip, tissue gripping device, or method of any of the clauses, wherein said device is configured such that upon being positioned in a deployed state against a leaflet of the mitral valve, an arm of the tissue gripping device exerts a net force (acute and/or chronic) of about 0.15 to about 100 pounds against the leaflet.

78. A valve clip, tissue gripping device, or method of any of the clauses, wherein said device is configured such that upon being positioned in a deployed state against a leaflet of the mitral valve, a pair of outer arms (for example, as in FIGS. 110-112); or two pairs of arms (for example, as in FIGS. 4-9), the outer arms exert a coapting force (acute and/or chronic) between 0.01 to 100 pounds, or preferably about 0.03 to 10.0 pounds, or preferably about 0.1 to 5.0 pounds, or preferably about 0.2 to 2.0 pounds, against the leaflet.

79. A valve clip, tissue gripping device, or method of any of the clauses, wherein the said arm of the tissue gripping device of a given pair, upon moving from a pre-deployed configuration to a deployed configuration, deploy to engage the valve tissue against the tissue engagement surfaces of the other arm of the pair elements, while the other arm is either stationary or moving.

80. A valve clip, tissue gripping device, or method of any of the clauses, wherein a pair of arms grips the tissue 100% of its length.

81. The tissue gripping device of any of the clauses, wherein a pair of arms grips the tissue about 100% to 80% of its length.

82. A valve clip, tissue gripping device, or method of any of the clauses, wherein a pair of arms grips the tissue about 100% to 50% of its length.

83. A valve clip, tissue gripping device, or method of any of the clauses, wherein a pair of arms grips the tissue about 75% to 20% of its length.

84. A valve clip, tissue gripping device, or method of any of the clauses, wherein a pair of arms grips the tissue about 100% to 0.01% of its length.

85. A valve clip, tissue gripping device, or method of any of the clauses, wherein a pair of arms grips the tissue about 20% to 1% of its length.

86. A valve clip, tissue gripping device, or method of any of the clauses, wherein said shape-memory alloy or shape-memory polymer has a transformation temperature of between about −15 to about 37 degrees C., preferably between −5 to about 27 degrees C.

87. A valve clip, tissue gripping device, or method of any of the clauses, wherein said shape-memory alloy or shape-memory polymer has a transformation temperature of between −5 to about 10 degrees C.

88. A valve clip, tissue gripping device, or method of any of the clauses, wherein said shape-memory alloy or shape-memory polymer has a transformation temperature of between 10 to about 27 degrees C.

89. A method of manufacturing a tissue gripping device of any of the clauses, the method comprising: cutting one or more structural features from a strip of sheet stock material of a shape-memory alloy, the one or more structural features including a plurality of slotted recesses disposed at one or more side edges of the stock material; barrier and heat shape setting one or more bend features into stock material.

90. A method of manufacturing a tissue gripping device of any of the clauses, the method comprising: cutting one or more structural features from a strip of sheet stock material of a shape-memory alloy, the one or more structural features including a plurality of slotted recesses disposed at medially or centrally or within the stock material; and heat shape setting one or more bend features into stock material.

91. A method of manufacturing a tissue gripping device of any of the clauses, the method comprising: forming and/or joining individual strands or loops of wire material of a shape-memory alloy, and heat shape setting one or more bend features into stock material.

92. A method of manufacturing a tissue gripping device of any of the clauses, the method comprising: forming and/or joining individual strands or loops of wire material of a shape-memory alloy, and heat shape setting one or more bend features into stock material, and forming smaller loops at the tip for passage of sutures.

93. A method of manufacturing a tissue gripping device of any of the clauses, the method comprising: forming and/or joining individual strands or loops of wire material of a shape-memory alloy, and heat shape setting one or more bend features into stock material, adding bands, crimps, barbs and/or frictional elements of the same or different material.

94. The method of any of clauses 89-93, wherein one or more features includes a frictional element formed by heat shape setting one or more portions of the stock material slotted recess as a protruding barb.

95. The method of any of clauses 89-94, wherein one or more features includes a frictional element or barbs formed by crimping or adding a band or additional material to the arms as a protruding barb.

96. The method of any of clauses 89-95 for making tissue grasping device, wherein the frictional elements comprise inherent or extraneous side barrier features that prevent entanglement of chordae or other device elements.

97. The method of any of clauses 89-96 for making tissue grasping device, wherein the frictional elements comprise inherent side barrier features by forming them medially or away from the edges.

98. The method of any of clauses 89-97 for making tissue grasping device, wherein the frictional elements comprise extraneous side barrier features by plugging or covering the slotted recesses or running a wire or continuous structure along the sides, configured to prevent or mitigate entanglement of tissue or device features with the frictional elements.

99. The method of any of clauses 89-98, further comprising, after obtaining the stock material, subtracting an amount of the stock material using a subtractive process.

100. The method of any of clauses 89-99, further comprising, after obtaining the stock material, subtracting an amount of the stock material using a subtractive process for example and not limited to these examples: wire EDM, laser cutting and machining, swiss machining, water-jet cutting, traditional machining.

101. A method of manufacturing a tissue gripping device of any of the clauses, the method comprising: an additive process of the components, preferably using metal 3D printing.

102. A method of manufacturing a tissue gripping device of any of the clauses, the method comprising: molding process of the components, preferably metal powder compression molding.

103. A method of manufacturing a tissue gripping device of any of the clauses, further comprising, heat-shape setting, finishing the valve repair device by one or more mechanical deburring, grinding, machining, particulate blasting, electropolishing, cleaning, and/or passivating.

104. A method of manufacturing a tissue gripping device of any of the clauses, comprising coating and/or covering to improve biocompatibility and/or device tissue 105. A valve clip, tissue gripping device, or method of any of the clauses, wherein the length of arm interfacing with the tissue/leaflet is greater than 0.1 mm, preferably 9 mm, 12 mm, 15 mm, 20 mm, 25 mm, 30 mm, 35 mm, 40 mm, 50 mm and/or 100 mm.

106. A valve clip, tissue gripping device, or method of any of the clauses, wherein the length tissue/leaflet captured by a pair of arms is greater than 0.1 mm, preferably 9 mm, 12 mm, 15 mm, 20 mm, 25 mm, 30 mm, 35 mm, 40 mm, 50 mm and/or 100 mm.

107. A valve clip, tissue gripping device, or method of any of the clauses, wherein a single arm is split to form outer and inner arms.

108. A valve clip, tissue gripping device, or method of any of the clauses, wherein a pair of inner arms or a pair of outer arms or a pair of inner and outer arms is formed out of a single continuous sheet or wire loop.

109. A valve clip, tissue gripping device, or method of any of the clauses, wherein each pair of inner and outer arms are configured to have different tissue/leaflet engaging length; and in one preferred configuration, one pair is 9 mm long and the other is 12 mm long; and in another preferred configuration, one pair is 10 mm long and other is 15 mm long; and in another preferred configuration, one pair is 20 mm long and other is 30 mm long.

110. A valve clip, tissue gripping device, or method of any of the clauses, wherein each pair of inner and outer arms are configured to have different tissue/leaflet engaging shape; and in one preferred configuration, one pair is essentially straight (primarily to grasp tissue at or below the zone of coaptation) while other pair is curved (primarily to grasp tissue above the zone of coaptation); and in one preferred configuration, the straight section is 3 mm and curved section is 6 mm in first pair and in second pair straight section is 3 mm and curved section is 12 mm).

111. A valve clip, tissue gripping device, or method of any of the clauses, wherein the arms have valve-grasping barbs or features encased by side barriers and diverge from a common axis, that protrudes <10 mm deep, <100 mm wide, and <100 mm in length, preferably about 0.7 mm deep, about 0.7 mm wide and about 1.5 mm long.

112. A valve clip, tissue gripping device, or method of any of the clauses, wherein the arms have valve-grasping barbs or features formed by plurality of slots within the body and away from sides and diverge from a common axis, that protrudes <10 mm deep, <100 mm wide, and <100 mm in length, preferably about 0.7 mm deep, about 0.7 mm wide and about 1.5 mm long.

113. A valve clip, tissue gripping device, or method of any of the clauses, wherein the arms have valve-grasping claw like features at the free end of the arm.

114. A valve clip, tissue gripping device, or method of any of the clauses, wherein the arms have valve-grasping claw like features at the free end of the arm that may have tissue penetration limiting features; wherein, the penetration limiting depth is <0.01%, <1%, <10%, <20%, <30%, <40%, <50%, <60%, <70%, <80%, <90%, and/or <100% of the length of the arm.

115. A valve clip, tissue gripping device, or method of any of the clauses, wherein the arms have valve-grasping barbs or features formed by plurality of slots within the body and away from sides and are bend about 10 to 160 degrees, preferably about 60 degrees.

116. A valve clip, tissue gripping device, or method of any of the clauses, wherein the arms have valve-grasping barbs or features formed by plurality of slots within the body and away from sides and have a tissue penetration limiting feature at the tip of the barb (for example a t, v or w shaped tooth or claw), wherein the penetration limiting depth is <0.01%, <1%, <10%, <20%, <30%, <40%, <50%, <60%, <70%, <80%, <90%, and/or <100% of the length of the barb.

117. A valve clip, tissue gripping device, or method of any of the clauses, wherein the device is detachably coupled to the delivery system; and the device is loaded from the front, with the delivery system along the back of the device at an off-set from the central longitudinal axis of the catheter shaft.

118. A valve clip, tissue gripping device, or method of any of the clauses configured to have: asymmetric leaflet coaptation length and or; symmetric leaflet engaging width and or; expanding structure along the device that increases the leaflet contact surface area of the device and or; a tissue grasping structure that has side barriers to prevent unintended entanglement.

119. An endovascular heart valve repair device comprising: an elongate flexible guide shaft having a proximal end, a distal end, and a main lumen therebetween, the elongate flexible shaft being adaptable for positioning through a blood vessel into a chamber of the heart; a delivery catheter adaptable to be passed through the guide catheter lumen, having a flexible distal segment, a proximal segment, and a main segment therebetween, and the distal segment that is configured to be resiliently straight when extended out in the chamber of the heart un-supported, and the distal end of the delivery catheter having a release bar for mounting the device; a valve repair leaflet grasping device comprising: a hub configured to be removably attached to the release bar; a first pair of leaflet capture arms comprising a first inner arm and a first outer arm coupled to the hub; and a second pair of leaflet capture arms comprising a second inner arm and a second outer arm coupled to the hub; wherein each pair of the outer and inner arms are configured to be biased apart to create a leaflet capture space therebetween and to resiliently self-close over the leaflet when unbiased after the leaflet has been captured.

120. An endovascular heart valve repair device comprising: an elongate flexible guide shaft having a proximal end, a distal end, and a main lumen therebetween, the distal end comprising of at least a primary and a secondary multidirectional steerable segments, and the guide shaft being adaptable for positioning through a blood vessel into a chamber of the heart; a delivery catheter adaptable to be passed through the guide catheter lumen, having a flexible distal segment, a proximal segment, and a main segment therebetween, and the distal segment that is configured to be resiliently straight when extended out in the chamber of the heart un-supported, and the distal end of the delivery catheter having a release bar for mounting the device; the release bar comprising of a pair of inverters, release rod, actuations sutures and multiple slots; a valve repair leaflet grasping device comprising: a hub configured to be removably attached to the release bar; and a first pair of leaflet grasping arms comprising a first inner arm and a first outer arm coupled to the hub; and a second pair of leaflet grasping arms comprising a second inner arm and a second outer arm coupled to the hub; wherein each pair of outer and inner arms are individually configured to be biased apart to create a leaflet capture space therebetween using actuation sutures; and to resiliently self-close over the leaflet when unbiased sequentially or simultaneously using the actuation sutures after the leaflet has been captured, grasped and/or stabilized in the leaflet capture space; wherein the inner arm actuation sutures being removably looped through one or more slots and the release rod passing through the slots of the release bar and configured to lift/raise the inner arm off the tissue; the outer arm actuation sutures being removably looped through the inverter and through one or more slots; configured to create tissue grasping space and/or to invert the arms to enable bailout; and to deploy the device after leaflet capture on removal of the release rod from the release bar.

121. An endovascular heart valve repair device comprising: an first elongate flexible guide shaft having a proximal end, a distal end, and a main lumen therebetween, the distal end comprising of at least a (primary) multidirectional steerable segment, a second elongate flexible guide shaft adaptable to be passed through the first guide lumen, having a proximal end, a distal end, and a main lumen therebetween, the distal end comprising of at least a (secondary) multidirectional steerable segments, and the first and second guide shaft being adaptable for positioning through a blood vessel into a chamber of the heart; a delivery catheter adaptable to be passed through the guide catheter lumen, having a flexible distal segment, a proximal segment, and a main segment therebetween, and the distal segment that is configured to be resiliently straight when extended out in the chamber of the heart un-supported, and the distal end of the delivery catheter having a release bar for mounting the device; the release bar comprising of a pair of inverters, release rod, actuations sutures and multiple slots; a valve repair leaflet grasping device comprising: a hub configured to be removably attached to the release bar; and a first pair of leaflet grasping arms comprising a first inner arm and a first outer arm coupled to the hub; and a second pair of leaflet grasping arms comprising a second inner arm and a second outer arm coupled to the hub; wherein each pair of outer and inner arms are individually configured to be biased apart to create a leaflet capture space therebetween using actuation sutures; and to resiliently self-close over the leaflet when unbiased sequentially or simultaneously using the actuation sutures after the leaflet has been captured, grasped and/or stabilized in the leaflet capture space; wherein, the inner arm actuation sutures being removably looped through one or more slots and the release rod passing through the slots of the release bar and configured to lift/raise the inner arm off the tissue; the outer arm actuation sutures being removably looped through the inverter and through one or more slots; configured to create tissue grasping space and/or to invert the arms to enable bailout; and to deploy the device after leaflet capture on removal of the release rod from the release bar.

122. A valve clip, tissue gripping device, or method of any of the clauses, wherein, the delivery catheter is further adapted to comprise an exchangeable cartridge and a cartridge receiving feature; wherein, a plurality of cartridges comprising a valve repair device of selectable size and/or shape are configured to be detachably connectable to the delivery catheter, to deliver at least one device.

123. A valve clip, tissue gripping device, or method of any of the clauses, comprising a distal segment, a proximal segment, a main segment therebetween, and the distal segment of delivery catheter adapted to comprise an exchangeable cartridge and a cartridge receiving feature; wherein, a plurality of cartridges comprising a valve repair device of a selectable size and/or shape and a portion of the distal segment of the catheter is detachably connectable to the cartridge receiving feature of the remaining distal segment of the delivery catheter.

124. A valve clip, tissue gripping device, or method of any of the clauses, comprising a distal segment, a proximal segment, a main segment therebetween, and the main segment of delivery catheter adapted to comprise an exchangeable cartridge and a cartridge receiving feature; wherein, a plurality of cartridges comprising a valve repair device of a selectable size and/or shape and the entire distal segment and a portion of the main segment of the catheter, is detachably connectable to the cartridge receiving feature of the remaining main segment of the delivery catheter.

125. A valve clip, tissue gripping device, or method of any of the clauses, comprising a distal segment, a proximal segment, a main segment therebetween, and the proximal segment of delivery catheter adapted to comprise an exchangeable cartridge and a cartridge receiving feature; wherein a plurality of cartridges comprising a valve repair device of a selectable size and/or shape and the entire distal segment, main segment and a portion of the proximal segment of the catheter, is detachably connectable to the cartridge receiving feature of the remaining proximal end of the delivery catheter.

126. A valve clip, tissue gripping device, or method of any of the clauses, comprising a detachably connectable cartridge distal segment, a proximal segment, a main segment therebetween, and a handle with a distal cartridge receiving feature, and the end of the proximal segment of delivery catheter adapted to comprise an exchangeable cartridge; wherein a plurality of cartridges comprising a valve repair device of a selectable size and/or shape and the distal segment, the main segment and the proximal segment of the catheter is detachably connectable to the cartridge receiving feature of delivery catheter handle.

127. A valve clip or tissue grasping device delivery system as in any of the clauses, wherein the actuation suture comprises polymer-based sutures, metal wires, monofilament or multistrand ropes.

128. A valve clip, tissue gripping device, or method of any of the clauses, wherein the actuation suture comprises the ability to apply tension or pull force.

129. A valve clip, tissue gripping device, or method of any of the clauses, wherein the actuation suture comprises sufficient structural strength to apply both tension (or pull force) and compression (or push force).

130. A valve clip, tissue gripping device, or method of any of the clauses, wherein the actuation suture comprises a pull-push wire segment and a pull only wire/suture segment.

131. A delivery catheter as in any of the clauses, comprising a motorized handle, wherein the handle comprises at least a sensor, a transducer, a circuit, a power source, a switch, a motor, an actuator, and/or an audio/video display interface, to enable direct or remote deployment of the device.

132. A guide catheter as in any of the clauses, comprising a motorized handle, wherein, the handle comprises at least a sensor, a transducer, a circuit, a power source, a switch, a motor, an actuator, and/or an audio/video display interface, to enable direct or remote deployment of the device.

133. A valve clip or tissue grasping device delivery system as in any of the clauses, adaptable to deliver the valve repair device to any of the chambers of the heart, a heart structure and/or a valve.

134. A valve clip or tissue grasping device delivery system as in any of the clauses, adaptable to deliver the valve repair device to any of the chambers of the heart, a heart structure and/or a valve, via antegrade or retrograde approach, and percutaneous or transcutaneous approach, interventional or endoscopic or minimally invasive approach.

135. A valve clip, tissue gripping device, or method of any of the clauses, configured to have a balloon or an expandable member, to resist accidental retraction of the catheter.

136. A valve clip, tissue gripping device, or method of any of the clauses, configured to have a balloon or an expandable member and/or a deployable encasing feature, to assist in atraumatic advancement or retrieval of the device.

137. A valve clip, tissue gripping device, or method of any of the clauses, configured to have a balloon or an expandable member and/or a deployable encasing feature, to assist in atraumatic advancement or retrieval of the device.

138. A valve clip, tissue gripping device, or method of any of the clauses, configured to enable cardiographic imaging, physiological measurements and/or robotic device delivery.

139. A valve clip or tissue grasping device delivery system as in any of the clauses, wherein any of the exemplary embodiments and examples described in the above clauses or in this application, some or all can be made retrievable using known device retrievable methods, including some of the techniques described in this application.

140. A valve clip, tissue gripping device, or method of any of the clauses, comprising of a retrieval suture across the arms, for example as in FIG. 120F.

141. A valve clip, tissue gripping device, or method of any of the clauses, comprising of a retrieval/bailout shaft, for example, as in FIG. 104A.

142. A valve clip, tissue gripping device, or method of any of the clauses, wherein certain variations and modifications apparent to those skilled in the art, including embodiments or examples or clauses that may not provide all the features and benefits described herein; including obvious modifications and equivalents thereof; including embodiments comprising of various combinations or sub-combinations of the specific features and aspects of the embodiments examples claimed in the above clauses, wherein the steps of any methods need not be performed sequentially.

143. A valve clip, tissue gripping device, or method of any of the clauses, wherein certain variations and modifications apparent to those skilled in the art, including embodiments or examples or clauses or claims that may not provide all the features and benefits described herein or in any of the co-owned and referenced patent applications; including obvious modifications and equivalents thereof; including embodiments comprising of various combinations or sub-combinations of the specific features and aspects of the embodiments examples claimed in the above clauses or claimed in any of the co-owned and referenced patent applications, wherein the steps of any methods need not be performed sequentially.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 14 shows laser-cut flat pattern of an exemplary embodiment of an inner arm of a straight fixation device.

FIG. 15 shows relaxed 3D configuration of an exemplary embodiment of an inner arm of a straight fixation device.

FIG. 16 shows relaxed 3D configuration of an exemplary embodiment of an outer arm of a straight fixation device.

FIG. 17 shows laser-cut flat pattern of an exemplary embodiment of an outer arm of a straight fixation device.

FIGS. 18-20 show 3D views of an exemplary base bracket 5.

FIG. 35 shows the exemplary embodiment of the inverter with a stop feature to prevent overlapping of inverters during the loaded and/or deployed state.

FIG. 36 illustrates the exemplary embodiment of the straight fixation device with one outer arm lowered.

FIG. 37 illustrates the exemplary embodiment of the fixation device with both outer arms lowered.

FIG. 38 shows an alternative exemplary embodiments, schematics and/or configurations to lower and/or invert the inner arms.

FIG. 44 illustrates the schematic of the sutures 174, 175 looped around an exemplary release rod 160 utilizing key features of the release bar 72.

FIG. 45 shows a magnified view of FIG. 43, wherein the sutures are looped around the Release Rod 160.

FIG. 46 illustrates the schematic of the sutures after the release rod is partially retracted.

FIG. 47 shows a magnified view of FIG. 45, wherein some of the sutures are released from the release bar after the release rod is partially retracted.

FIG. 48 shows an exemplary embodiment of an inverter with a stop feature.

FIGS. 49-50 show various configurations of the embodiment of the inverter

FIG. 58 shows a photographic image of a straight prototype, wherein the fixation device (back view) is in a loaded configuration and covered with fabric.

FIG. 59 shows a side view photographic image of a straight prototype shown in FIG. 58.

FIG. 60 shows a front view photographic image of a straight prototype shown in FIG. 58.

FIG. 69A shows an embodiment of the fixation device formed using wire loops.

FIG. 69B show an exemplary configuration of nested wire loop assembly for inner or outer arms.

FIG. 70 shows a schematic of the fixation device shown in FIG. 68, loaded in a delivery device.

FIGS. 95-99 are photographic images of a preferred embodiment of an exemplary 12 Fr catheter-based delivery system used to deploy the fixation device within the heart.

DETAILED DESCRIPTION OF THE INVENTION

I. Cardiac Physiology

Figure 1:
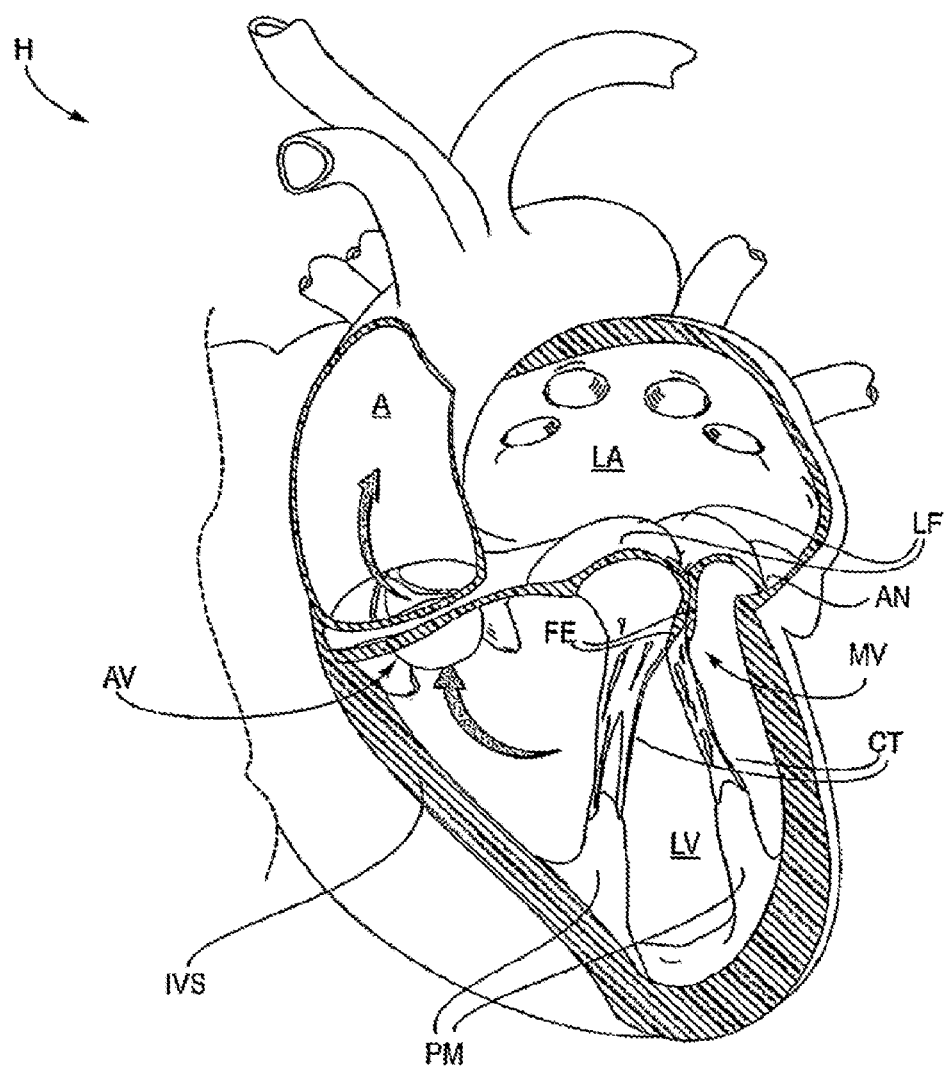
FIG. 1 illustrates the left ventricle and left atrium of the human heart during systole.

The left ventricle LV of a normal heart H in systole is illustrated in FIG. 1. The left ventricle LV is contracting and blood flows outwardly through the tricuspid (aortic) valve AV in the direction of the arrows. Backflow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
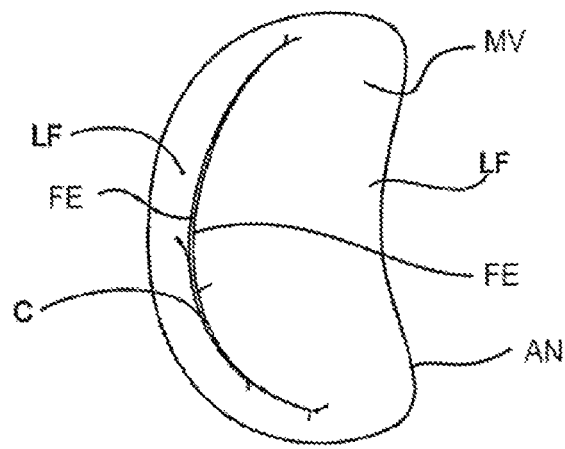
FIG. 2 illustrates the free edges of mitral valve leaflets in normal coaptation.
Figure 3:
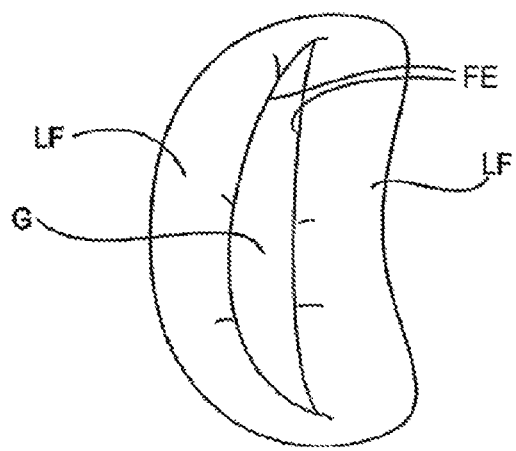
FIG. 3 illustrates the free edges of mitral valve leaflets in regurgitative coaptation.

A number of structural defects in the heart can cause mitral valve regurgitation. Regurgitation occurs when the valve leaflets do not close properly allowing leakage from the ventricle into the atrium. As shown in FIG. 2, the free edges of the anterior and posterior leaflets normally meet along a line of coaptation C. An example of a defect causing regurgitation is shown in FIG. 3. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview

The present invention provides methods and devices for grasping, approximating and fixating tissues such as valve leaflets to treat cardiac valve regurgitation, particularly mitral valve regurgitation. The present invention also provides features that allow repositioning and removal of the device if so desired, particularly in areas where removal may be hindered by anatomical features such as chordae CT. Such removal would allow the surgeon to re-approach the valve in a new manner if so desired.

Grasping will preferably be atraumatic providing a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

The devices and methods of the invention rely upon the use of an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve and tricuspid valve.

As explained in co-owned and reference application (PCT/US2017/042003), the fixation device is adaptable to both retrograde and antegrade configurations for deployment. The fixation device is attached to the Release bar, which is part of the distal delivery catheter as referenced in the previous PCT. In both methods, the placement and position of the device remains unchanged. This may allow the fixation device to be deployed using various entry points that best suit the user need. For illustration purposes, an antegrade approach will be primarily described going forward.

FIGS. 4-9 show images of a few exemplary combinations and configurations of the preferred implant device.

Figure 4:
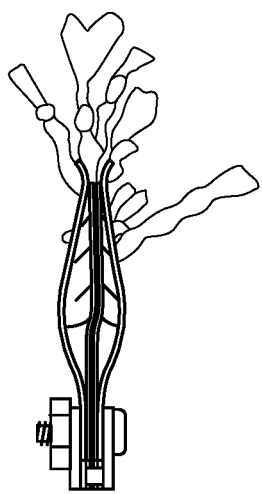
FIGS. 4-9 show photographic images of various exemplary combinations and configurations of some exemplary prototypes of this invention.
Figure 5:
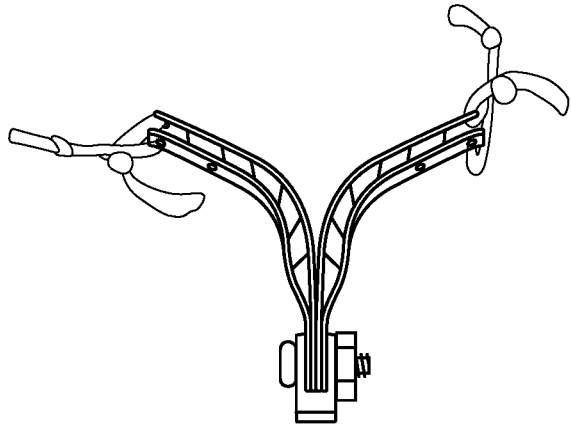

FIGS. 4 and 5 show images of the exemplary standard sizes of straight and curved configuration of the implant device.

Figure 6:
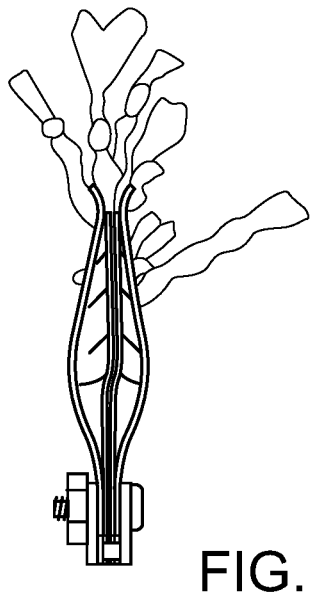
Figure 7:
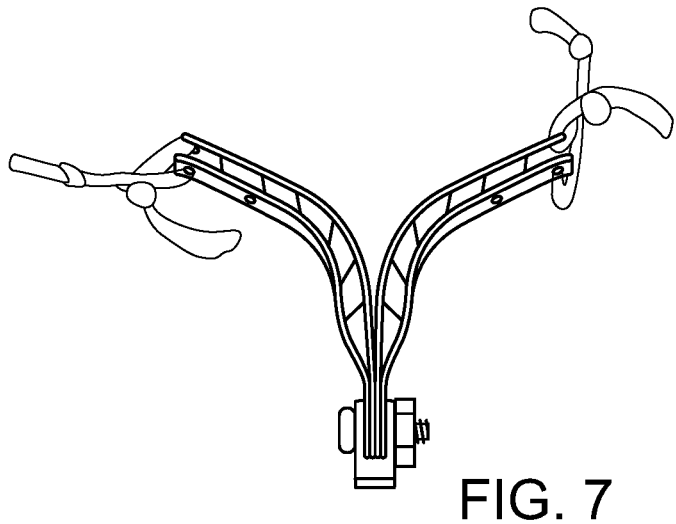

FIGS. 6 and 7 show images of the exemplary larger sizes of straight and curved configuration of the implant device.

Figure 8:
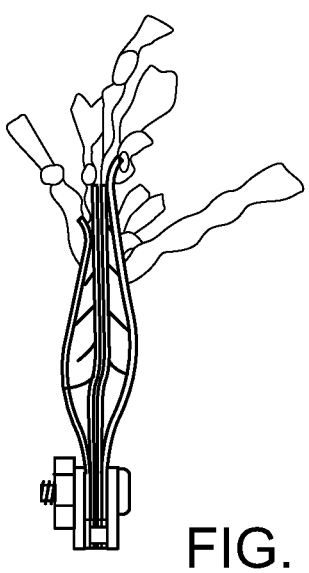
Figure 9:
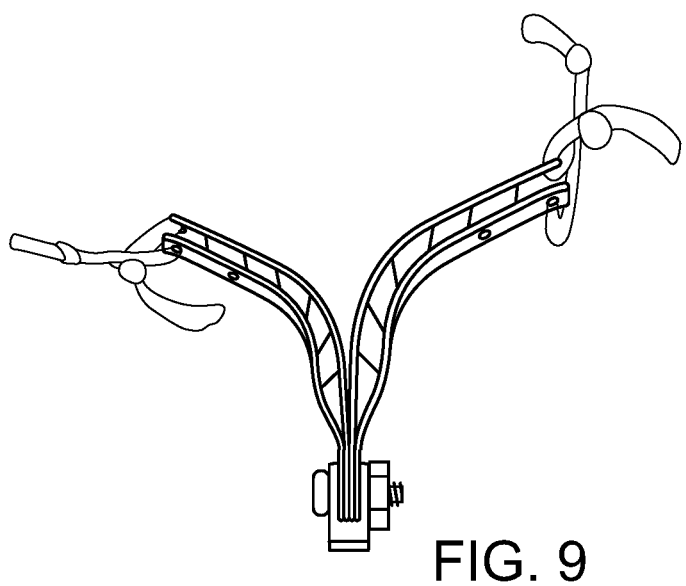

FIGS. 8 and 9 show images of the exemplary asymmetric configurations of straight and curved implant devices using standard and larger sizes.

Figure 10:
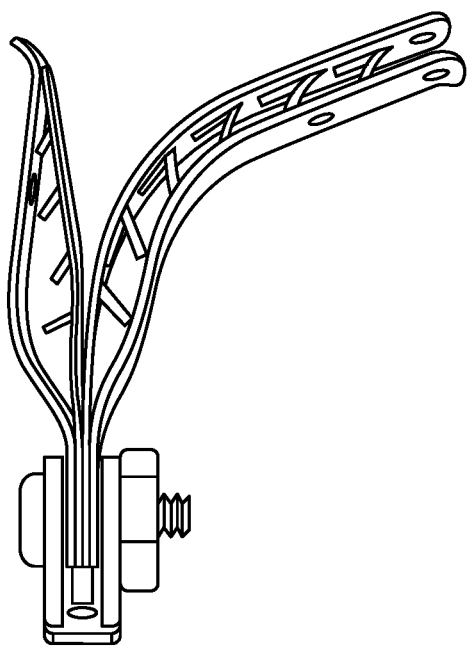
FIG. 10 shows a photographic image of an exemplary configuration of the prototype that is a combination of straight and curved devices.

FIG. 10 shows an image an exemplary configuration of device that is a combination of straight and curved device. Note, each arm can also be of different thickness, width, length and profile to configure/vary the grasp or coaptation length, grasp force, anulus cinching force.

Figure 11:
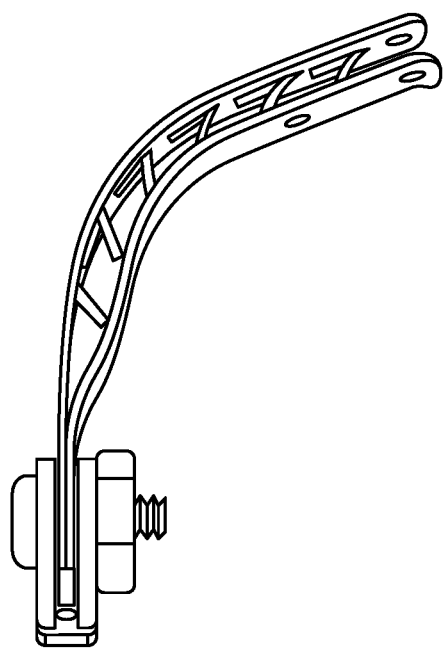
FIG. 11 shows a photographic image of an exemplary configuration of a curved prototype with only one side.

FIG. 11 shows an image of an exemplary configuration of a curved device with only one side. This allows for a configuration optimized for single leaflet grasping. This concept may be used for other competition devices too. For example, an exemplary embodiment of this invention can be seen in FIG. 12, wherein the Arms of the MitraClip® is cut and removed from one side, while keeping all other aspects of the design intact.

In one preferred method, two such single leaflet devices (FIGS. 10-12) may be deployed on the same leaflet at different sites or on different leaflets and configured to be pulled together and constrained in place. This can be done by techniques and designs common to those skilled in the art. For example, the devices can be configured with attached sutures or tethers with or without keyed or mating features. Once each of these devices have been deployed on the leaflets, the sutures or tethers may then be used pull the two devices together. Once sufficiently approximated to eliminate or reduce regurgitation (as determined via ultrasound or fluoroscopic imaging feedback), the sutures may be secured/fixed/crimped together, and excess strands cut and removed. Thus, constraining the devices in a configuration that prevents regurgitation. Alternatively, the action of pulling the two devices together can be used to mechanically lock them in place.

Figure 13:
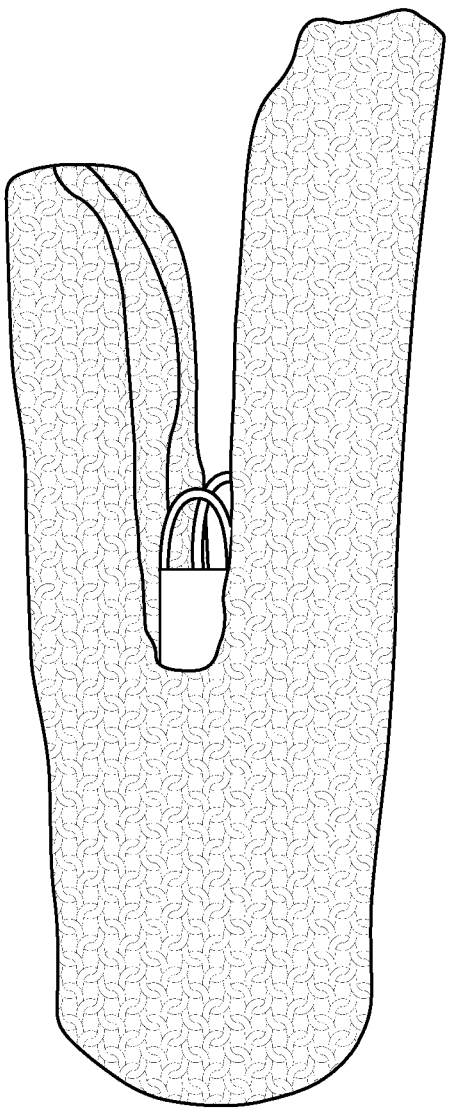

FIG. 13 shows an image of the MitraClip® device with asymmetric arm lengths, similar to the exemplary device shown in FIG. 8.

FIG. 14 shows flat-pattern of a preferred exemplary embodiment of an inner arm 12 of the straight fixation device. The inner arm consists of atraumatic dual-barb or v-shaped protrusions 18 that allow the inner arm 12 to grip the LF of the MV. Features 24-25 allow the passage of sutures and/or attachment of suture loops to manipulate the inner arms. Features 20-21 couple base bracket 5 to the inner arms. Openings 26 allow the polyester fabric to adhere to one another and prevent movement of the polyester fabric during advancement and/or retraction of the fixation device through the catheter system.

FIG. 15 shows an 3D view of the exemplary embodiment of an inner arm 14 of the fixation device shown in FIG. 14.

FIG. 16 shows 3D view of an exemplary embodiment of an outer arm 15 of the straight fixation device.

FIG. 17 shows flat-pattern of the outer arm 13 shown in FIG. 16. Features 32 and 34 couple base bracket 5 to the outer arms. Features 37-40 allow the passage of sutures and/or attachment of suture loops to manipulate outer arms 13. Opening 37 allows the polyester fabric to adhere to one another and prevents movement of the polyester fabric during advancement and/or retraction of the fixation device through the catheter system.

FIG. 18 shows a component 50 of the base bracket 5. It consists of hinge joint 56 and threaded openings 60 and 62 to allow for miniature screws to fasten arms between the components 50 and 52.

FIG. 19 shows right component 52 of the base bracket 5. It consists of openings 61 and 63, which allow for miniature screws to fasten arms between the components 50 and 52.

FIG. 20 shows an alternative view of the base bracket 5 depicting the hinge joint 56. Opening 65 allows passage of Release Rod 160 for detachable attachment of the base bracket 5 to the Release bar 70, 72.

Figure 21:
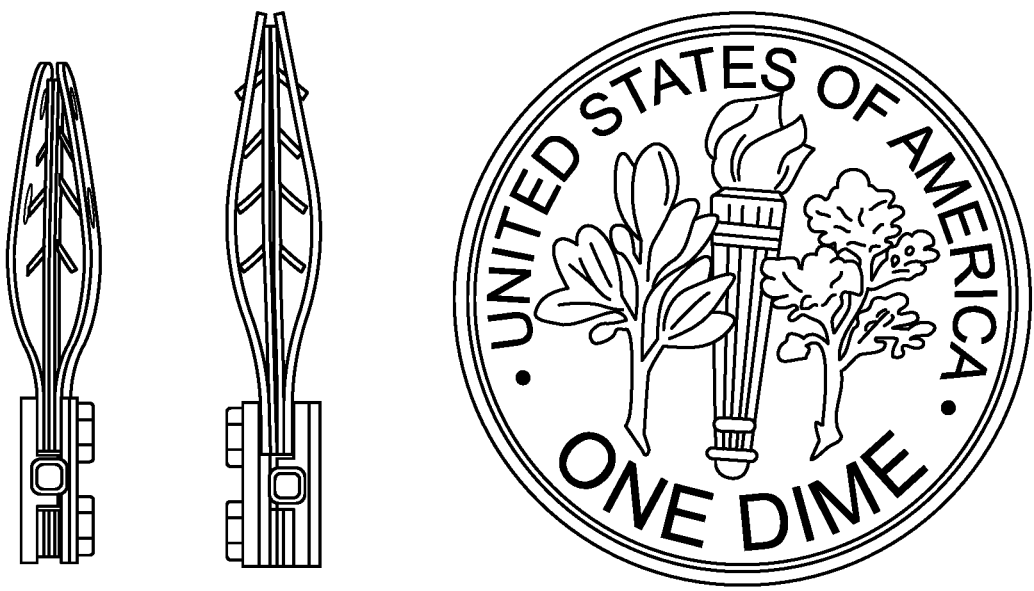
FIG. 21 shows photographic images of two different exemplary sizes of the straight prototype (front view) next to a dime as scale.

FIG. 21 shows the image of the front view of a short and long straight design prototypes next to a dime for a side-by-side comparison of its dimensions.

Figure 22:
FIG. 22 shows a photographic image of a straight prototype (side view) next to a dime as scale.

FIG. 22 shows the image of the side view of the long straight design prototype next to a dime as scale.

Figure 23:
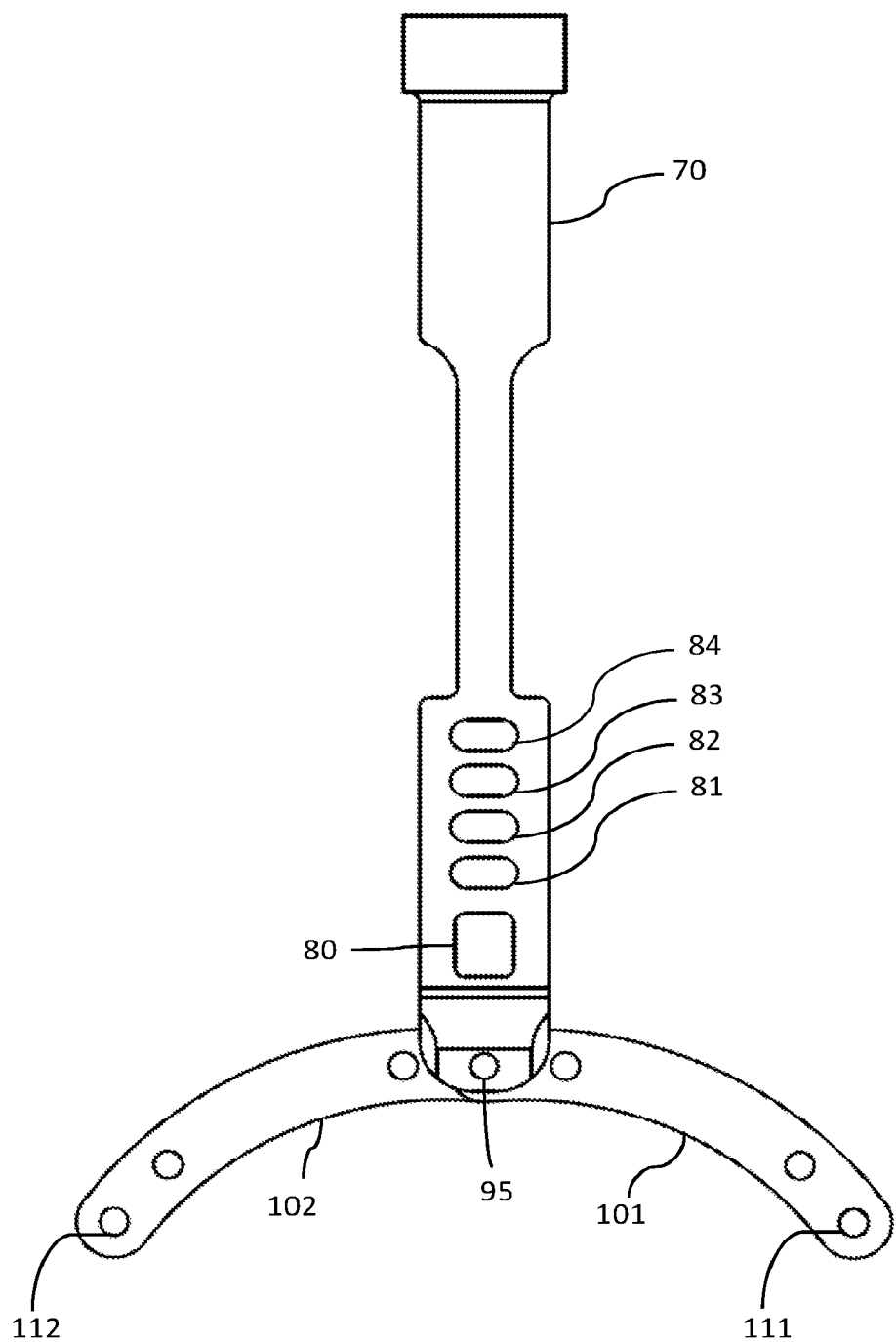
FIG. 23 shows an exemplary embodiment of a release bar 70 with invertors 102, 101.

FIG. 23 shows and alternate exemplary embodiment of Release bar 70, wherein, a) instead of single attachment feature 80, now there are multiple such features 81-84 and b) instead of posts (see FIG. 13G-2, PCT/US2017/042003), Inverters 101, 102 are being used. These inverters provide increased lever arm to flex the outer arms, as compared to the posts.

The Inverters 101, 102 are hinged at 95 and hence, can swivel to allow easy passage through the catheter and provide a combination of configurations that may be used to manipulate the arms (for example, outer arms 13, 15, 195, 197).

The Inverters 101, 102 maybe a simple single component or can be of complex shape with multiple sub-components. Further, they can be a hinged, flexible, rigid and may be joined together immovably or movably. They can be arranged in any configuration to allow for optimal manipulation of the Arms. Furthermore, their surface may be suitably configured to improve functionality and/or to reduce friction.

Figure 24:
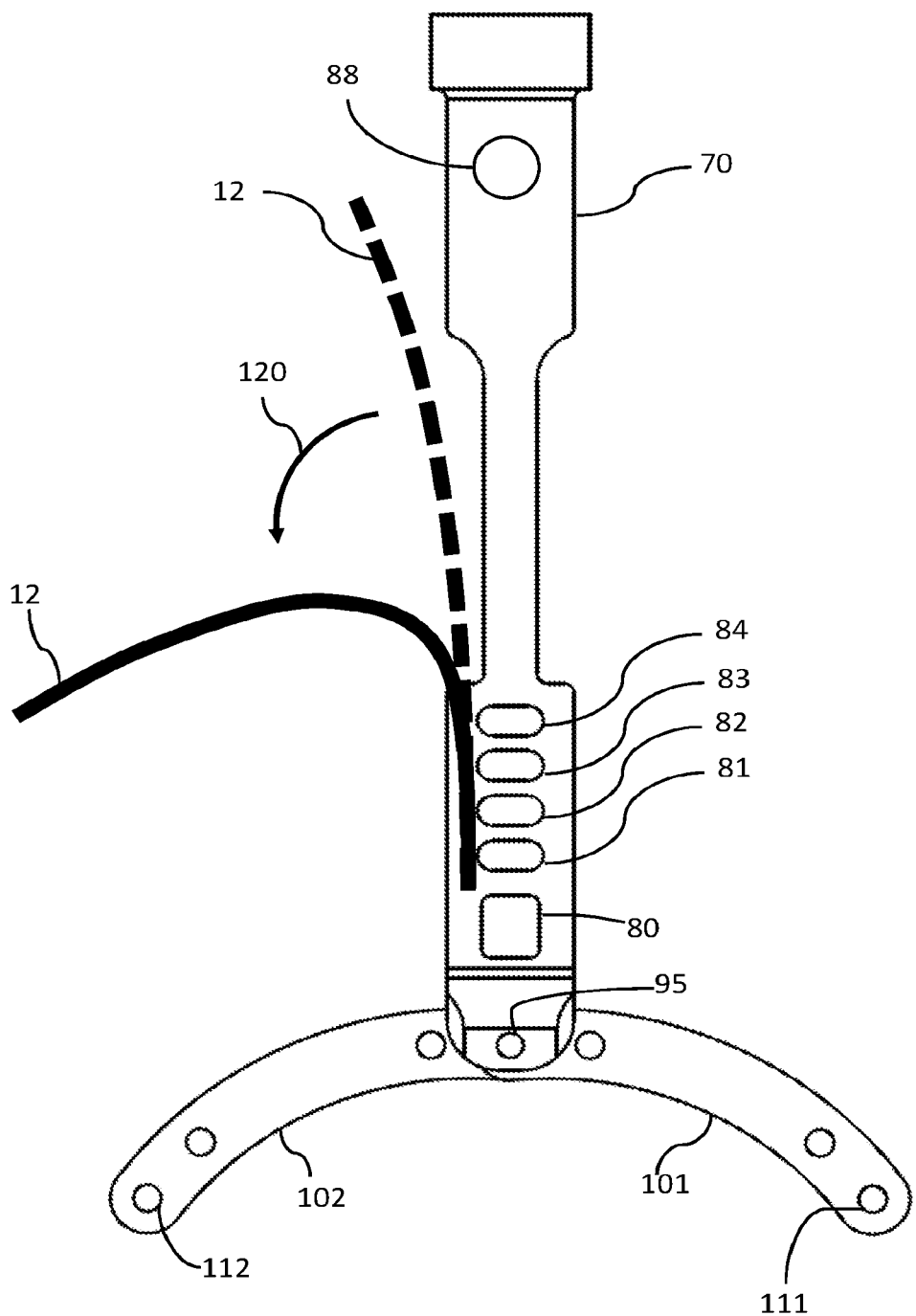
FIGS. 24-29 show a schematic representation of the inner arm of the fixation device with various exemplary suture attachment and actuation configurations, including deployable inverter arms in accordance with the principles of the present invention.

FIG. 24 shows an exemplary schematic wherein the inner arm 12 elastically lowers upon removal of biasing forces (as shown by arrow direction 120 and indicated by initial dotted-line position to final solid-line position).

Figure 25:
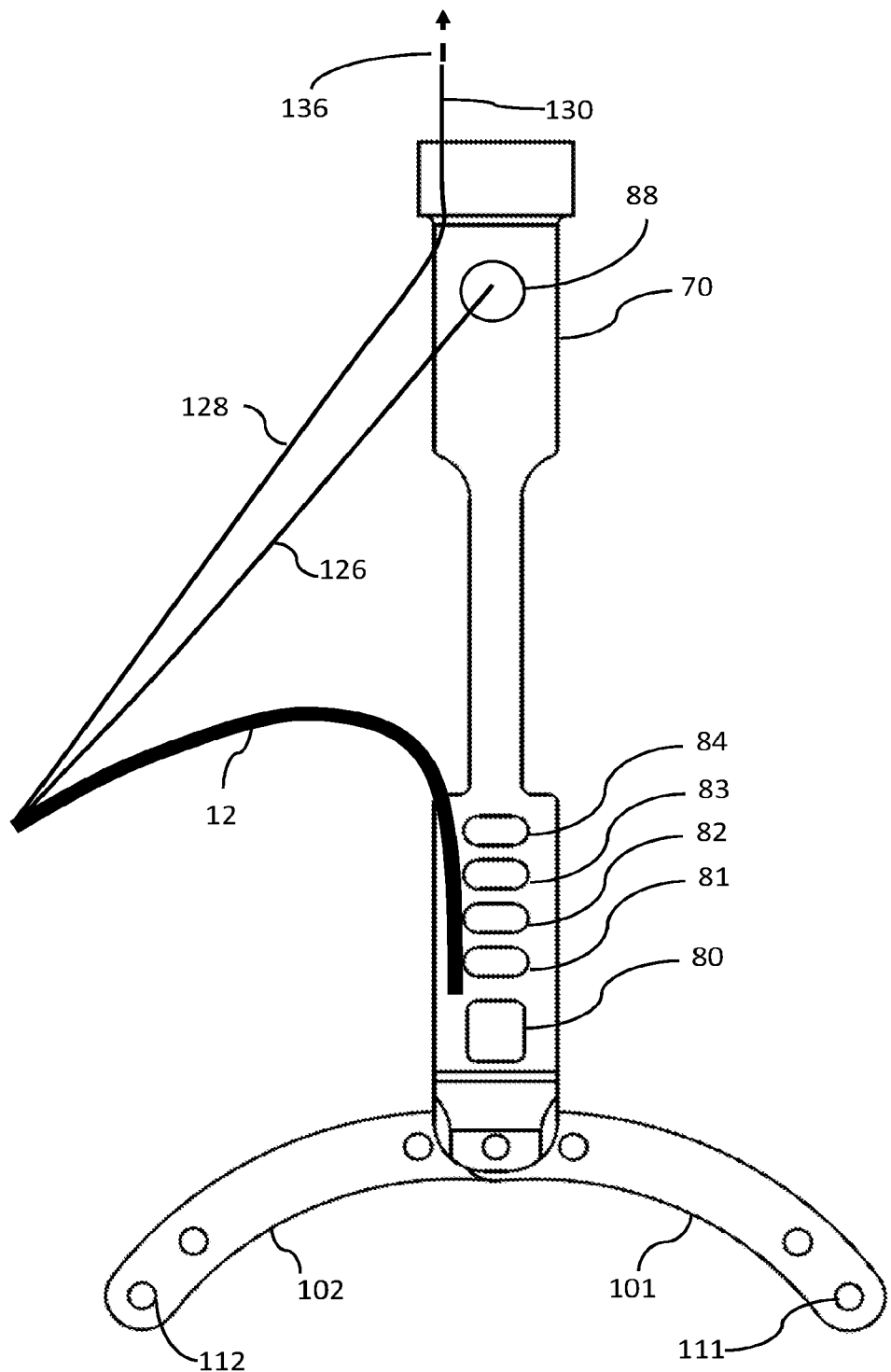

FIG. 25 shows the relatively equal increase in lengths of suture segments 126 and 128, as well as their angles. This configuration may cause a) increased frictional resistance hindering the elastic recoil of the arms, and b) decreased force needed to raise (straighten or bias) the inner arms.

Figure 26:
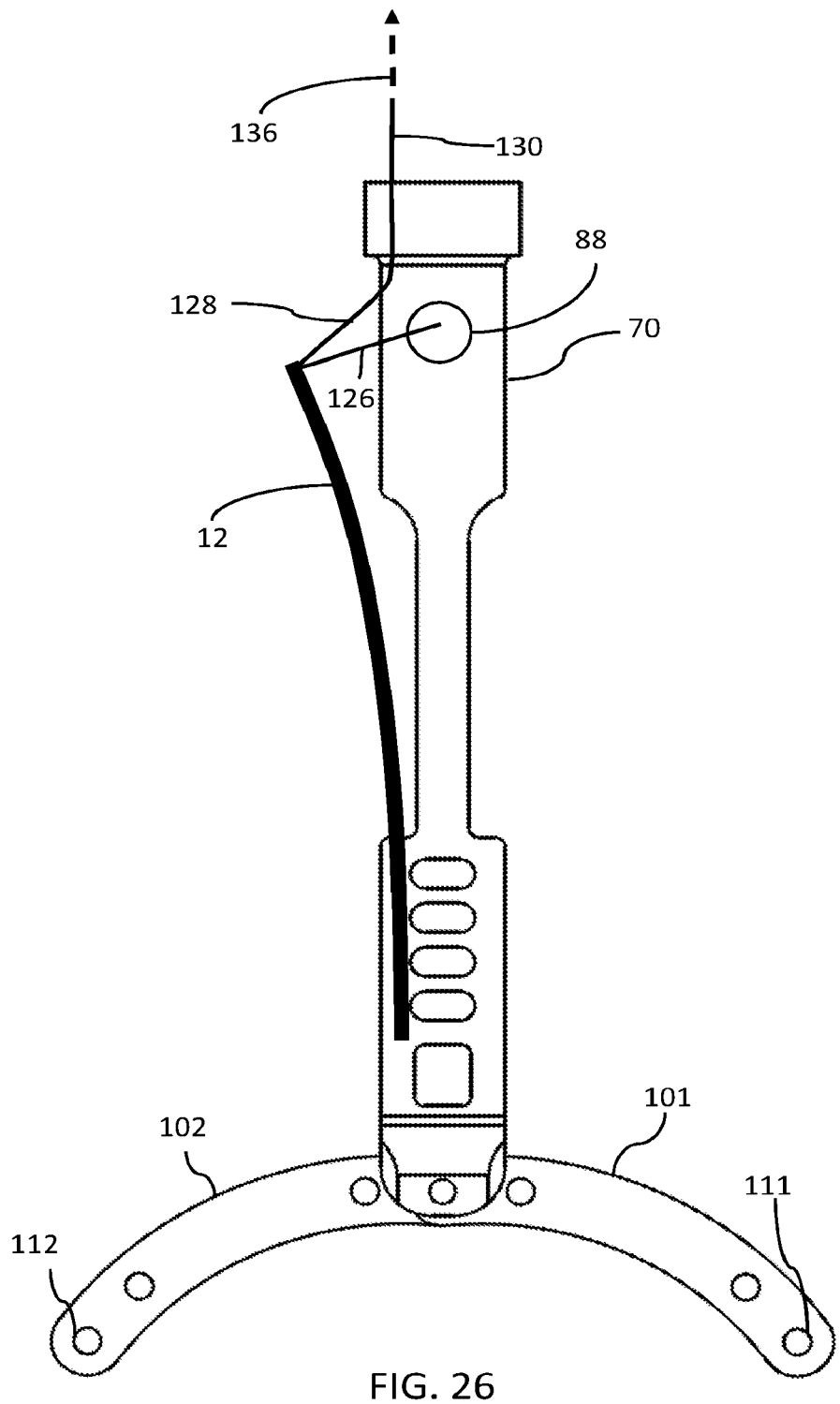

FIG. 26 shows schematic of inner arm 12 in raised position. This, as previously described in the PCT, is achieved by pulling 136 on the suture 130. That is, pulling 136 of the suture segment 130 causes progressive shortening of suture segments 128 and 126 leading to raising of the inner arm 12.

Similarly, releasing (or pushing) the suture allows for the inner arm to elastically recoil and return to its relaxed shape-set configuration. However, to those skilled in art can appreciate that this elastic recoil force is relatively low. Thus, lowering friction within the suture segments is paramount. Some of the characteristics that affect friction are a) coefficient of friction, b) angle between the segments 126 and 128, c) incremental length of the suture travel, d) number of bends and curves the suture is exposed to, e) flexibility of the suture, f) pushability of the suture within the catheter lumen and so on.

Figure 27:
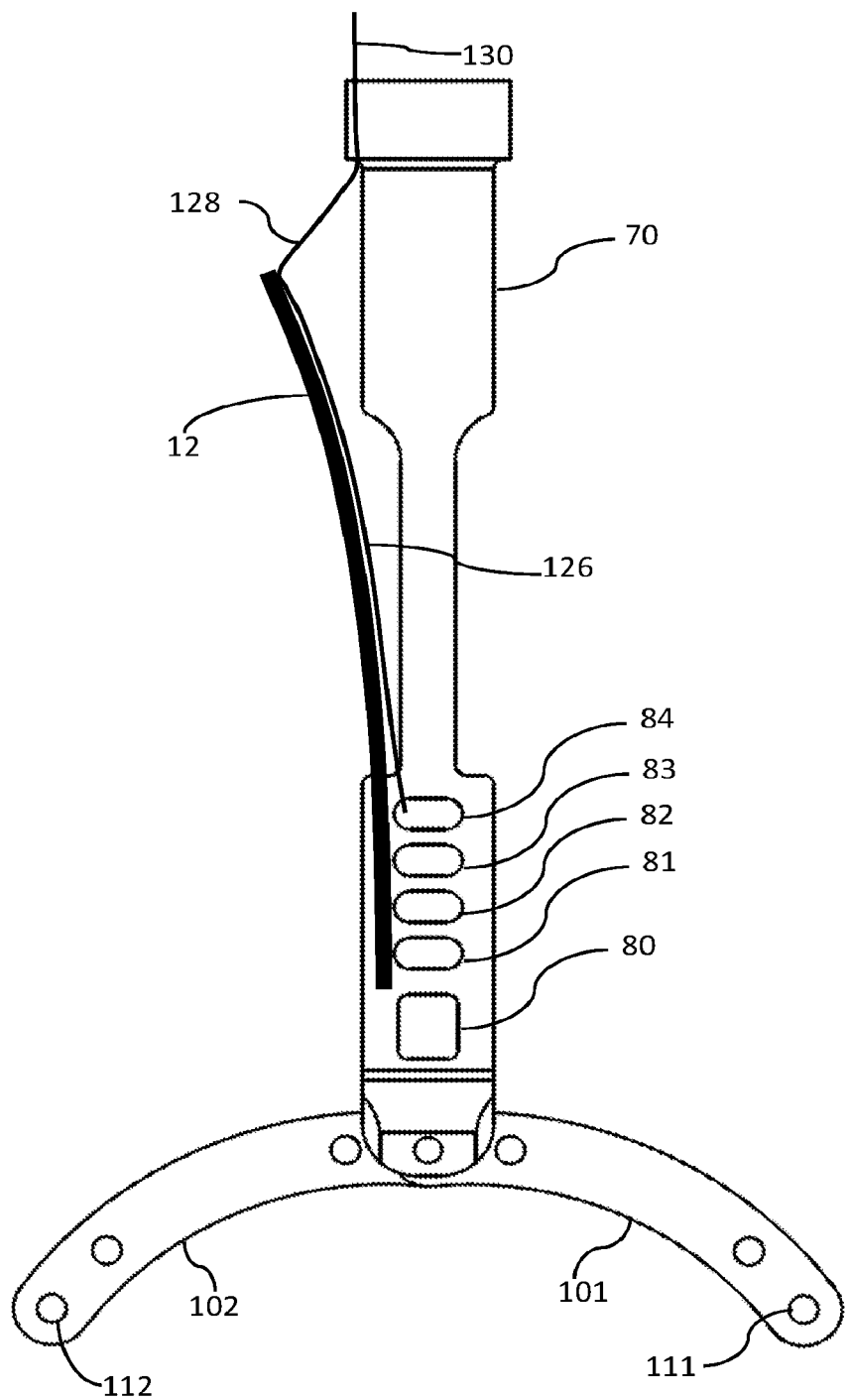
Figure 28:
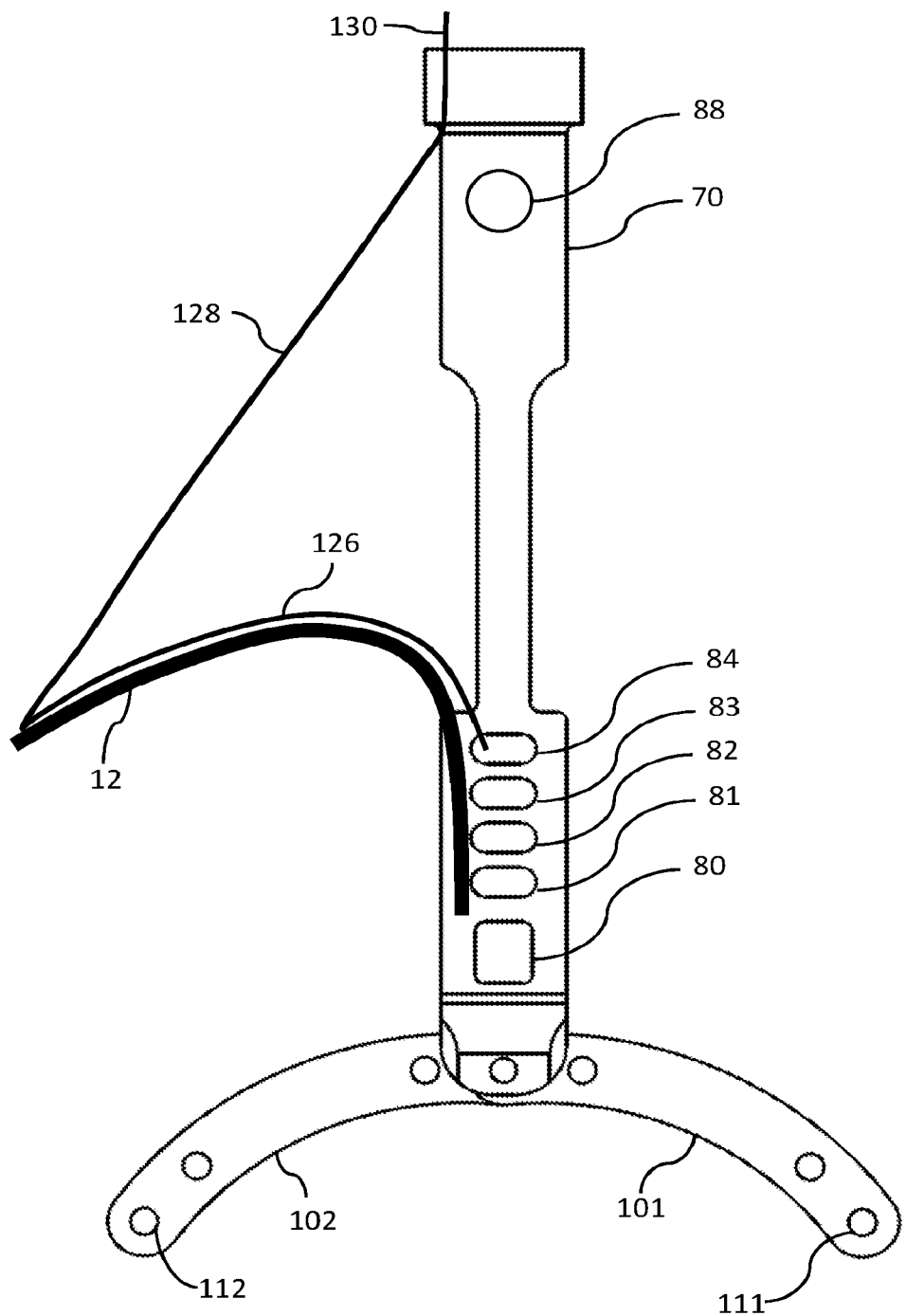
Figure 29:
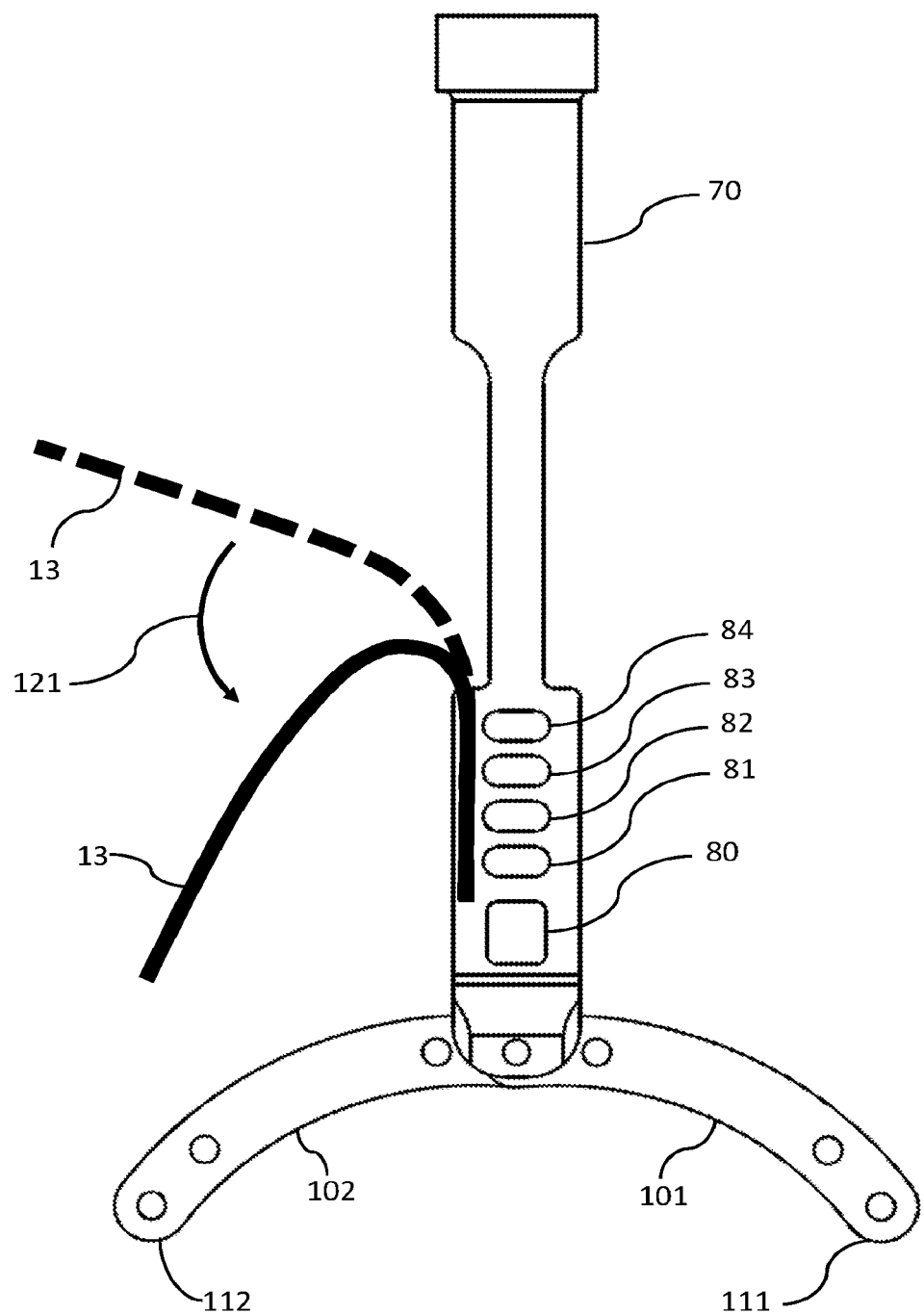
Figure 30:
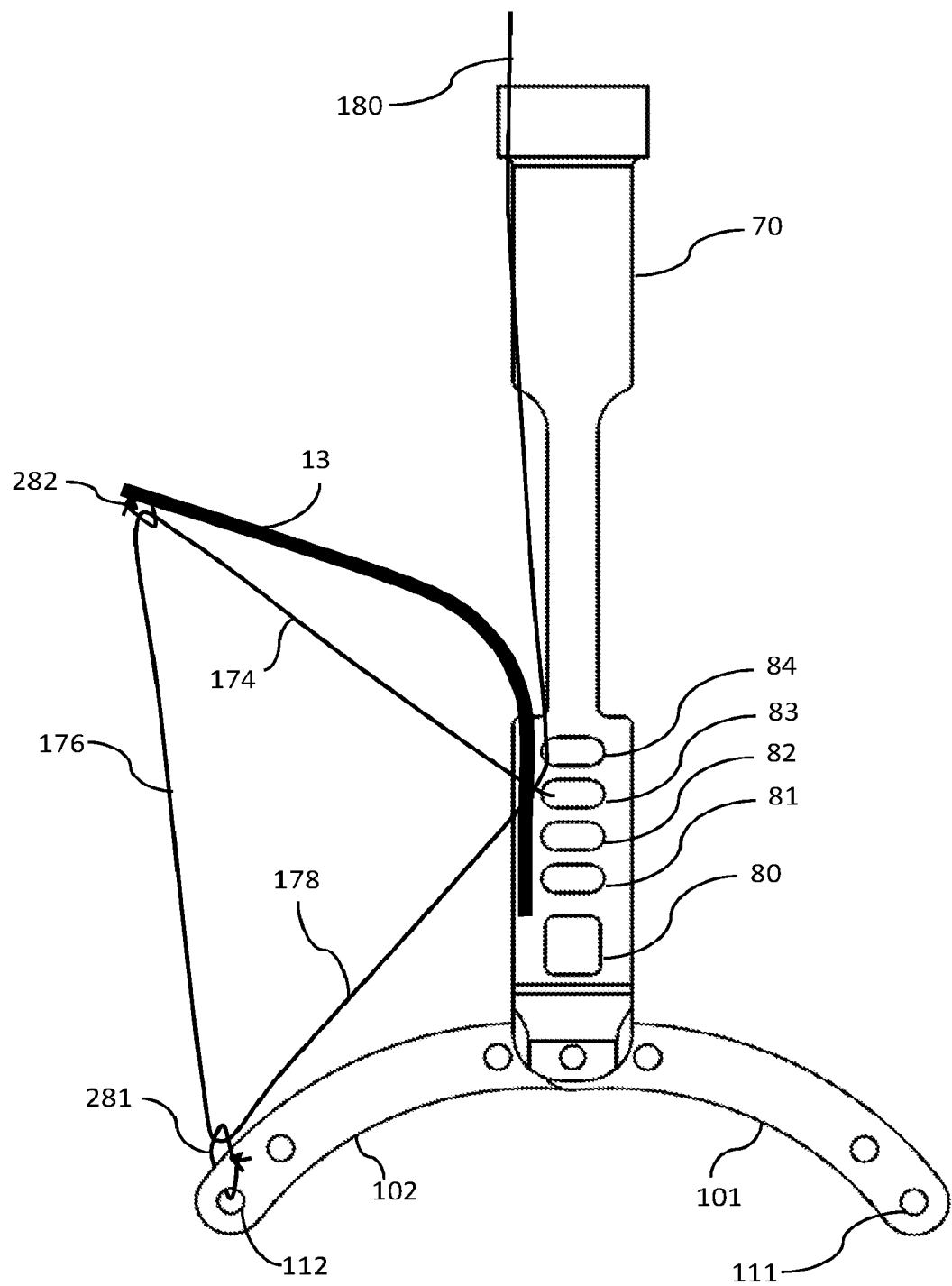
FIGS. 30-33 show alternative exemplary embodiments and/or configurations to lower and/or invert the laterally extending inverter arms.
Figure 31:
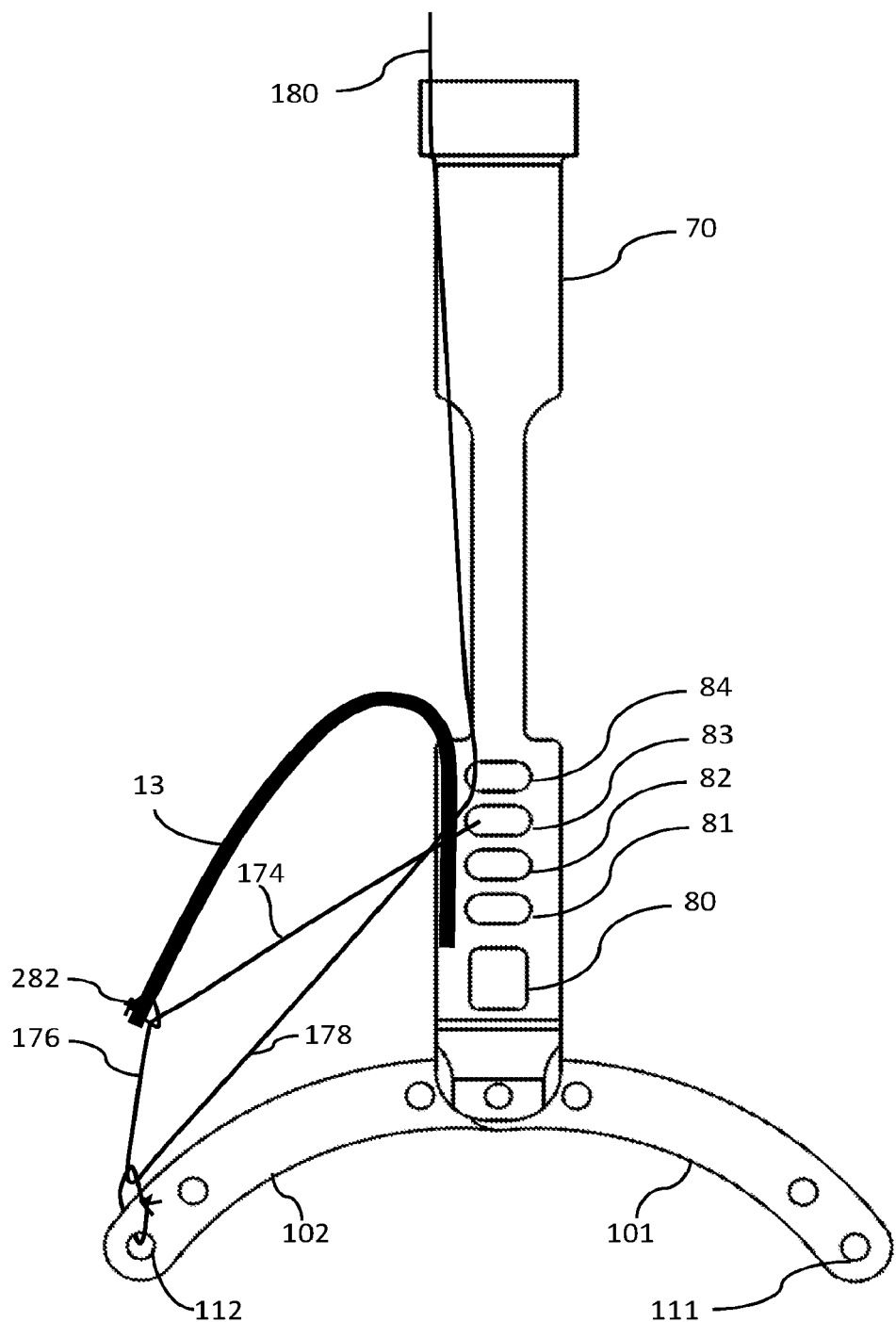
Figure 32:
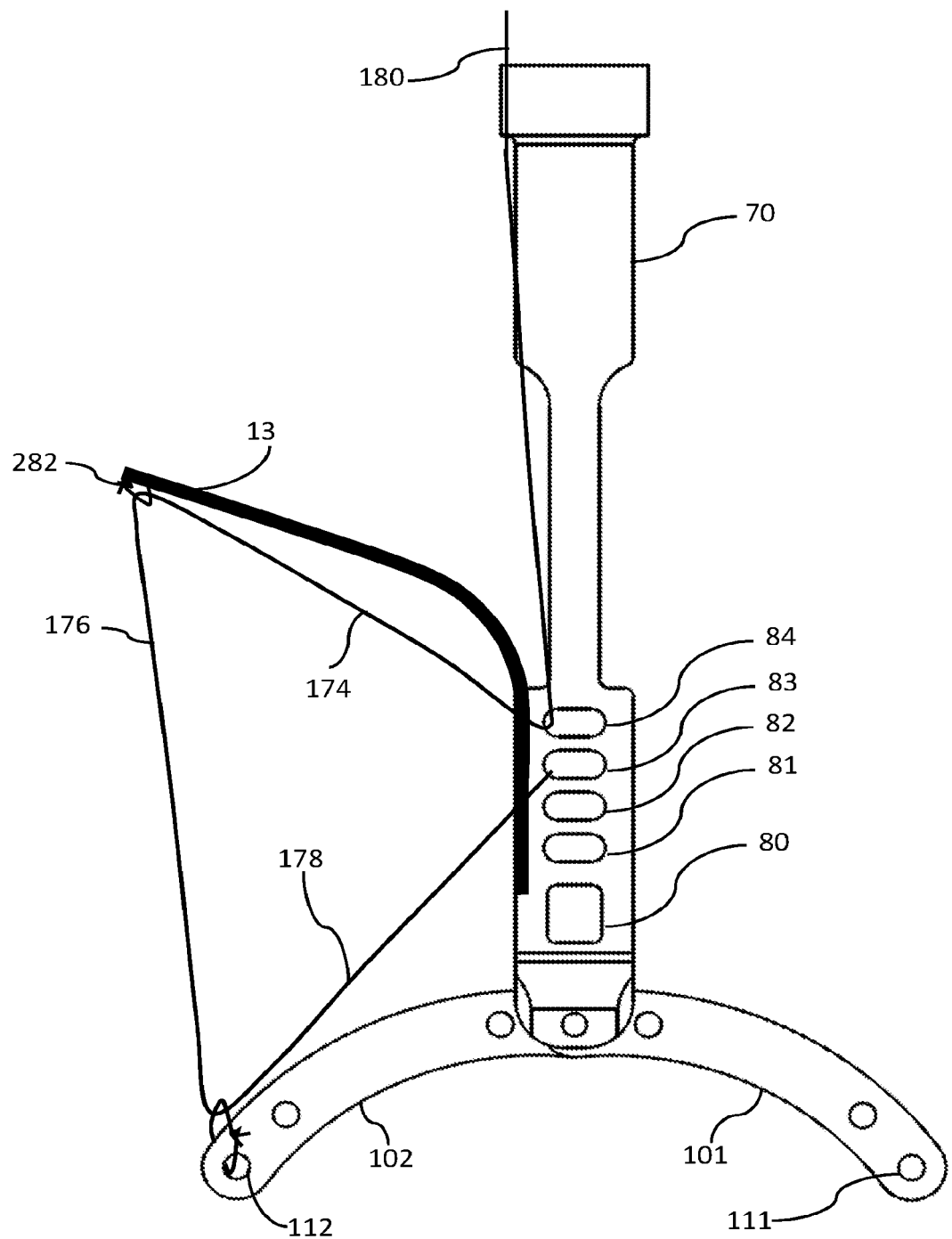
Figure 33:
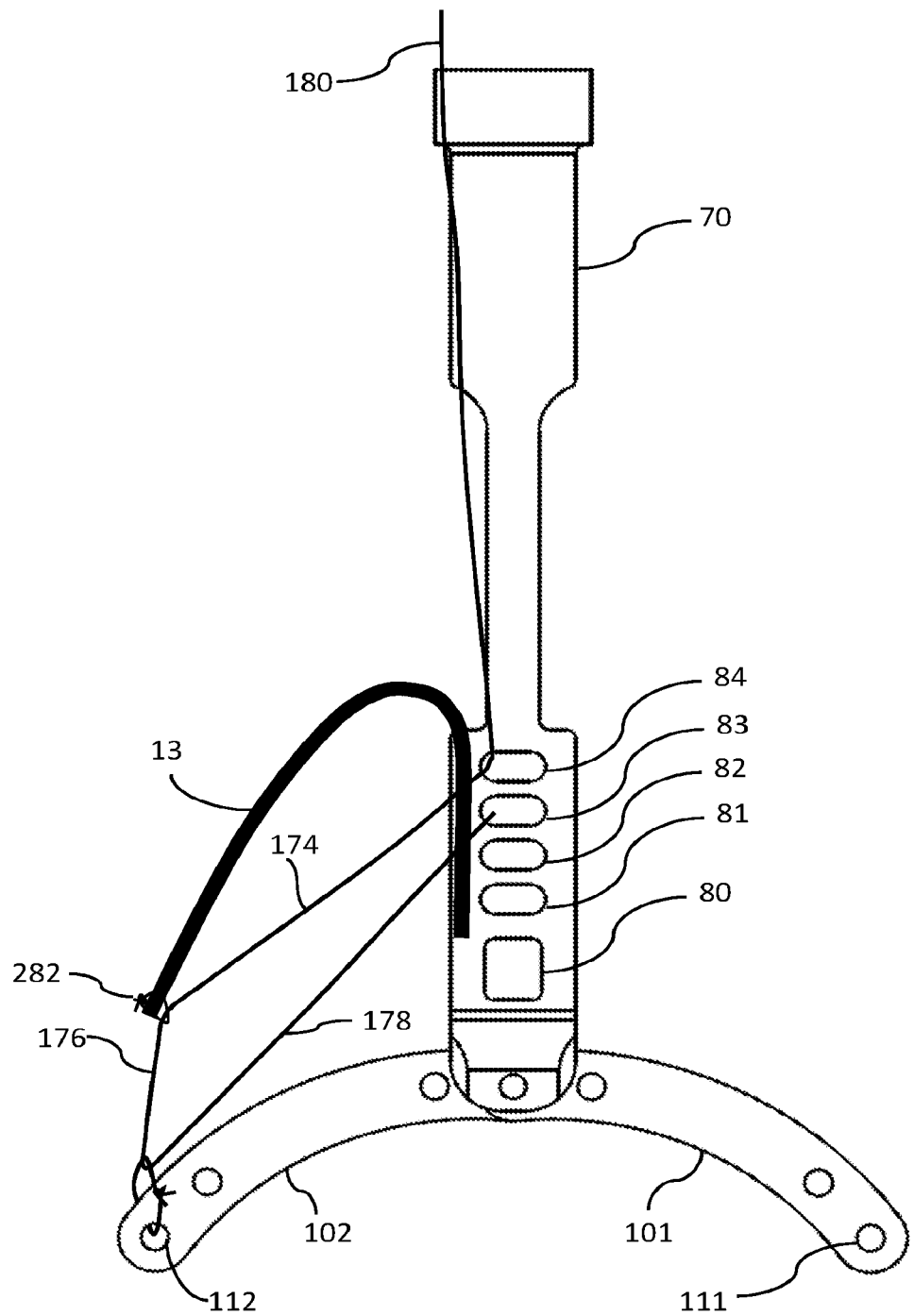

FIGS. 27-28 show an exemplary alternate embodiment as shown in FIG. 25, wherein the suture segment 126 is along the length of the inner arm 12 and terminates around release bar 76 at features 84 (instead of 88). Note the increase in angle between suture segments 126 and 128.

As can be inferred from FIGS. 27-28, the length of the segment 126 essentially remains the same over the movement of the inner arm, therefore, there is minimal travel of the suture at the tip of the inner arm 12. Further, the Inner arm needs to overcome and pull only segment 128. Hence, in a given condition with all other variable characteristics being same, the alternate configuration of terminating the suture loop at feature 84 (when compared to feature 88) provides lower resistance to the elastic lowering of Inner arm 12.

Similarly, FIGS. 29-33 show alternative exemplary embodiments and/or configurations to lower (and or invert) outer arms. In this configuration, manipulation of outer arms 13, 15, 195, 197 is accomplished by threading suture 180 through feature 84, suture segment 178 through suture loop 281, suture segment 176 through suture loop 282, and coupling suture segment 174 to feature 83 of release bar 70. Inversion of outer arms 13, 15, 195, 197 can further aid during bailout.

Figure 34:
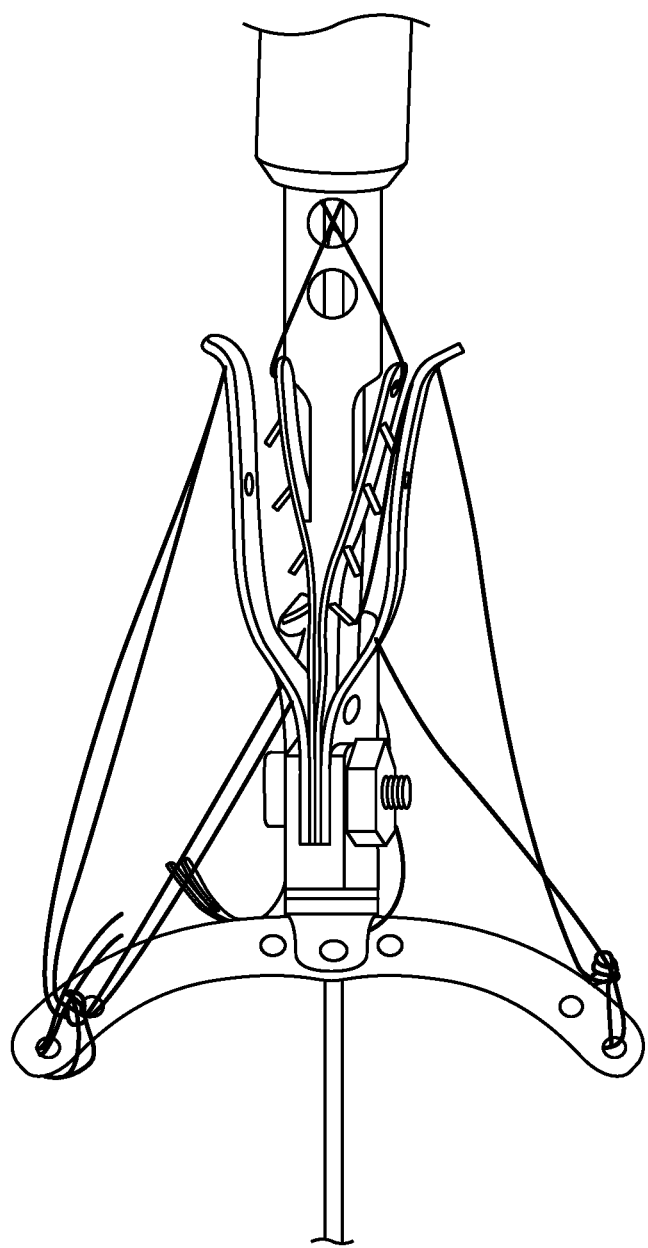
FIGS. 34-38 show photographic images of an exemplary embodiment with various arm manipulations and configurations.

FIG. 34 shows an image of an exemplary embodiment of release bar 76 with inverters 101, 102 and an exemplary implant device embodiment like the one depicted in FIG. 13D of the referenced PCT application.

Figure 35:
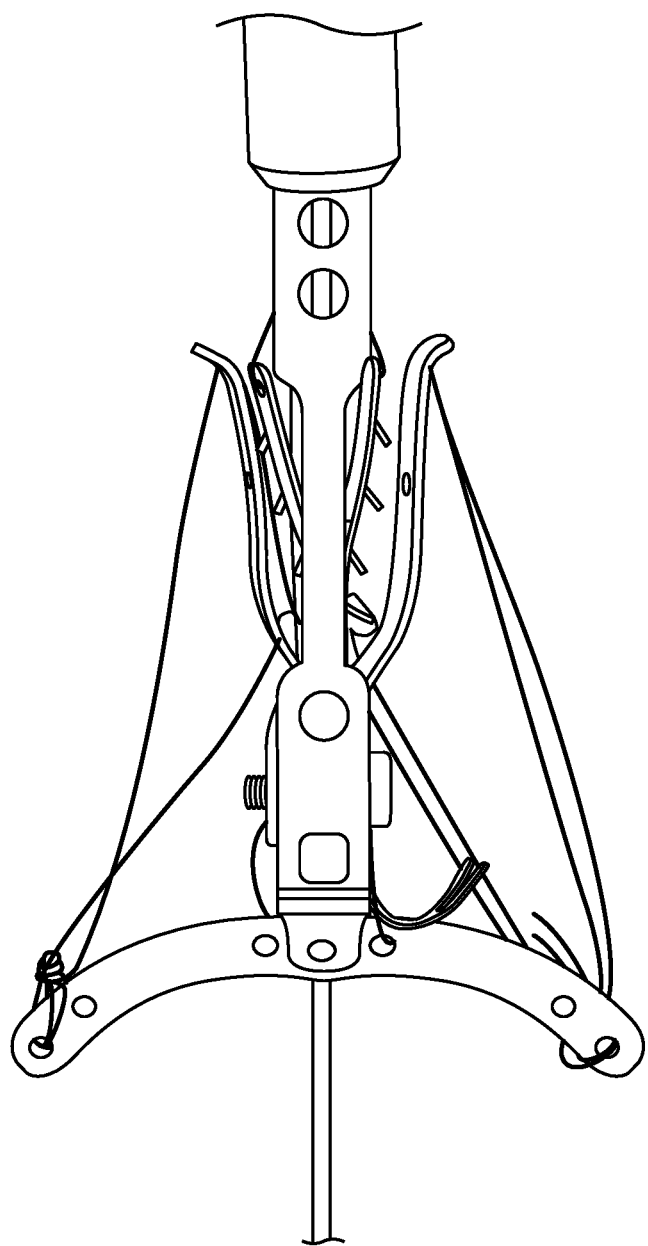

FIG. 35 shows a back-view image of the prototype in FIG. 34, wherein all arms are in raised configuration.

Figure 36:
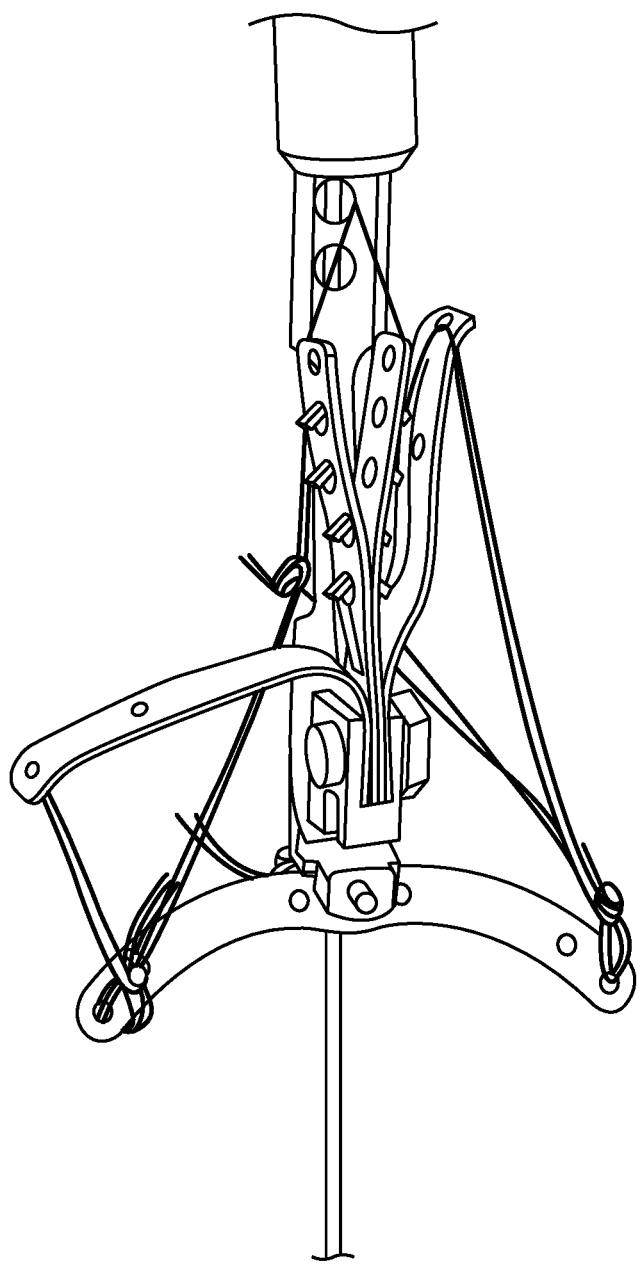

FIG. 36 shows an image of the exemplary ability to manipulate each arm independently—for example, only the Outer arm 13 is lowered.

Figure 37:
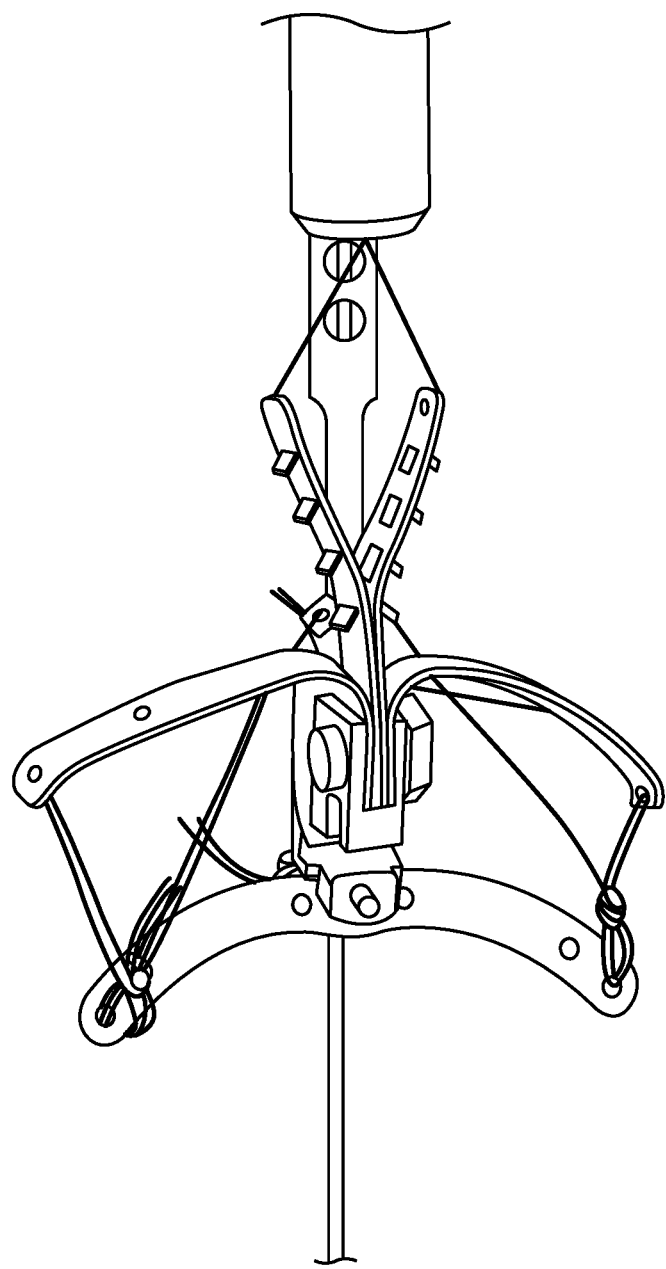

FIG. 37 shows an image of both Outer arms 13, 15 lowered/inverted.

Figure 38:
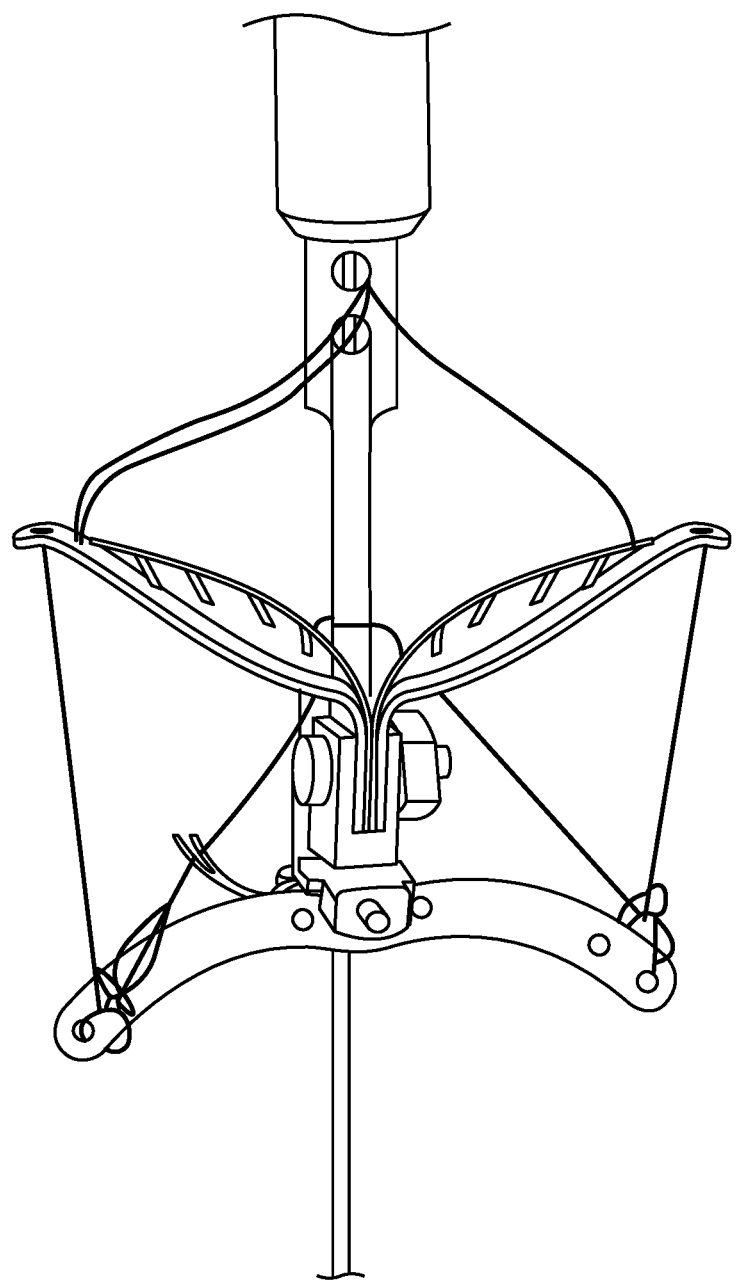

FIG. 38 shows an image of both Outer arms 13, 15 lowered to grasping angle and both Inner arms 12, 14 lowered over the Outer arms.

This invention, as previously described in the PCT provides the means and method of independent arm manipulations. This improves ease of use in the procedure and adopt according to the disease and anatomical conditions. Additionally, it allows the user to correct the grasp alignment if needed. For example, if on grasping the user determines that one side of the grasp is suboptimal, he can release just that side and grasp it again. Thus, saving significant amount of time when compared to redoing the entire grasping procedure again by releasing both leaflets.

Figure 39:
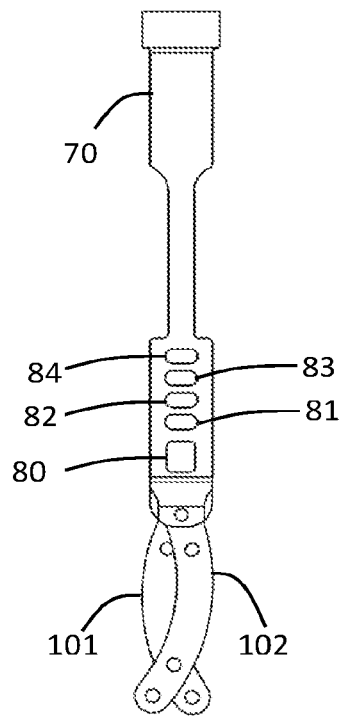
FIGS. 39-41 illustrate an exemplary embodiment of a release bar 70 with inverters 101, 102 in various views and collapsed configurations (FIGS. 39 and 40) and deployed a configuration (FIG. 41).
Figure 40:
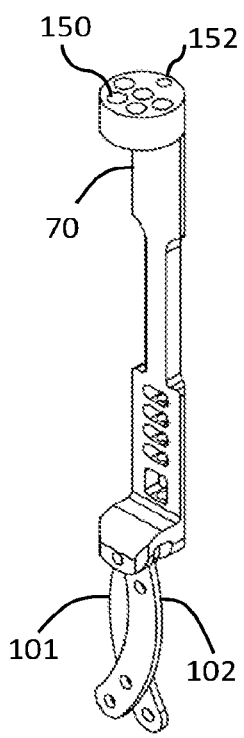
Figure 41:
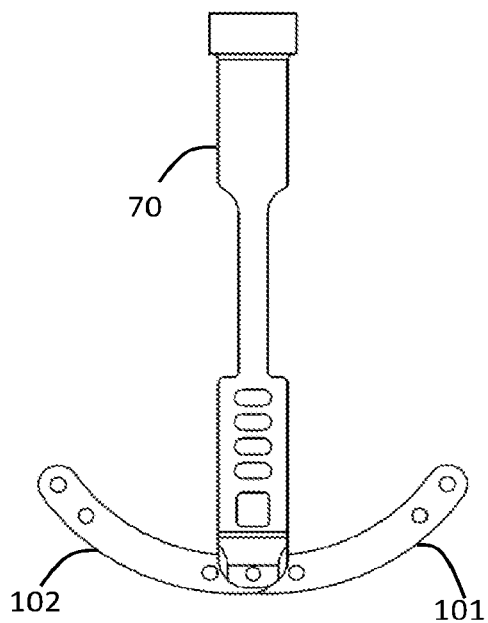

FIGS. 39-41 show a few possible configuration combinations of inverters 101, 102. The Inverters 101, 102 maybe a simple single component or can be of complex shape with multiple sub-components. Further, they can be a hinged, flexible, rigid and may be joined together immovably or movably. They can be arranged in any configuration to allow for optimal manipulation of the Arms. Furthermore, their surface may be suitably configured to improve functionality and or reduce friction.

Figures 42, 43:
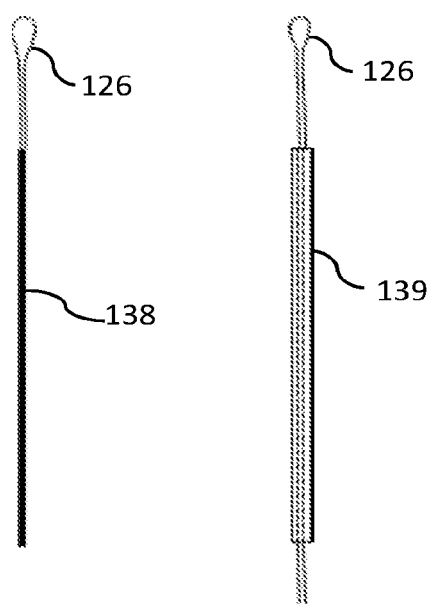
FIG. 42 shows and exemplary actuation pull-wire comprising of a distal suture loop segment crimped/coupled to a metal rod/wire/mandrel.
FIG. 43 shows and exemplary actuation pull-wire comprising of a distal suture loop segment paired with a tubing.

FIG. 42 shows suture 126 coupled or crimped to a metal wire 138, mitigating friction inside the catheter lumen as it is pulled or pushed. While pulling is not an issue with any suture or rope (high tensile strength, low column/compressive strength), having a metal wire or rod (with sufficient column/compressive strength when inside a catheter lumen) over most of the proximal length of the catheter provides, provides the required push force to overcome and frictional resistance hindering elastic recoil of the arms. In come embodiments, the pushability may be used to augment the recoil of the arms.

Further, FIG. 43 illustrates exemplary embodiment of a suture 126 coupled to rigid tube 139, which can be stainless steel wire, plastic tube and/or metal tube. Rigid tube 139 can be pulled or pushed, thereby reducing the internal friction of the catheter and/or augment strain recovery of the arms.

FIG. 44 illustrates the schematic of sutures looped around release rod 160 utilizing key features of exemplary release bar 72. As can be seen, release rod 160 is completely inserted through release bar 72, anchoring sutures 125 to feature 84 and sutures 174 and 175 to feature 82. Further, the sutures are inserted through features 82 and 84 from the front of release bar 72; however, due to the versatility of release bar 72, the sutures can be inserted from the back or any combinations of front and/or back insertion.

FIG. 45 shows a magnified view of sutures 125, 174 and 175 around release rod 160 of FIG. 43. As can be seen, features 82 and 84 have sufficient room for sutures 125, 174 and 175 to freely move without additional tension to the sutures.

FIG. 46 illustrates the schematic of sutures 125, 174 and 175 after release rod 160 has been partially retracted past feature 82, thus decoupling sutures 174 and 175 from release bar 72.

FIG. 47 shows a magnified view of FIG. 45, wherein sutures 174 and 175 are decoupled from release bar 72 after the release rod 160 has been partially retracted. As can be seen, sutures 174 and 175 are decoupled without tangling. This is the case regardless of the point of entry of the suture (i.e. from behind and/or in front of release bar 72).

FIG. 48 shows an exemplary embodiment of inverters 116 and 117 comprised of stop feature 142 utilized to prevent the inverters from overlapping or moving in the opposite direction when loading the fixation device into a catheter and/or during deployment of the fixation device.

FIG. 49 shows an exemplary embodiment of release bar 72 with inverter 117 in a deployed state. Release bar 72 is shown with a plurality of features 80-88 to allow passages of sutures to loop through and manipulate the arms of the fixation device. In addition, any of these features maybe used to couple the device, with the base towards the distal end (towards 80) or proximal end (towards 88) of the release bar. Thus, allowing device configuration flexibility, for example, allowing antegrade or retrograde approach to the mitral valve.

FIG. 50 shows an exemplary embodiment of release bar 72 with inverter 117 in a catheter loaded configuration. Stop feature 142 of inverter 117 is shown to limit rotation of inverter 117, for example, limit past 10 or 20 or 120 degrees beyond the center axis of release bar 72 in a catheter loaded configuration.

Figures 51, 52:
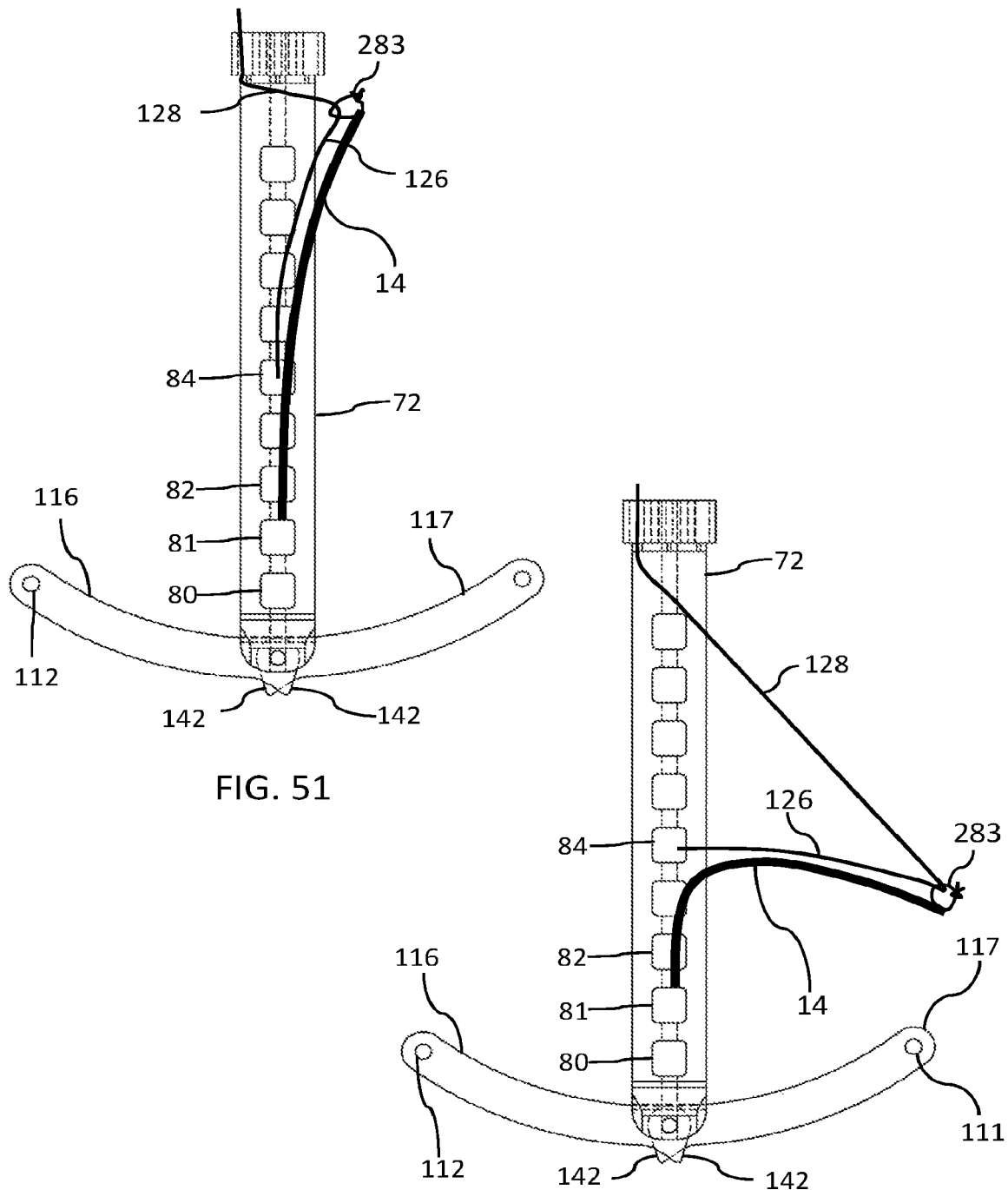
FIG. 51 shows an alternative schematic of the inner arm in a raised position.
FIG. 52 shows an alternative schematic of the inner arm in a lowered position.

FIGS. 51-52 show the schematics of inner arm 14 in various positions. In contrast to previous configurations, suture segment 128 is now looped through a suture loop 283 of inner arm 14 instead of inner arm 12 such that suture segment 128 manipulates the opposite arm. This criss-crossed configuration allows for more aggressive raising of the inner arms. As can be further seen in this configuration, suture segment 126 is looped through feature 84 of release bar 72. This configuration reduces friction on the sutures when manipulating the inner arms. Further, the suture segment is away from the tissue interfacing/gripping side of the inner arm, to further mitigate the risk of suture entanglement.

Figure 53:
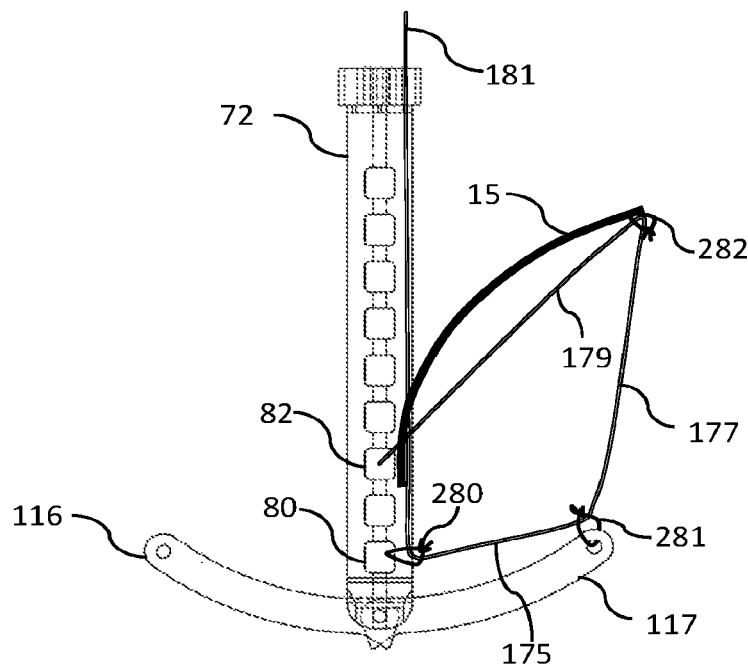
FIG. 53 shows an alternative schematic of the curved outer arm in a tissue grasping position.
Figure 54:
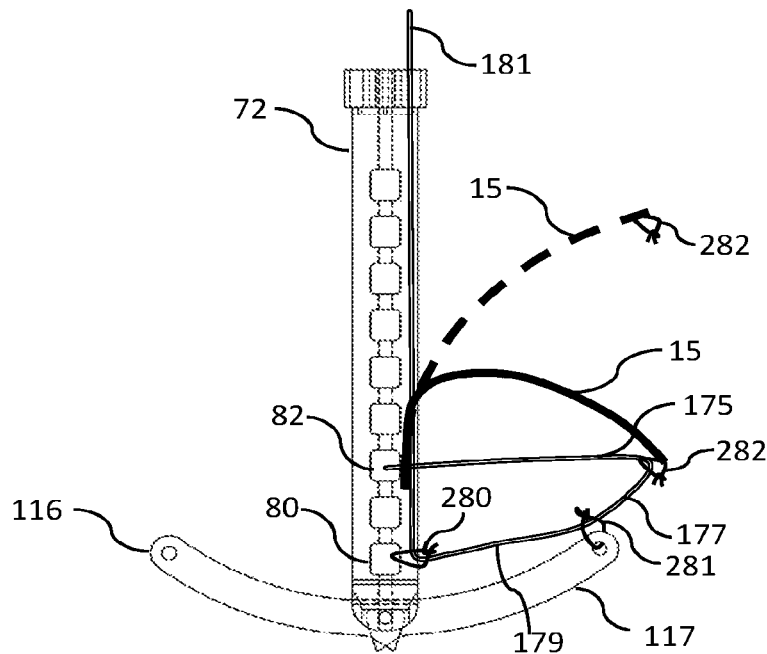
FIG. 54 shows an alternative schematic of the outer arm in an inverted position.

FIGS. 53-54 show the schematic of outer arm 15 in various positions. As can be seen, the suture is positioned such that the manipulation of outer arm 15 utilizes feature 82 of release bar 72, thereby reducing tension placed on the sutures when manipulating the outer arms. In this configuration, outer arm 15 is manipulated by threading suture 181 through suture loop 280 at feature 80, suture segment 175 through suture loop 281 and suture segment 177 through suture loop 282.

Figure 55:
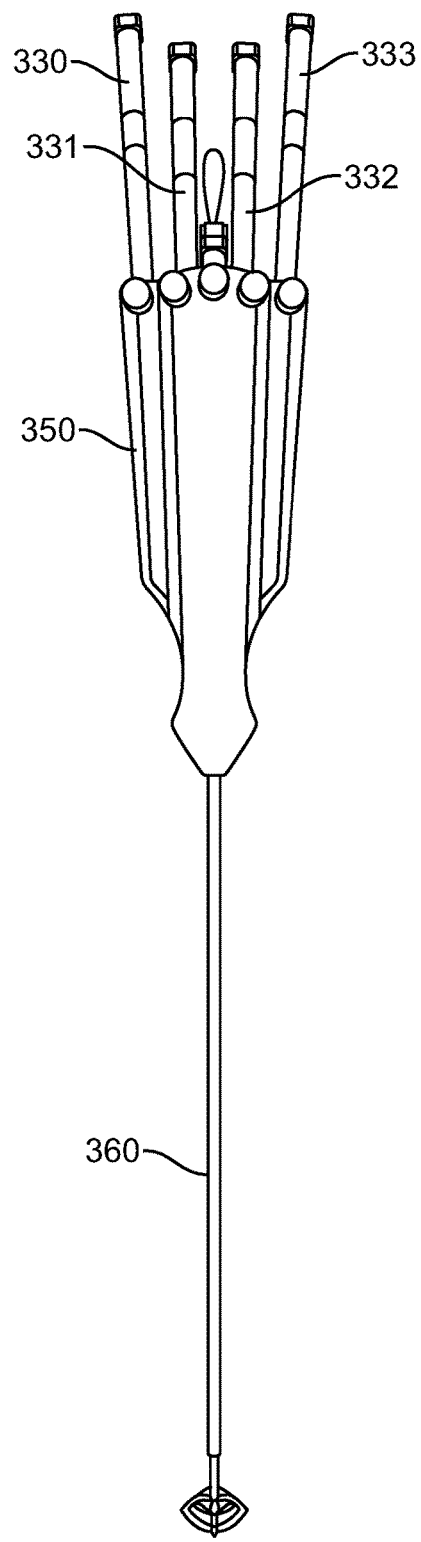
FIGS. 55-57 show photographic images of a prototype depicting an exemplary embodiment of a short delivery system.

FIG. 55 shows an image (front view) of the prototype depicting an exemplary embodiment of short delivery system for trans-thoracic approaches. As can be seen in this image, actuation-rods 330, 331, 332, and 333 are inserted in handle 350 to allow manipulations of outer arm 13, inner arm 14, inner arm 12 and outer arm 15, respectively. The stainless steel tube 360 is easily deformable, so the user can bend it as required to gain better access to the valve.

Figure 56:
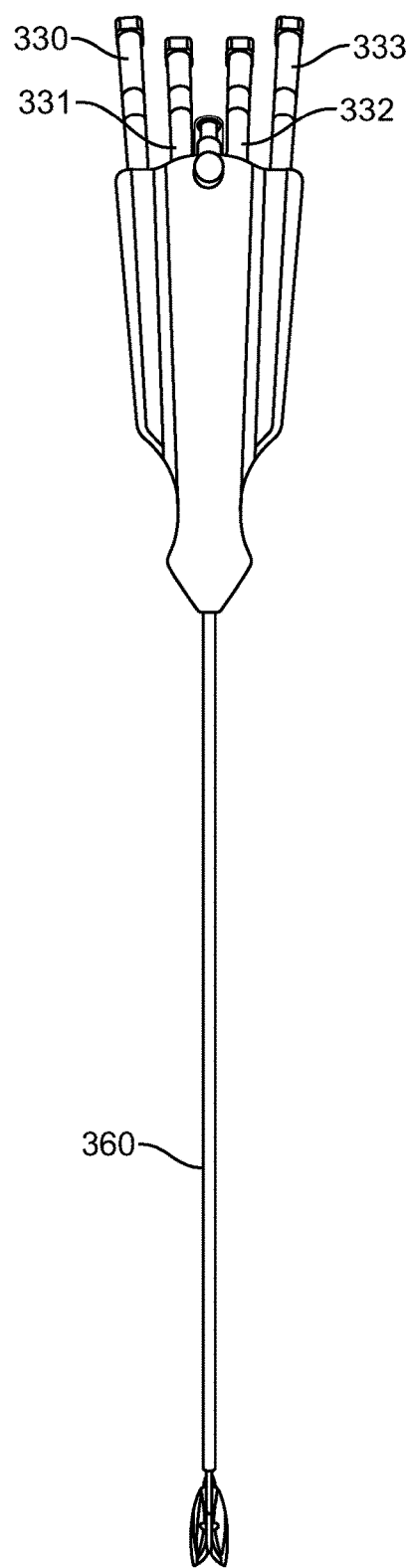

FIG. 56 shows an image (back view) of the prototype described in FIG. 55.

Figure 57:
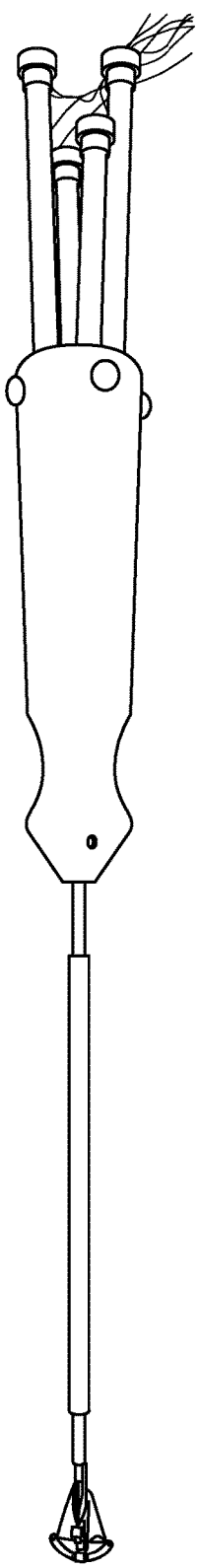

FIG. 57 shows an image of the prototype depicting an alternative embodiment of the delivery system, wherein handle 350 is largely cylindrical and/or conical in shape.

FIG. 58 shows an image of a preferred straight prototype, wherein the fixation device (back view) covered in fabric. As can be seen in this image, sutures controlling the outer arms are inserted through the back of the release bar. This reduces contact between sutures controlling the inner arms, thereby reducing friction between the sutures.

FIG. 59 shows an image of the prototype shown in FIG. 58, wherein the fixation device (side view) is covered in polyester fabric.

FIG. 60 shows an image of the prototype shown in FIG. 58, wherein the fixation device (front view) is covered in polyester fabric.

Figure 61:
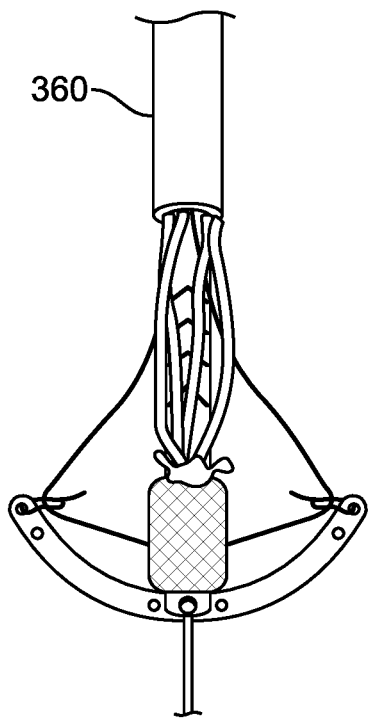
FIGS. 61-64 show photographic images of a straight prototype in different configurations of relaxed and biased positions.

FIG. 61 shows an image of the prototype shown in FIG. 60, with inverters deployed.

Figure 62:
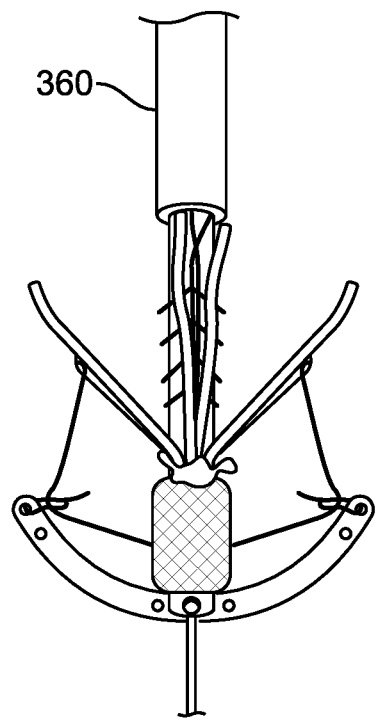

FIG. 62 shows an image of the prototype with the outer arms in a preferred leaflet grasping angle/position, while the inner arms remain raised.

Figure 63:
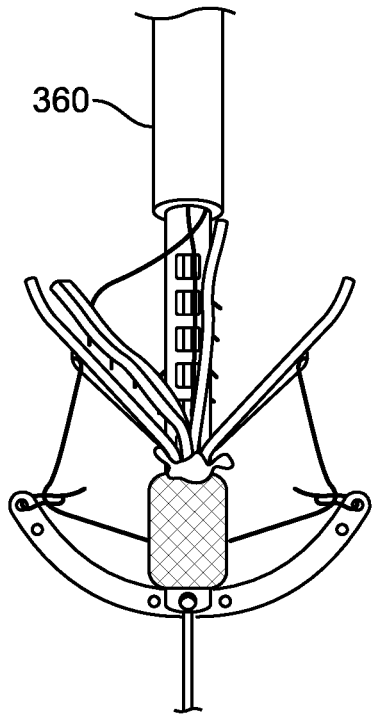

FIG. 63 shows an image of the straight prototype with the outer arms in preferred grasping angle, while the left inner arm is lowered. If a leaflet were to be in between the inner and outer arm, the leaflet would be captured by the inner arm in this configuration.

Figure 64:
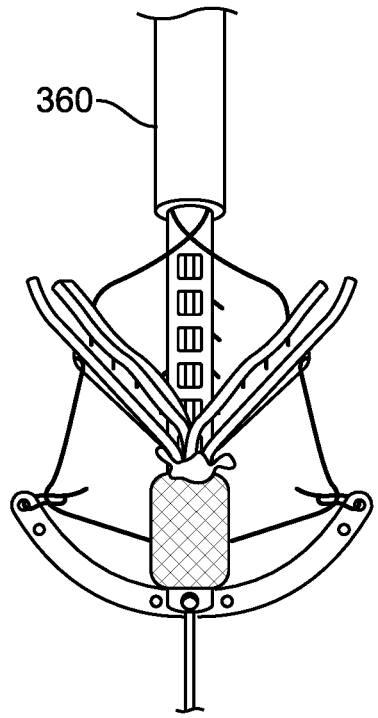

FIG. 64 shows an image of the prototype with both outer arms and inner arms in grasping position, such that any tissue or leaflets in between the arms would be grasped.

Figure 65A:
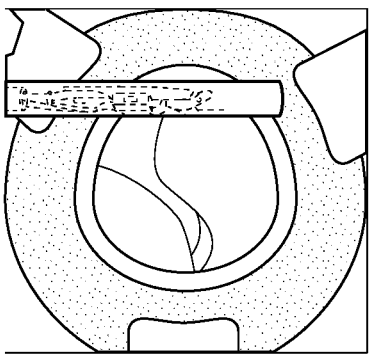
FIG. 65, Panels A-L, show photographic images of a straight prototype during a bench testing.
Figure 65B:
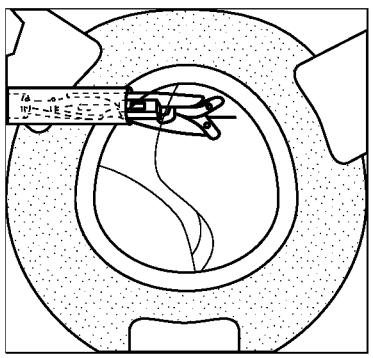
Figure 65C:
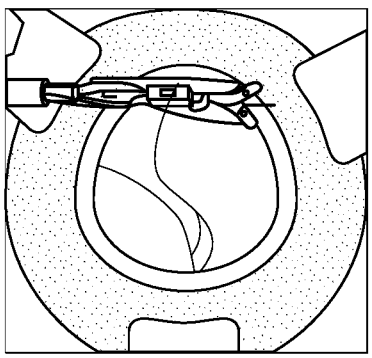
Figure 65D:
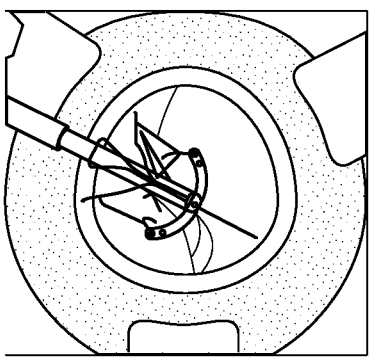
Figure 65E:
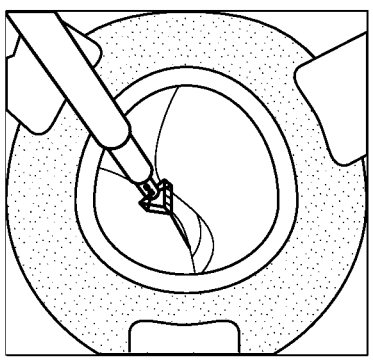
Figure 65F:
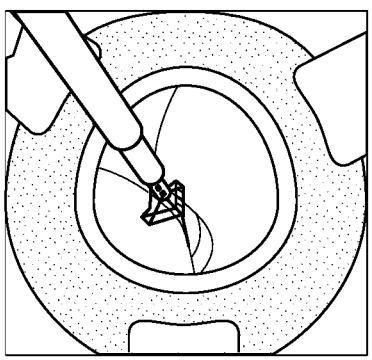
Figure 65G:
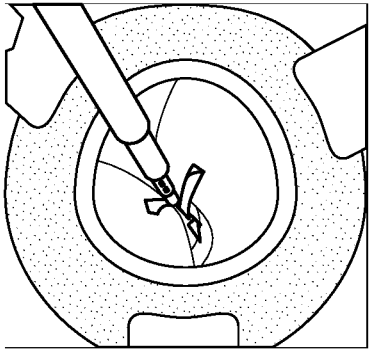
Figure 65H:
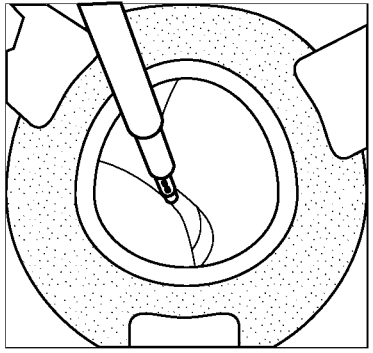
Figure 65I:
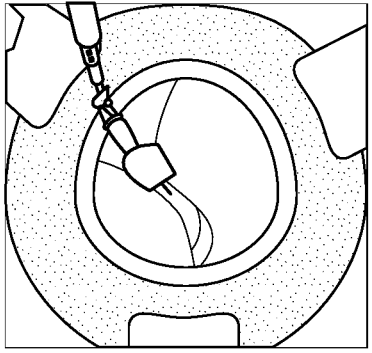
Figure 65J:
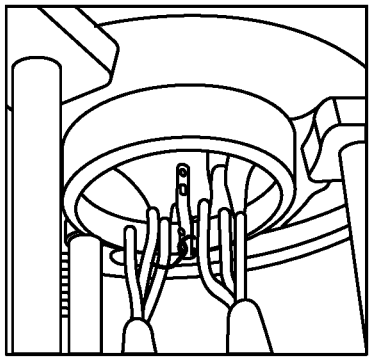
Figure 65K:
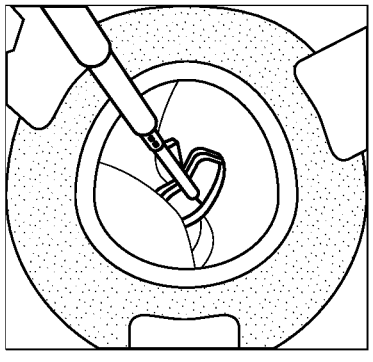
Figure 65L:
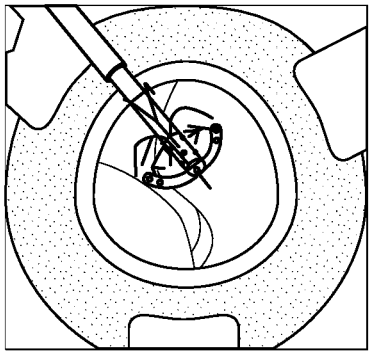

FIGS. 65A-65C show images of a preferred method of deployment of a straight device prototype, as it is advanced through a clear shaft representing a 12 Fr guide catheter. FIG. 65A) Device inside a 12 Fr shaft. FIG. 65B) Device being advanced out of the 12 Fr shaft. FIG. 65C) Device exposed. FIG. 65D) Device Outer Arms are lowered to grasping angle. FIG. 65E) Leaflets stabilized by Outer Arms. FIG. 65F) One side leaflet is grasped by dropping one of Gripper Arms. FIG. 65G) Second leaflet grasped by lowering the other gripper. FIG. 65H) Both Outer Arms are raised. FIG. 65I) The device is fully deployed. FIG. 65J) View of device from ventricular side. FIG. 65K and FIG. 65L) Bailout position showing raised Grippers and inverted Outer Arms.

Figure 66A:
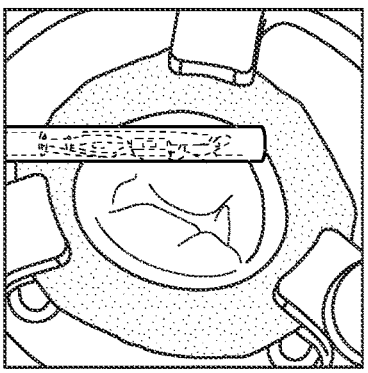
FIG. 66, Panels A-J, show alternative photographic images of a curved prototype during bench testing.
Figure 66B:
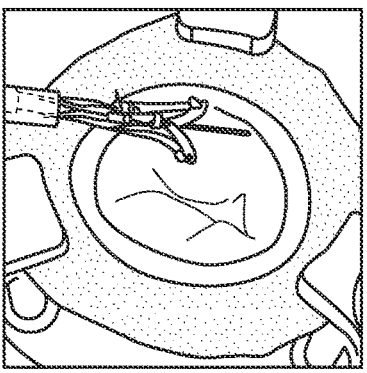
Figure 66C:
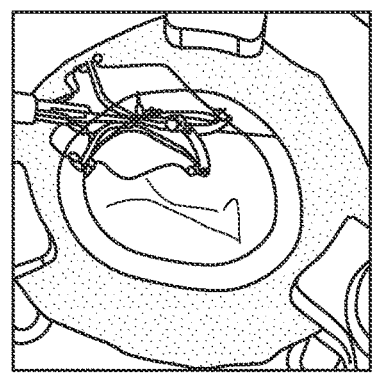
Figure 66D:
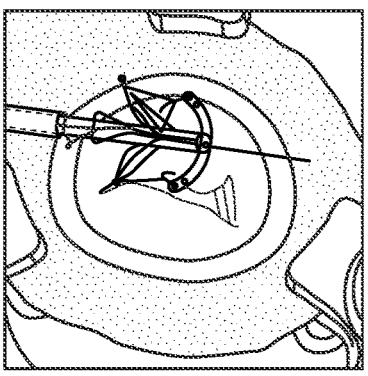
Figure 66E:
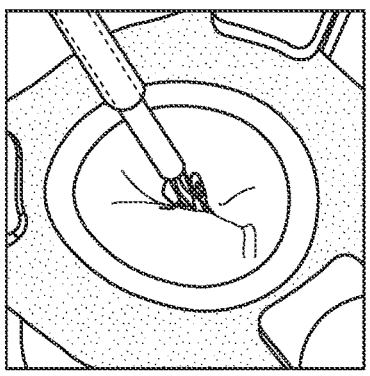
Figure 66F:
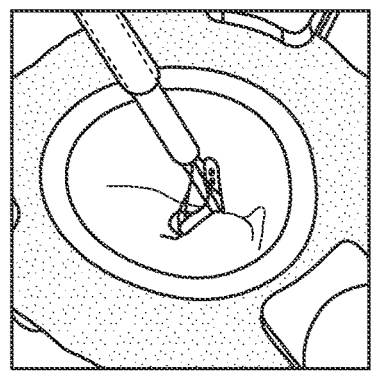
Figure 66G:
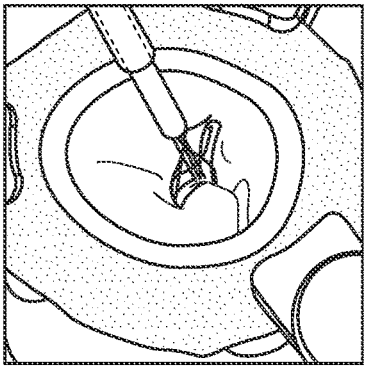
Figure 66H:
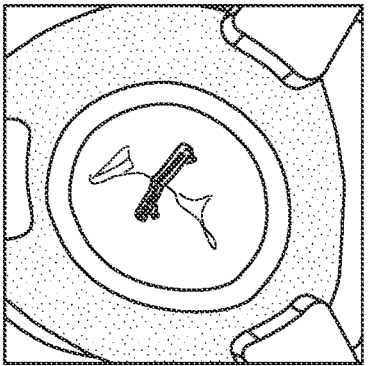
Figure 66I:
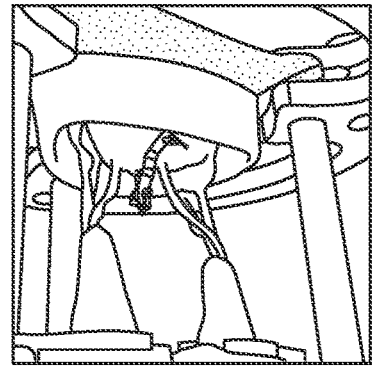
Figure 66J:
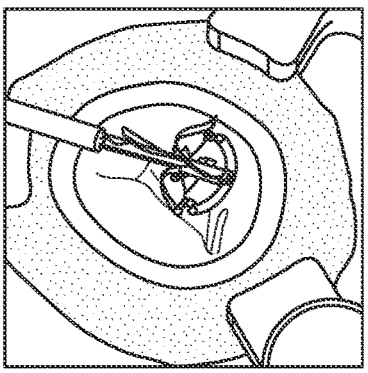

FIGS. 66A-66J show images of a preferred curved prototype during bench testing. FIG. 66A) Device inside a 12 Fr shaft. FIG. 66B) Device being advanced out of the 12 Fr shaft. FIG. 66C) Device exposed. FIG. 66D) Device Outer Arms are lowered to grasping angle. FIG. 66E) Leaflets stabilized by Outer Arms. FIG. 66F) One side leaflet is grasped by dropping one of Gripper Arms. FIG. 66G) Second leaflet grasped by lowering the other gripper. FIG. 66H) the device is fully deployed. FIG. 66I) View of device from ventricular side. FIG. 66J) Bailout position showing raised Grippers and inverted Outer Arms.

Figure 67:
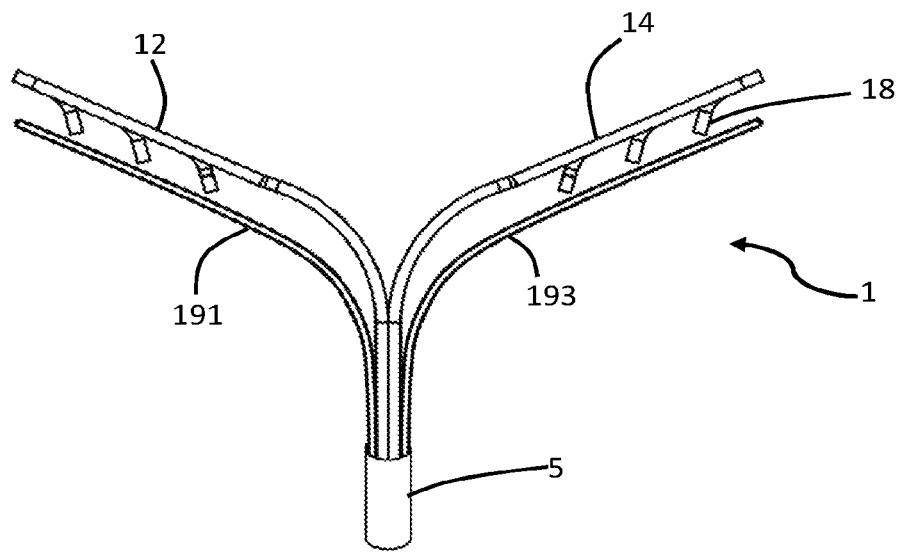
FIG. 67 shows an exemplary embodiment of the fixation device (front view).

FIG. 67 shows an exemplary embodiment of a curved fixation device. Inner arms 12 and 14 comprise of a plurality of barb-like protrusions 18. As can be seen in the 3D view of the device in FIG. 68, the inner arms 12, 14 are made of sheet metal while the outer arms 191, 193 are made of wire loops.

FIG. 69A shows an exemplary embodiment of the fixation device, wherein inner arms 192, 194 and outer arms 195, 197 are comprised of single primary loop of metal wire, such as Nitinol. Inner arm 192 further comprises of band 250, which is used to affix the metal wires together and small wire loops 252 to pass actuating sutures through. These small suture loops 252 provide a localized attachment point at the arm.

FIG. 69B illustrates a method of assembling nested wire loops to form either inner or outer arms that are optionally held together by bands 250. The nested loops may be of a single wire or multiple wires.

Figure 68:
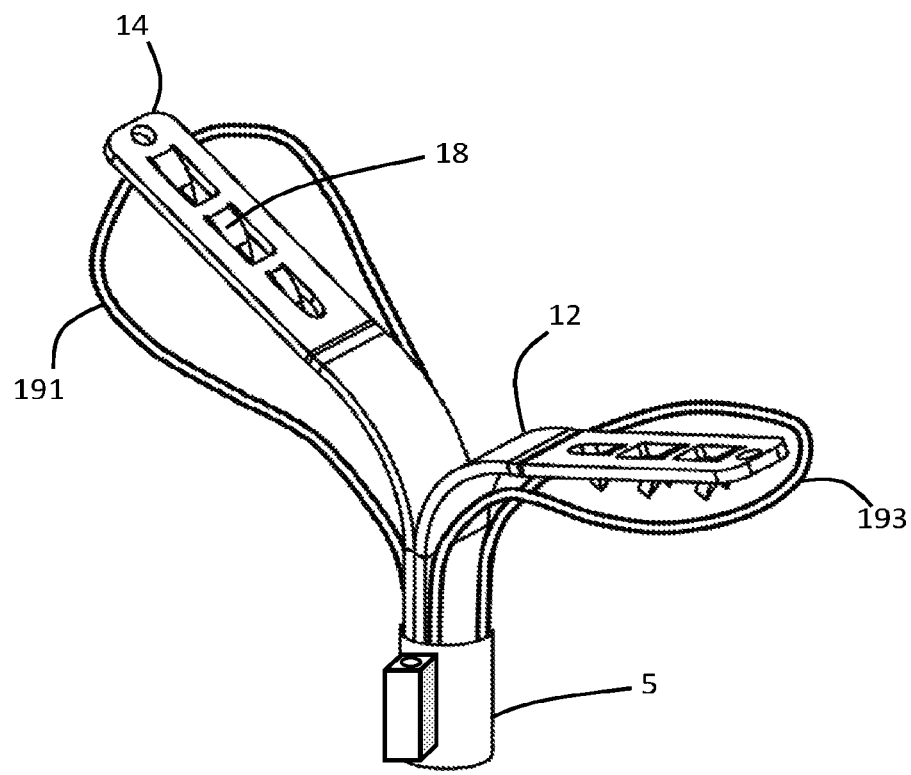
FIG. 68 shows 3D view of the embodiment of the fixation device shown in FIG. 67.

FIG. 70 shows an exemplary schematic of the curved fixation device as in FIG. 68. Further, it demonstrates the configuration in which the fixation device is affixed onto release bar 72. As can be seen, suture 130 controls inner arm 14 instead of inner arm 12 in previous configurations. Similarly, suture 131 controls inner arm 12. This configuration allows for improved raising angle of the inner arms. Suture segments 125, 126 are looped around release rod 160 through feature 85, which is well spaced and away from the tissue interfacing gap of the arms. Additionally, sutures 180, 181 control outer arms 191, 193, respectively. Suture segments 175, 175 of sutures 180, 181 are looped around release rod 160 through feature 82, which is well below and away from the tissue interfacing gap between the two arms. A advantage of this invention is reduced contact between sutures 125, 126 and sutures 174, 175, thereby reducing friction and tangling between the sutures. Moreover, this separation improves manufacturability.

Figure 71A:
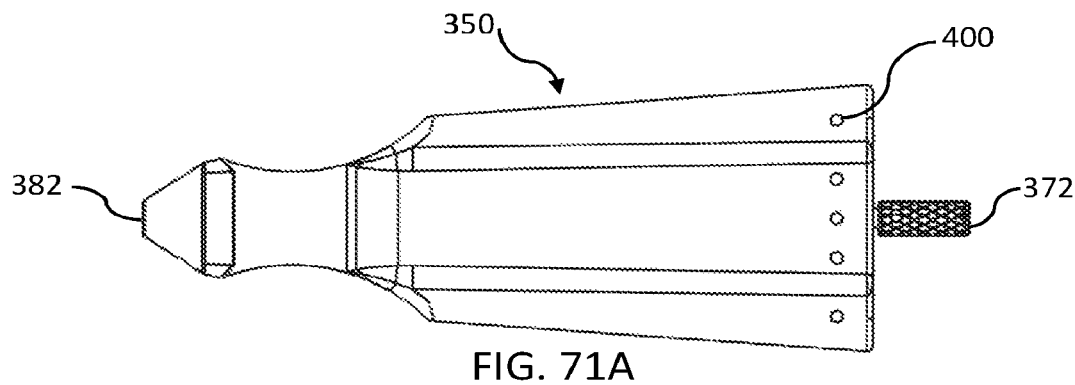
FIGS. 71A and 71B show alternative embodiments of the catheter handle.
Figure 71B:
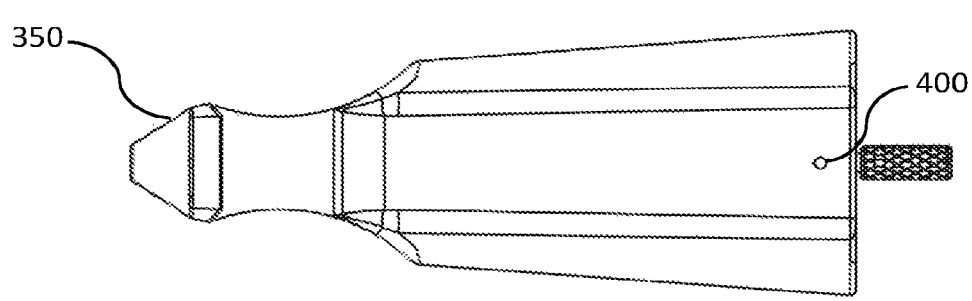

FIGS. 71A and 71B show alternative embodiments of catheter handle 350. Release knob 372 controls release rods 160. Feature 400 allows screws to be placed in order to affix actuation-rods 330, 331, 332, 333 to catheter handle 350 to reduce the possibility of unintentional movement during surgical procedures. This, in addition to the friction provided by the O-rings of the handle.

Figure 72:
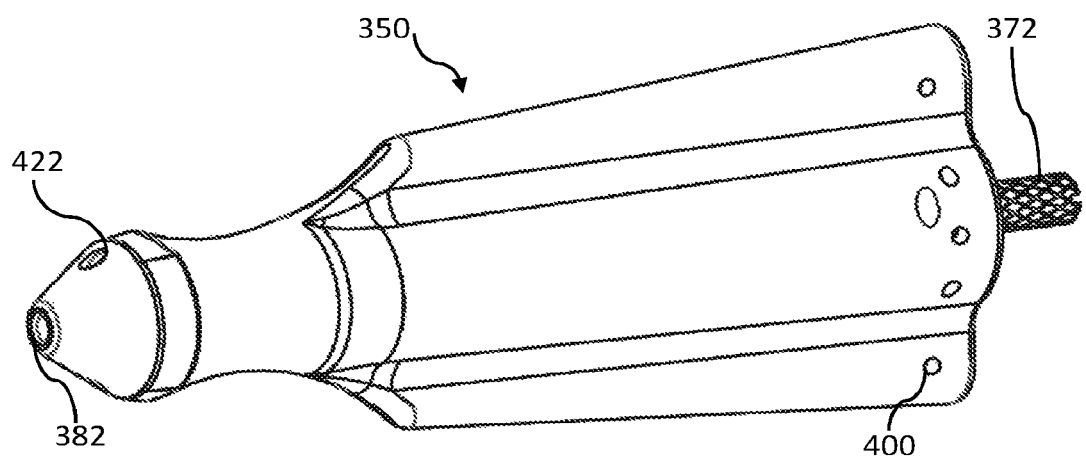
FIG. 72 shows a 3D view of the catheter handle shown in FIG. 71.

FIG. 72 shows an alternative view of catheter handle 350. Feature 422 allows set screws to fasten the stainless-steel tube 360 to the nozzle 382.

Figure 73:
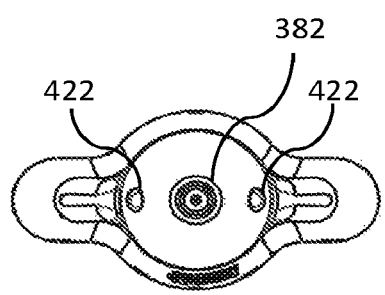
FIGS. 73-75 illustrate various views of catheter handle 350.

FIG. 73 illustrates the front view of catheter handle 350, depicting nozzle 382 and features 422.

Figure 74:
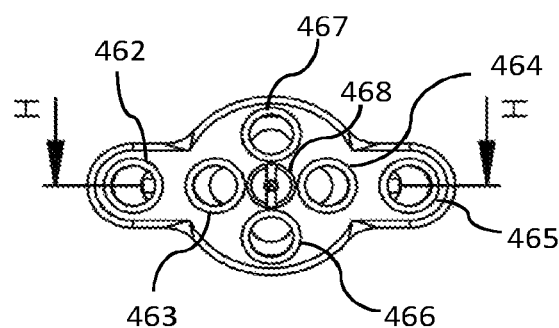

FIG. 74 illustrates the back view of catheter handle 350. Features 462, 463, 464, 465, 466 allow the insertion of actuation-rods 333, 332, 331, 330, respectively. Alternatively, the actuation-rods can be inserted through features 467 and 468, or any combination of features 462, 463, 464, 465, 466, 467, 468 to actuation-rods 330, 331, 332, 333. Moreover, features 467 and 466 may be used as flush ports to flush saline, insert sensors and actuators and/or insert actuation rod for bailout suture 602.

Figure 75:
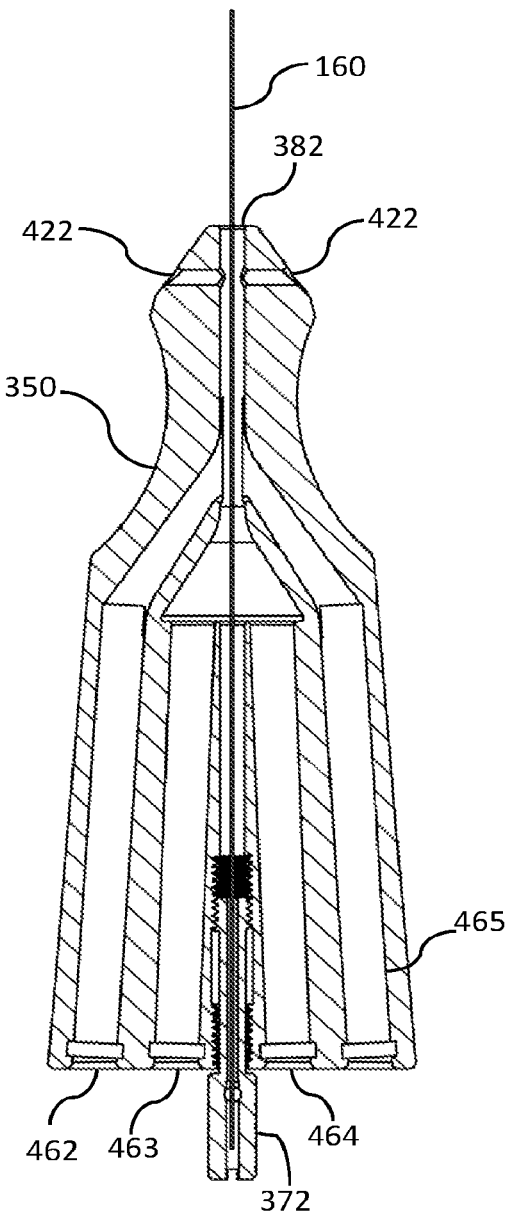

FIG. 75 illustrates a cross-sectional drawing of the exemplary catheter handle 350. Features 462, 463, 464, 465 allow the smooth insertion of actuation-rods 333, 332, 331, 330, respectively. Further, the acute angles in which channels 462, 463, 464 and 465 may taper to allow guidewires, sutures plastic tubes and/or metal tubes from kinking and/or tangling.

FIG. 76 illustrates an exemplary method of manipulating release rod 160 to decouple the fixation device from the release bar. Release rod 160 is controlled by release knob 372 via threaded features 500 and 502. Threaded features 500 and 502 prevents unintentional removal of release rod 160 as the release knob 372 needs to be unscrewed prior to retraction. To improve speed of unscrewing and to limit amount of retraction, there is a designed gap/slot between the threads 502 and 500. In an exemplary and preferred embodiment, unscrewing release knob 372 from threaded feature 502 and retracting the knob until threaded feature 500 decouples straight fixation devices, from release bars 70 and 72. In an alternate and preferred embodiment for curved devices, unscrewing release knob 372 from threaded features 502 and retracting it up to feature 500 only partially decouples the device from release bar 70 and 72, wherein, the bailout sutures will still remain attached at feature 88. This allows for the device to be retracted back into the guide catheter. However, if complete deployment is desired (as in case of successful grasping of tissue) the release knob 372 must be removed all the way out of both distal 502 and proximal 500 threads.

Figure 76A:
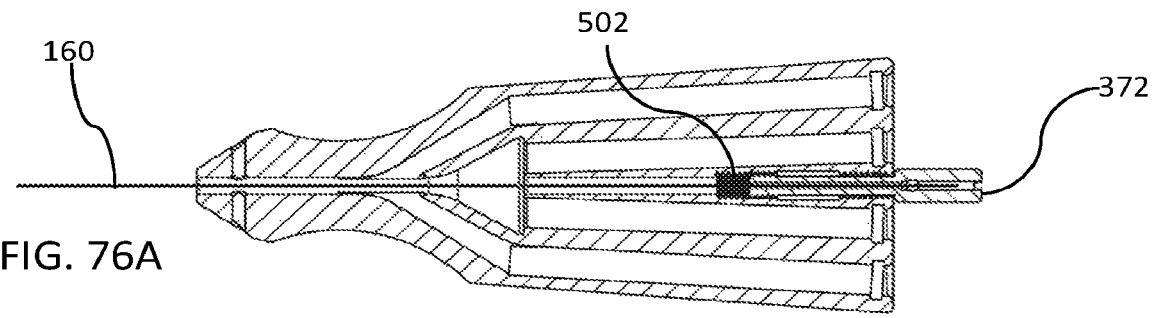
FIGS. 76A-76D illustrates the section views of handle 350 in various configurations for manipulating the release rod 160, using release knob 372.
Figure 76B:
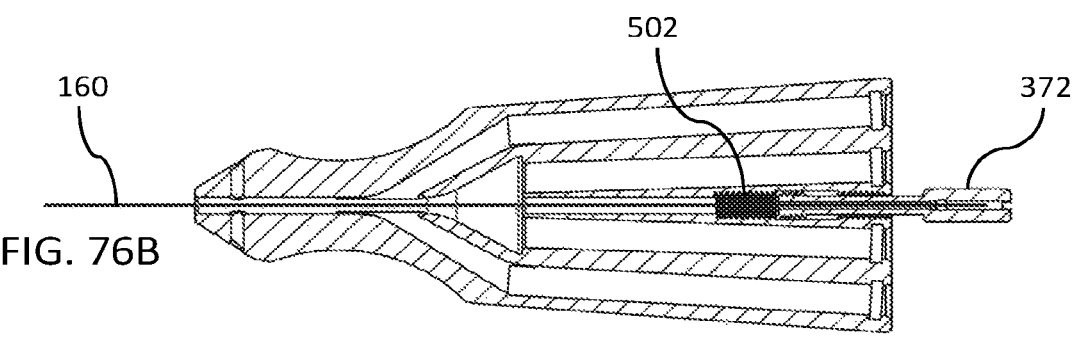
Figure 76C:
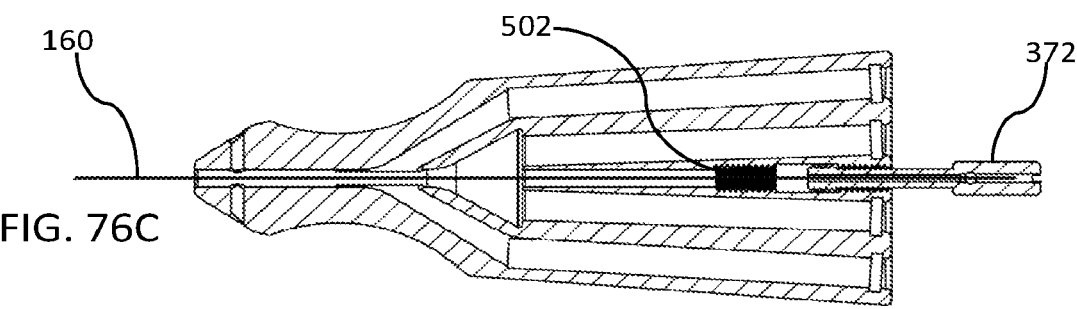
Figure 76D:
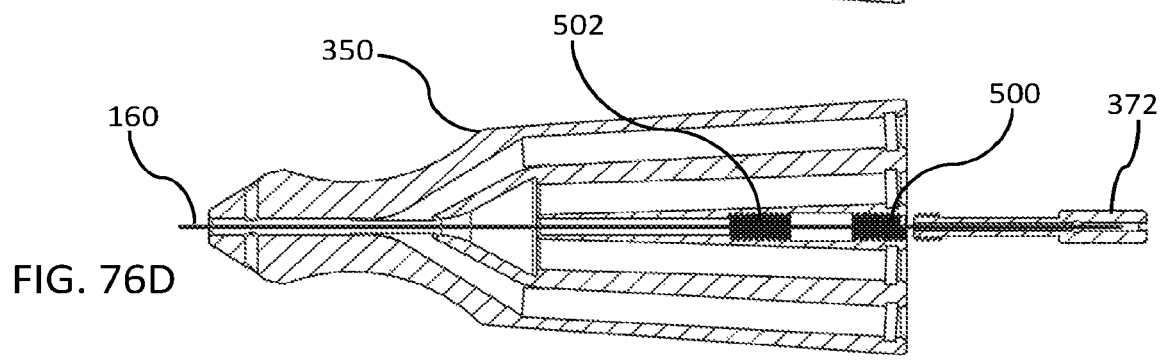

As seen in FIG. 76A, the release rod 372 is completely inserted, representing a loaded device. To deploy the device, the user first unscrews the release knob 372 as shown in FIG. 76B and retracts it partially through the non-threaded slot between the two threads 502 and 500 as shown in FIG. 76C. Based on the suture attachment points (for example, between 80-85), preferably straight devices can be configured to be released and deployed. To further retract the release rod 160 (for example, through 86-88), the user may optionally unscrew the release knob out of the proximal threads 500. For example, curved devices may be configured to have a bailout suture in the feature 88. Hence, to deploy a curved device in leaflets, the user will need to fully remove the release knob 372 out of the handle body, as shown in FIG. 76D.

Figure 77:
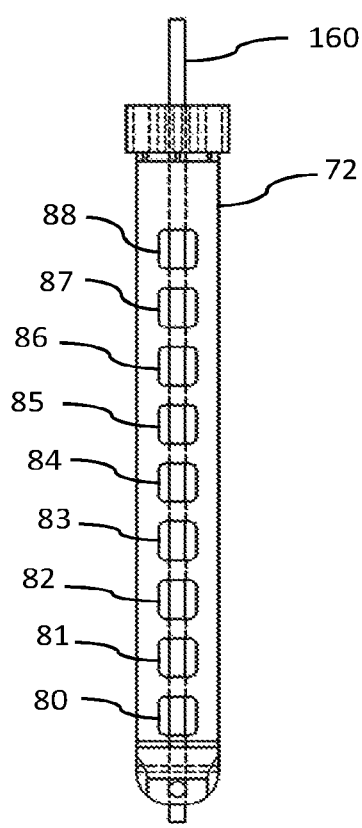
FIG. 77 shows the release rod in a loaded configuration.

FIG. 77 shows release rod 160 completely inserted in release bar 72. As can be seen, release rod 160 is inserted through features 80-88. Further, it is exposed at the distal end of release bar 72.

Figure 78:
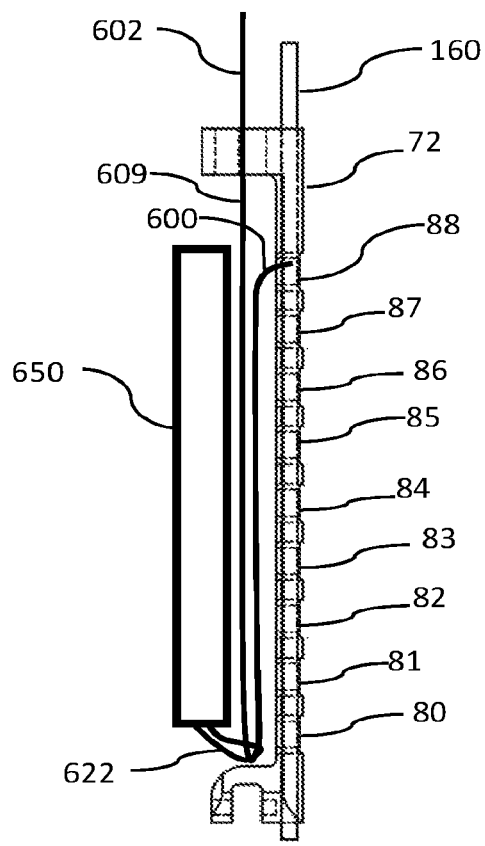
FIG. 78 shows the schematic of a curved device attached to a release bar 72 in a loaded configuration, showing bailout sutures only.

FIG. 78 shows the schematic of curved device 650 attached to release bar 72 in a loaded configuration, wherein release rod 160 is completely inserted through the release bar. As can be seen, curved device 650 has suture loop 622 which allows suture 600 to affix the device to release bar 72 through feature 88. Note, for simplicity, other sutures to actuate the arms are not shown.

Figures 79, 80, 81:
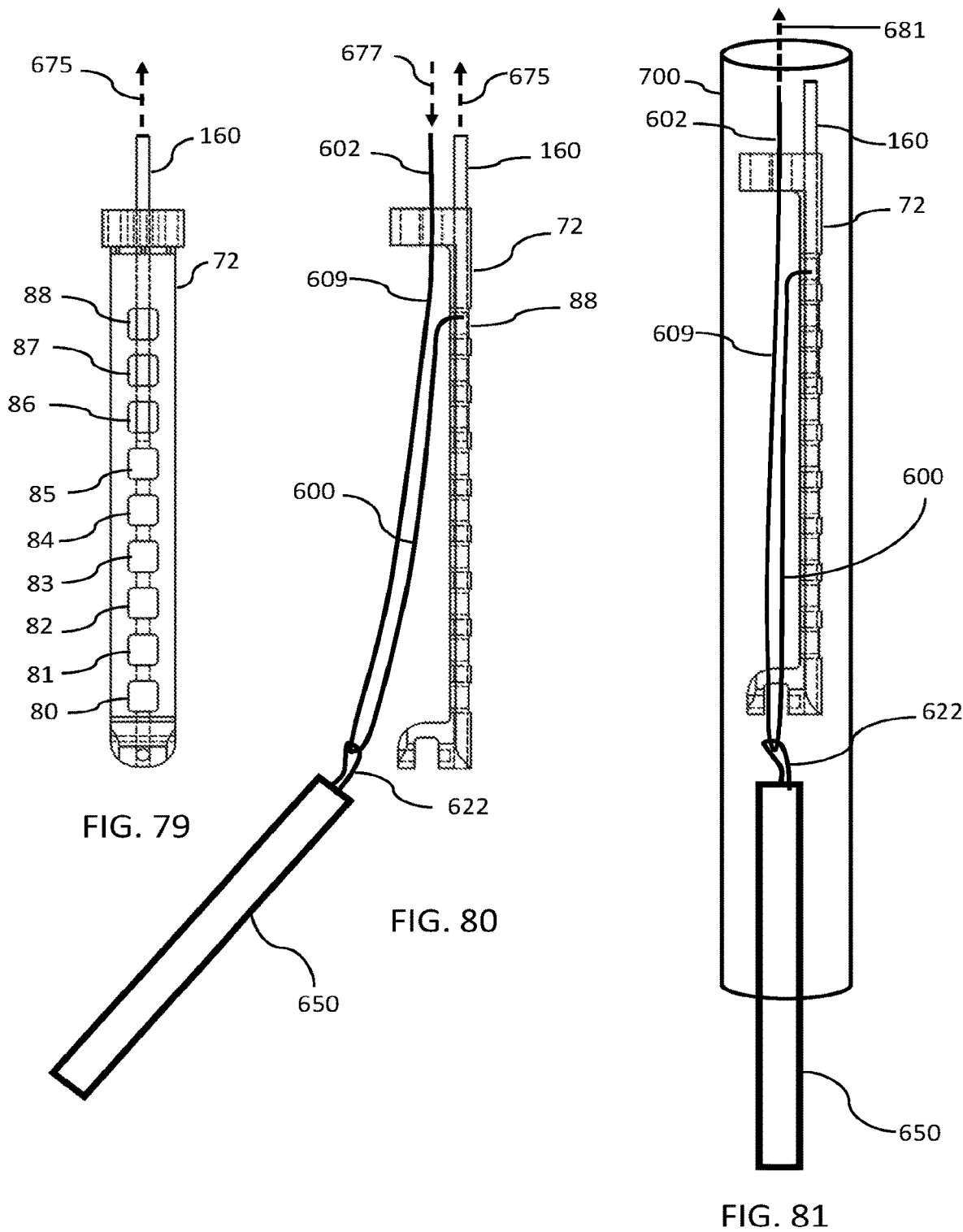
FIG. 79 illustrates the schematic of a release rod that is partially removed from the release bar.
FIG. 80 shows the schematic of a curved device in an inverted orientation and distal from the release bar 72 with the release rod 160 partially retracted.
FIG. 81 shows an inverted curved device retracted inside a catheter with a partially retracted release rod.

FIG. 79 illustrates the schematic of release rod 160 that is partially retracted (corresponding to FIG. 76C), as indicated by arrow 675, from release bar 72 such that features 80-85 are free. Subsequently, FIG. 80 shows the schematic of curved device 650 partially detached from release bar 72 as release rod 160 is partially retracted. Consequently, curved device 650 is in an inverted position with the bailout suture at feature 88 still coupled to suture loop 622 of curved device 650. Thus, allowing for retraction and removal of the device 650 through the guide catheter 700, as shown in FIG. 81.

Figure 82:
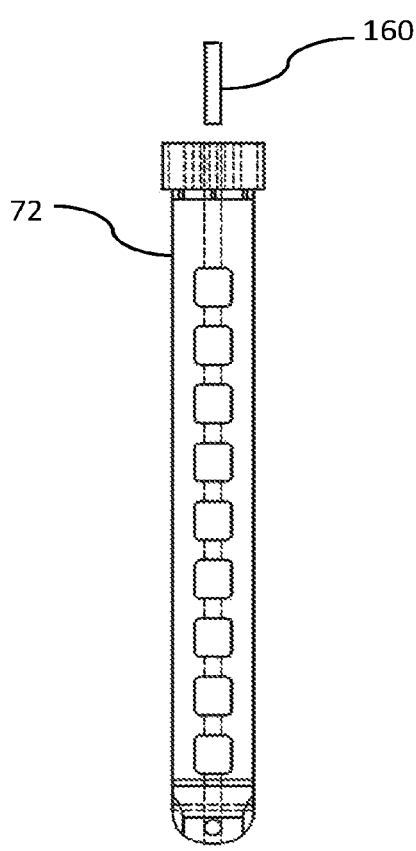
FIG. 82 illustrates the schematic of a release rod 160 that is completely removed from the release bar 72.

FIG. 82 illustrates the schematic of release rod 160 completely removed from release bar 72, freeing features 80-88 of sutures and fixation device.

Figure 83:
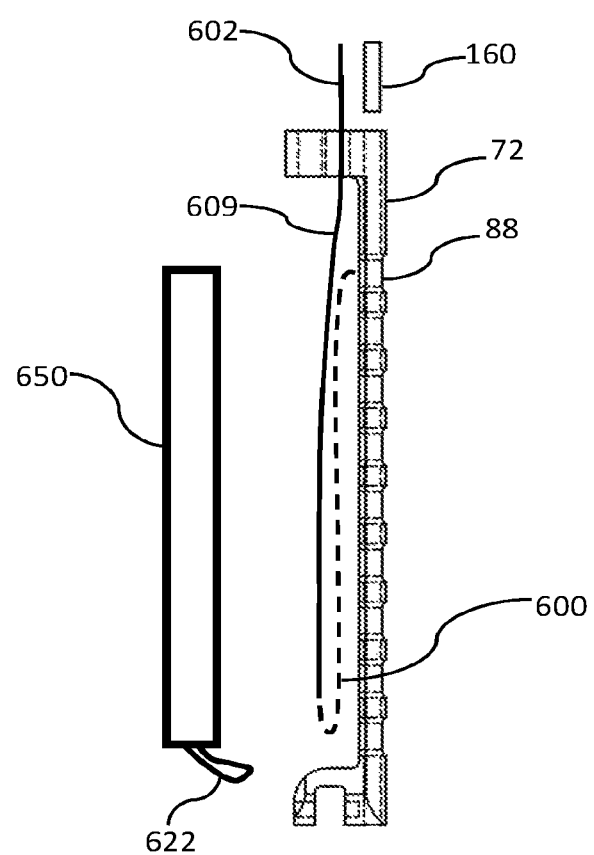
FIG. 83 shows a fully deployed curved device with the release rod 160 completely retracted from the release bar 72.

FIG. 83 shows the complete deployment of curved device 650 with release rod 160 completely removed from release bar 72 (corresponding to FIG. 76D). As such, suture 602 is freed from suture loop 622 and feature 88, thereby decoupling curved device 650 from release bar 72.

Figure 84A:
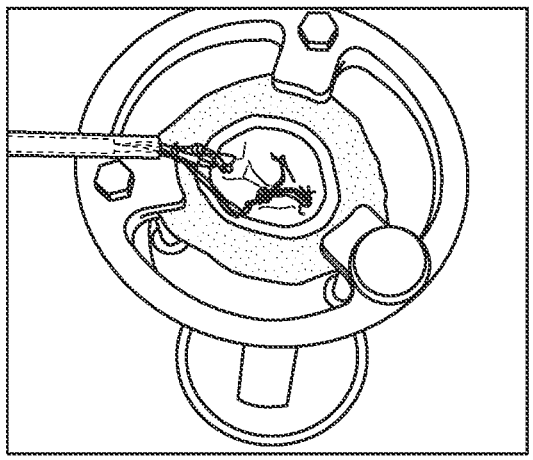
FIGS. 84A-84D show photographic images of the prototype, wherein the fixation device is partially deployed and inverted external to the catheter and then retracted completely inside the catheter.
Figure 84B:
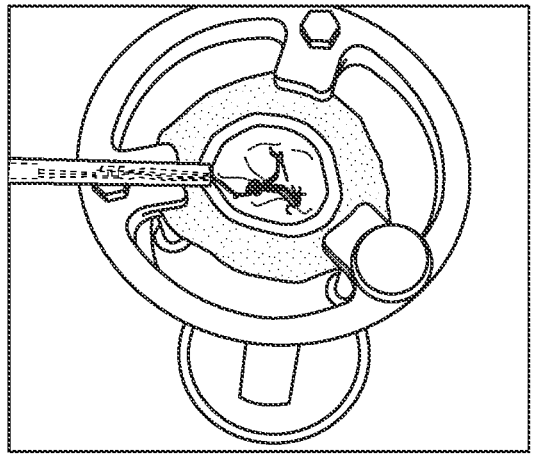
Figure 84C:
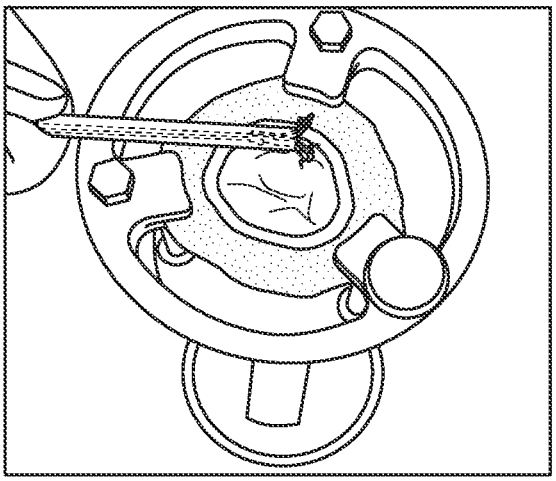
Figure 84D:
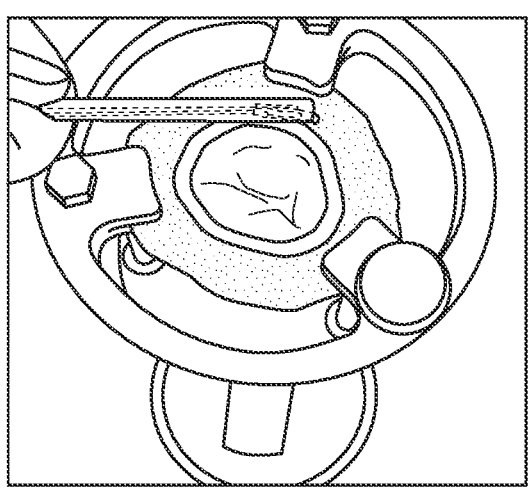

FIGS. 84A-84D shows images of an exemplary curved device prototype demonstrating the bailout method as described in FIGS. 76-83, wherein the fixation device is partially deployed but still attached to the deployment suture 600-609 (FIG. 84A). FIGS. 84B-84D show sequential steps of retraction of the device inside of an exemplary 12 F shaft.

Figure 85:
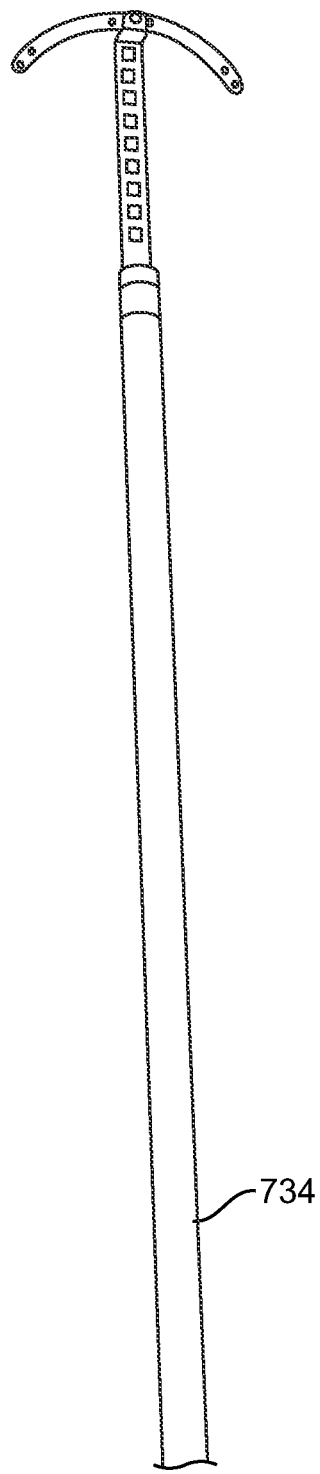
FIG. 85 shows a photographic image of the delivery system prototype sub-assembly showing release bar with tubes 734 attached to pass through actuating sutures.

FIG. 85 shows an image of the distal end of an exemplary delivery system sub-assembly of a short catheter (as shown in FIGS. 55-57).

Figure 86:
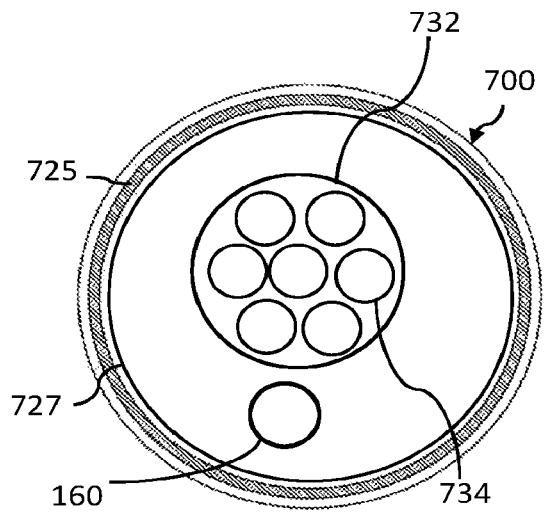
FIG. 86 shows a single lumen braided shaft with free-floating release rod 160 and freely floating shaft 732 encapsulating the tubes 734.

FIG. 86 shows a single-lumen braided shaft 700, wherein the release rod 160 is free-floating within the shaft. Optionally, shafts 734 are enclosed inside another free-floating single lumen shaft 732.

Figure 87:
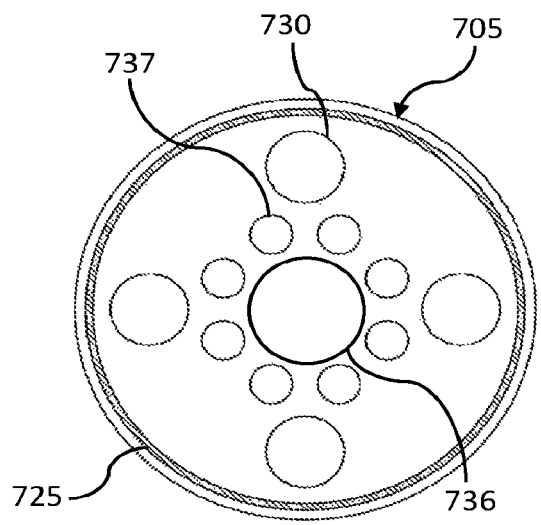
FIGS. 87-93 illustrate alternative configurations of multi-lumen braided shafts.

FIGS. 87-93 illustrate alternative configurations of multi-lumen braided shafts that may be used for a catheter. Metal wires, metal tubes, plastic tubes, pullwires and/or sutures can be inserted through the lumens 730, 734, 736, 737, 738, 739. Further, Nitinol wires may be inserted to strengthen or maintain stiffness of the catheter. In FIG. 87, in a preferred embodiment, actuating sutures are passed through the inner ring of lumens 737 and nitinol mandrels are optionally inserted in the larger lumens 730, 736, especially in the distal unsupported segment of delivery catheter shaft to maintain straightness of the shaft, as it extends out of the guide curves. The release rod is be passed through any of the larger loops 730, 736.

Figure 88:
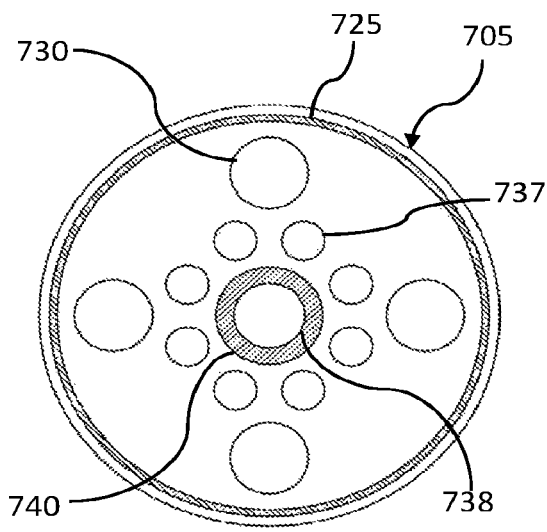

FIG. 88 shows an alternate embodiment of the shaft in FIG. 87, wherein a torque cable or peek tubing is bonded to the lumen 736 to improve the torque, tension, flexibility and compression characteristics of the catheter shaft.

Figure 89:
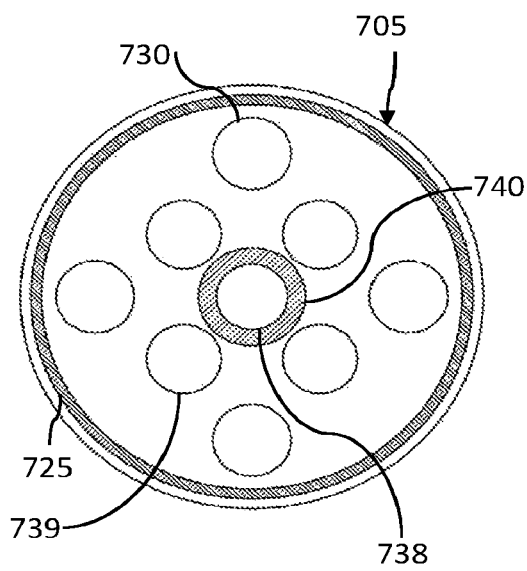

FIG. 89 shows an alternate embodiment of the shaft with torque cable and/or peek tubing.

Figure 90:
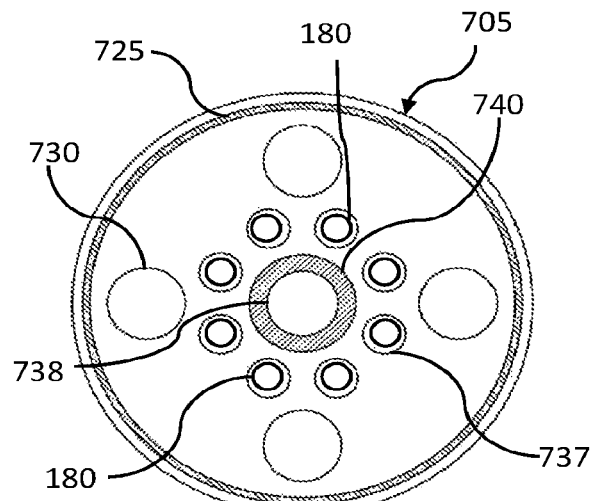

FIG. 90 shows the embodiment in FIG. 88, with sutures. As can be seen, each pair of suture strands can be passed through diametrically opposite lumens, as shown for example for suture 180. Such a configuration is preferred, as it balances the suture pull forces across the center of the catheter, to mitigate the pull force induced curving of the catheter.

Figure 91:
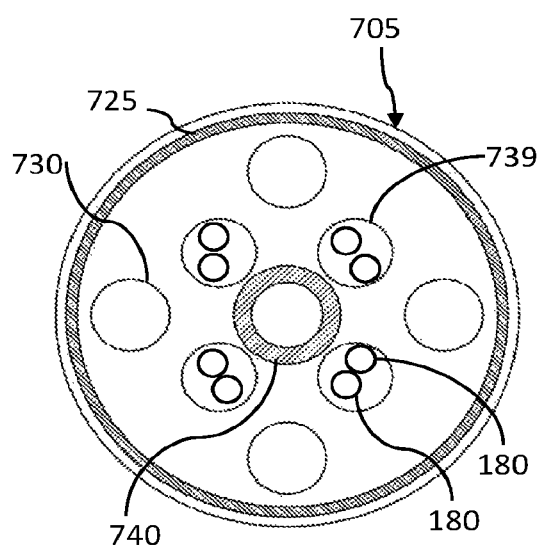

FIG. 91 shows the embodiment in FIG. 89, with sutures. As can be seen, each pair of sutures strands can be passed through same lumens.

Figure 92:
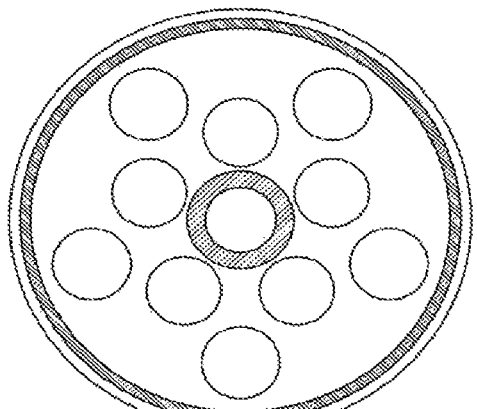
Figure 93:
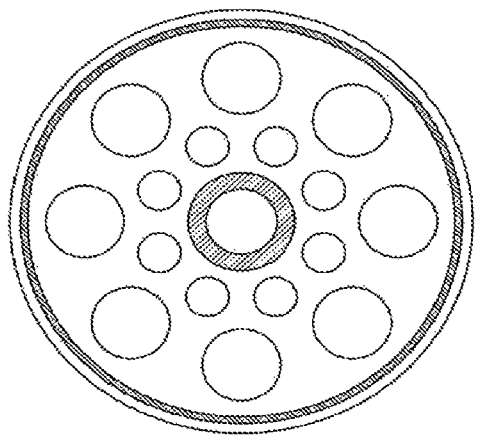

FIGS. 92 and 93 show alternate embodiments of the deliver shaft.

Figure 94:
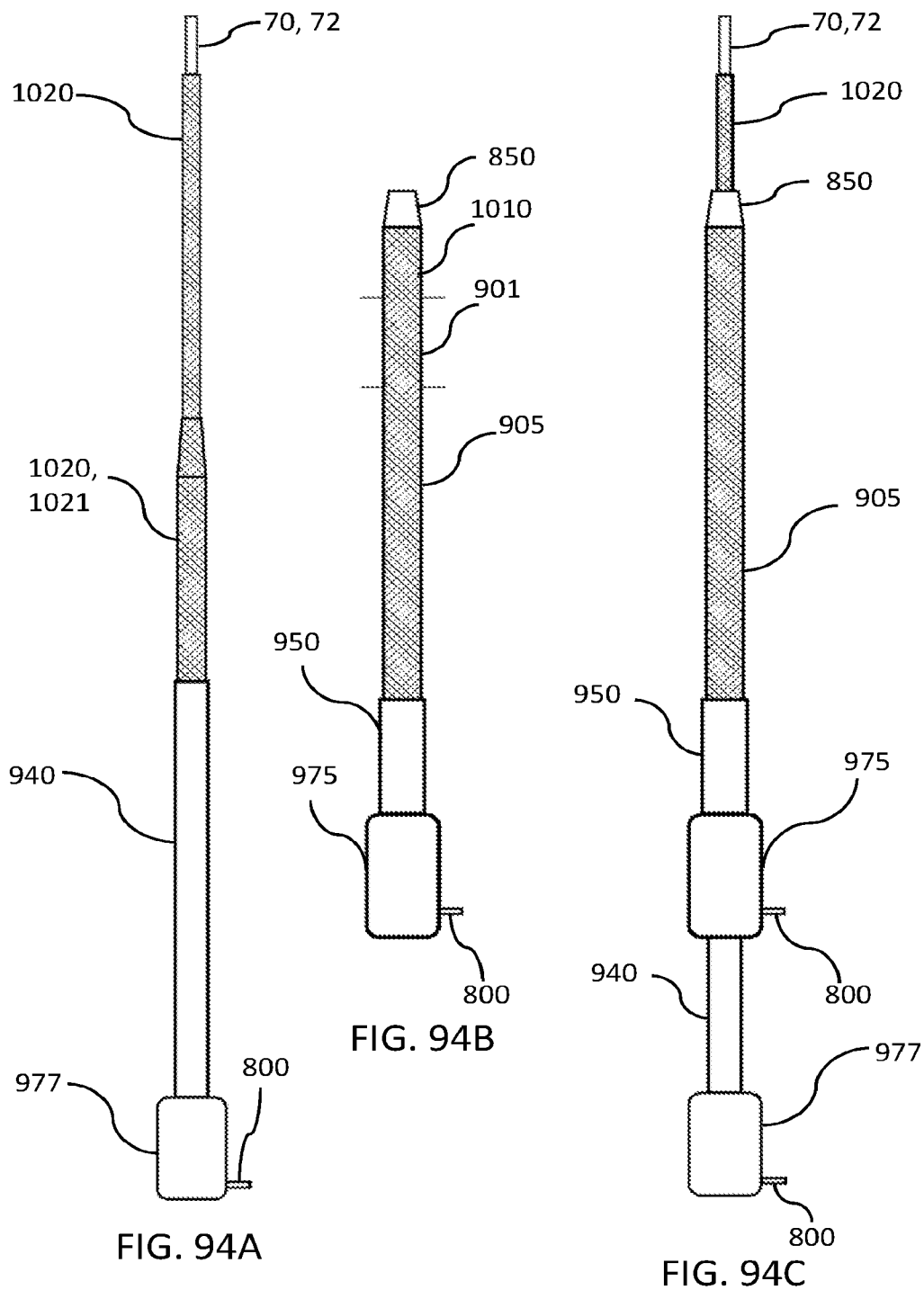
FIGS. 94A-94C illustrate exemplary schematic configurations of a two-nested catheter system.

FIGS. 94A-94C show schematic illustrations of an exemplary and preferred two-nested catheter system, as per this invention, respectively.

Figure 95:
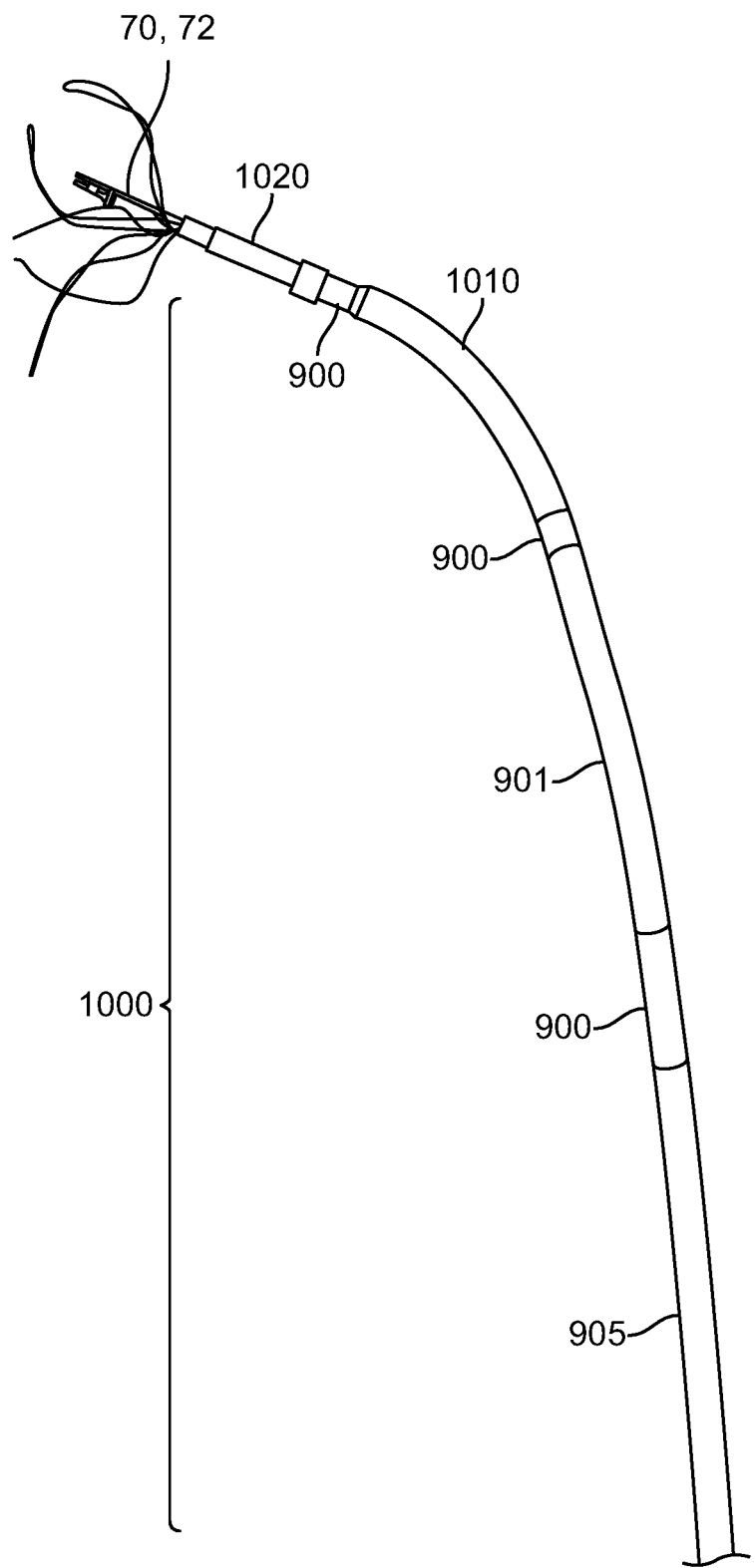

FIG. 95 shows an image of the distal segments of a preferred two-nested catheter system prototype. As can be seen, the exemplary 9 Fr outer diameter delivery catheter shaft 1020 passes through the lumen of the exemplary 12 Fr steerable guide catheter shaft 1000.

Figure 96:
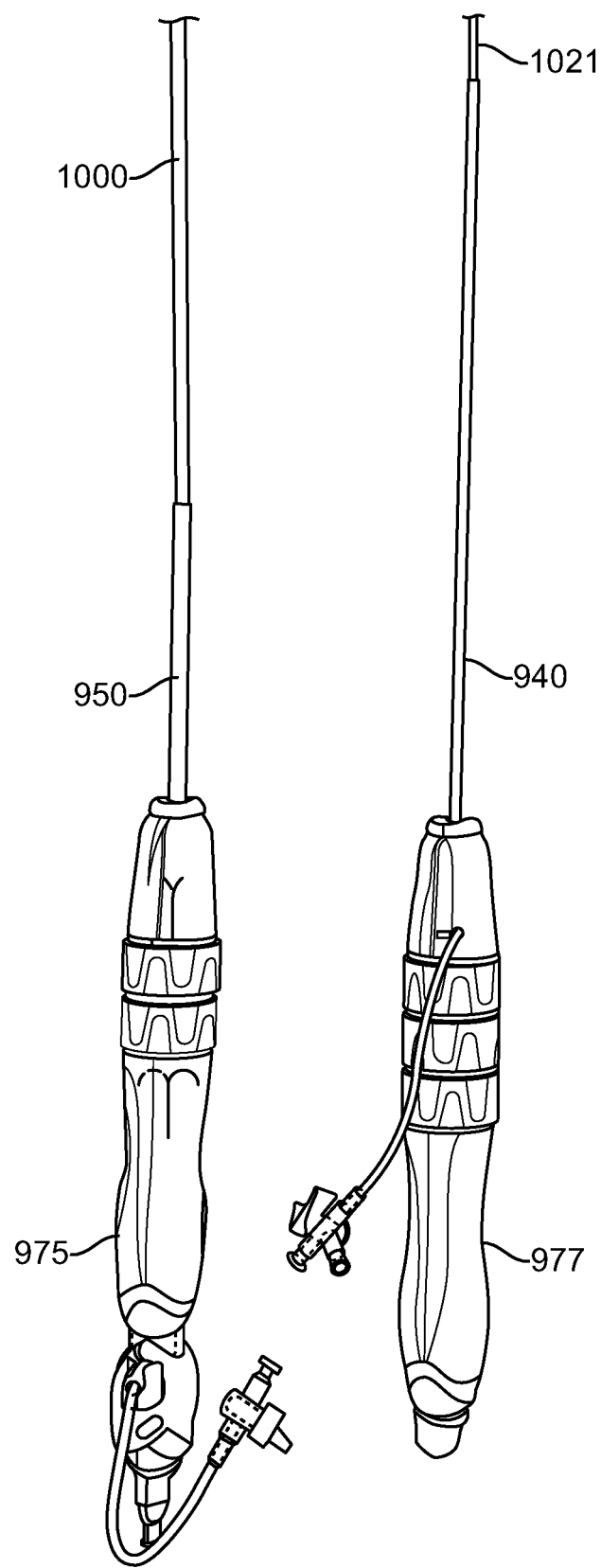

FIG. 96 shows an image of a preferred steerable guide and delivery catheter handles prototypes in a side-by-side view. The exemplary stainless-steel tube 950 provides a means to support and attach the steerable guide catheter handle on to a suitable stand (not shown). And the exemplary stainless-steel tube 940 provides a means to support and translate the delivery catheter, when nested inside the steerable guide handle.

FIG. 97 shows an image of a guide catheter prototype with transseptal curve 980 at segment 901. Transseptal curve 520 can range from −5 degrees to 180 degrees. This degree of curvature allows easy access past the septum to deliver the fixation device. In an alternate embodiment, the catheter in this invention is designed to be fully two-way steerable −180 to 180 or −270 to 270 or −359 to 359 degrees, for added functionality.

FIG. 98 shows an image of a catheter prototype, wherein the guide catheter has a two-way transseptal curve 980 at segment 901 and at segment 1010 has a 4-way mitral curves 985, 986, 987, 988. Mitral curves range from −90 to 90 or −180 to 180 or −270 to 270 or −359 to 359 degrees 983. Further, it has high strength to resist torsion and can be rotated 981 along it's longitudinal axis 983. The 4-way mitral curve with rotation allows easy access to the MV. The guide catheter and delivery catheter may optionally have preset curves.

FIG. 99 shows an image of an exemplary guide catheter prototype in an anatomical heart model.

Figure 100:
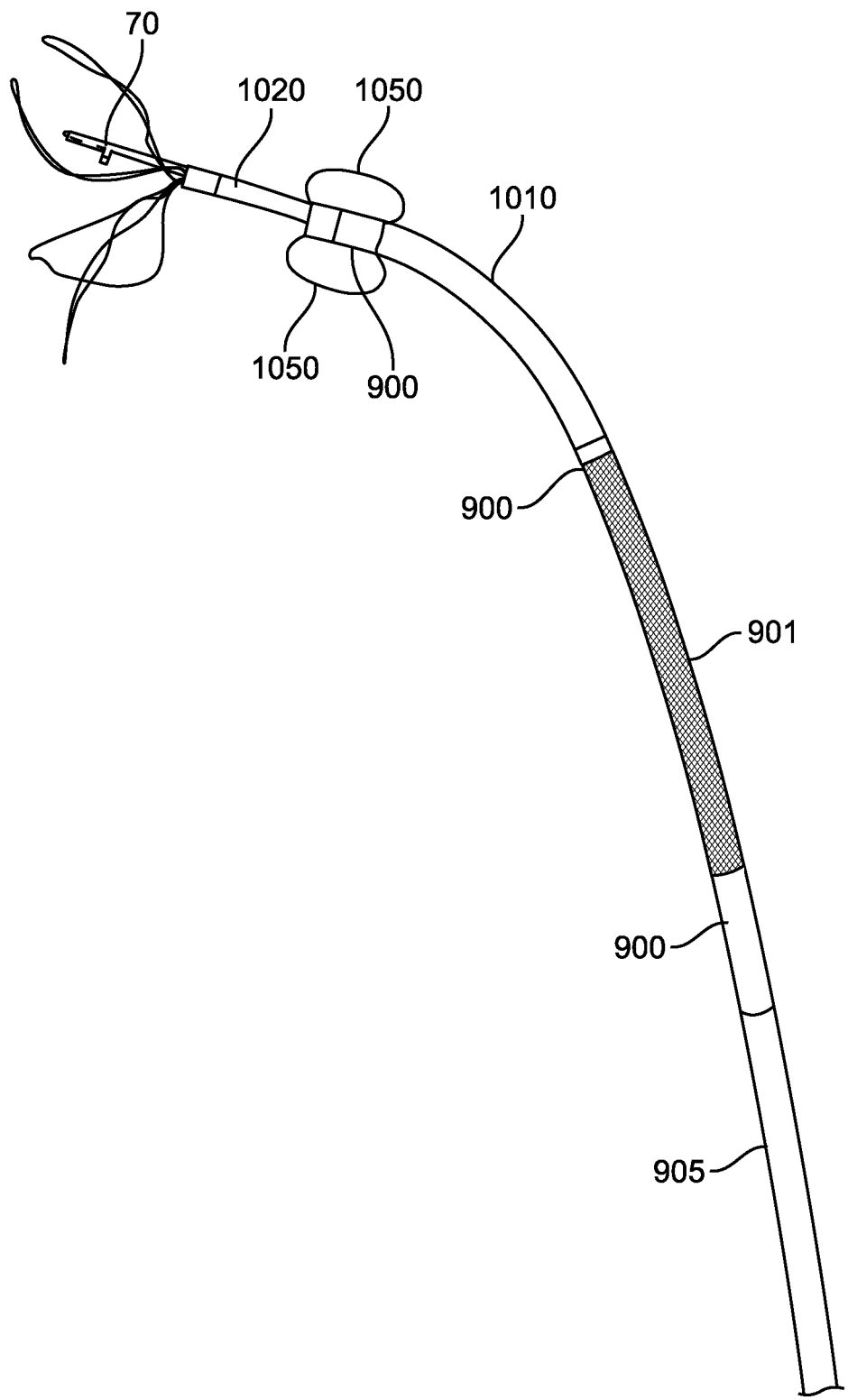
FIG. 100 is a photographic image of a delivery system prototype with a balloon-like feature on the guide catheter.

FIG. 100 shows an image of an exemplary delivery system prototype with an inflatable balloon-like feature 1050 on guide catheter. The balloon feature 1050 can function as a bumper to prevent trauma to the surrounding tissues as the delivery system is advanced or retracted in a vessel. Further, balloon feature 1050 can be inflated to stabilize the guide catheter to prevent unintentional movement (i.e. retraction, progression) of the delivery system. Balloon feature 1050 can be positioned any place along the guide and/or delivery catheter. In a preferred embodiment, the balloon is mounted distally at the tip and when inflated post septal crossing, helps prevent unintended retraction of the guide into the right atrium.

Figure 101:
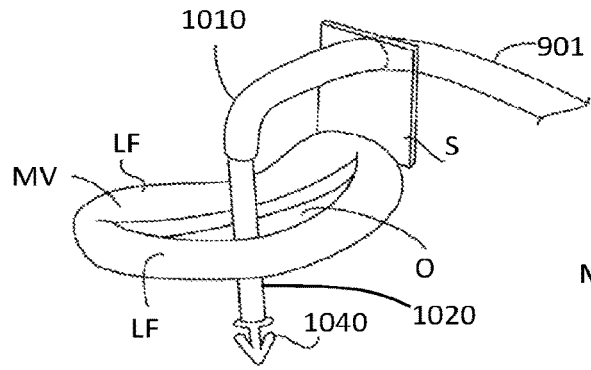
FIG. 101 illustrates the curvatures of a preferred two-nested catheter system as it is advanced past the mitral valve.

FIG. 101 illustrates the curvature of a preferred two-nested catheter system, as the delivery catheter 1020 is advanced past the MV. The mitral curve of distal guide shaft 1010 and septal curves proximal guide shaft 901 allows easier access to LF, as well as, advantageously positioning fixation device 1040 below MV. It also shows the straight unsupported segment of the delivery catheter 1020.

Figure 102:
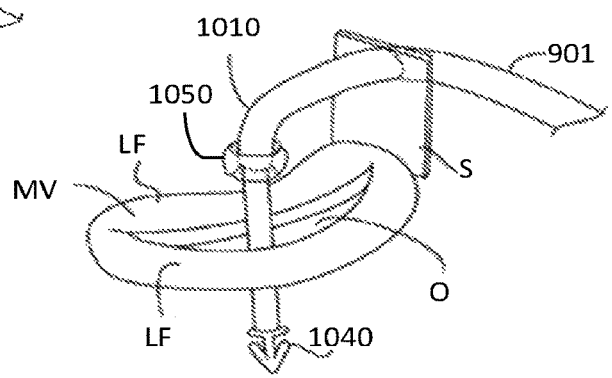
FIG. 102 shows the curvatures of the two-nested catheter system as in FIG. 101, with an addition of a balloon-like feature on the distal end of the guide catheter.

FIG. 102 illustrates the curvature of a preferred two-nested catheter system with addition of a balloon-like feature 1050 on the distal end of the guide catheter 1010, as the delivery catheter 1020 is advanced past the MV. Potential advantages of two-nested catheter system over three-nested catheter system are lower cost and lower profile.

Figure 103:
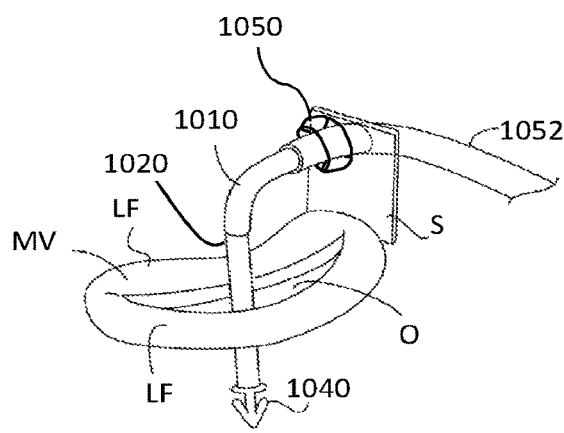
FIG. 103 illustrates the curvatures of a three-nested catheter system with a balloon-like feature at the tip of a guide catheter.

FIG. 103 shows the curvature of three-nested guide catheter 1020 with an addition of a balloon-like feature 1050 on the distal end of guide catheter 1052, as the delivery catheter 1020 is advanced past the MV. In this configuration, balloon 1050 stabilizes the distal end of the guide catheter 1052 and prevents accidental retraction across the septa S.

Figure 104A:
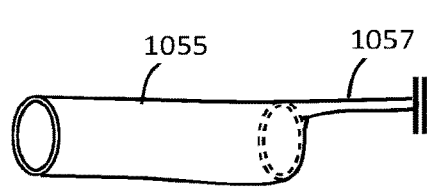
FIG. 104A illustrates an exemplary bailout guide catheter.

FIG. 104A shows bailout catheter guide 1055 with a long pull/push feature 1057. Feature 1057 controls bailout guide catheter 1055 to enclose/cover/shield the fixation device during retraction/bailout. In a preferred embodiment and method, the bailout catheter is situated external to the patient and not advanced inside the patient unless a bailout is desired. This is an advantage of this invention which mitigates the need and risk of insertion of large diameter bailout catheters in most cases. This advantage can be easily applied to typically large French sized three-nested catheter systems such as MitraClip® delivery system, by using a bailout catheter design as per this invention and adding steerability at trans-septal curves to steerable sleeve, and by using a distal balloon as a bumper or shield.

Figure 104B:
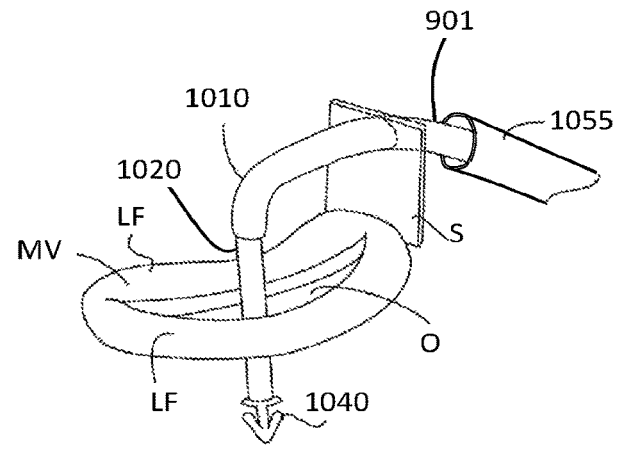
FIG. 104B shows the curvatures of the two-nested catheter system as in FIG. 101 with an addition of a bailout guide catheter.

FIG. 104B shows an exemplary two-nested catheter system as in FIG. 101, with addition of a bailout catheter guide 1055, optionally inserted close to septa S. Bailout catheter guide 1055 can be used to enclose/cover/shield the fixation device 1040 during retrieval in order to prevent trauma to the surrounding tissues as the delivery system is retracted from the patient after bailout. The bailout catheter 1055 may optionally comprise of balloon 1050.

Figure 105:
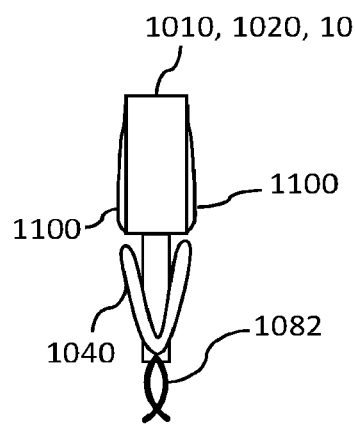
FIGS. 105-107 illustrate various embodiments of features that may be attached to the guide catheter and/or delivery catheter.
Figure 106:
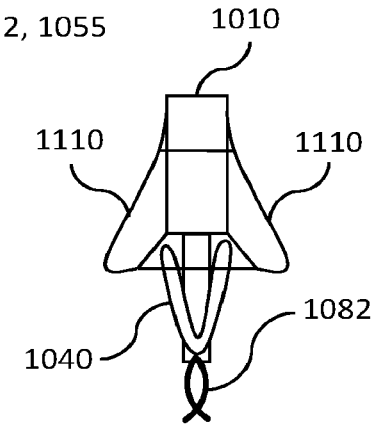

FIGS. 105-106 show umbrella-like feature 1110 at the tip of a guide catheter 1010, 1052 or delivery catheter 1020 or bailout catheter 1055. Umbrella feature 1110 functions as an enclosure device to surround fixation device 1040 as the delivery system is advanced and/or retracted during the procedure. Umbrella feature 1110 can be expanded/inflated to stabilize the delivery system during mitral valve repair surgery, thereby increasing efficiency.

Figure 107:
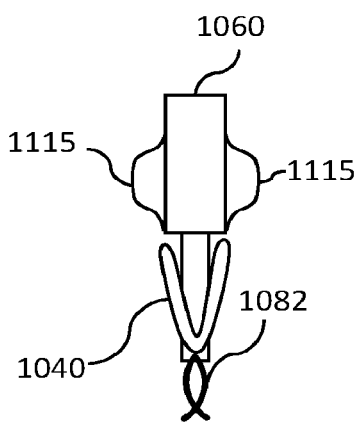

FIG. 107 shows inflatable bumper-like balloon feature 1115 that can optionally be part of a standalone attachment feature 1060 that can be mounted on to a catheter 1010, 1020, 1052, 1055. Bumper feature 1115 prevents fixation device 1040 or the delivery system from causing trauma to the lumen walls and/or blood vessels.

Figure 108:
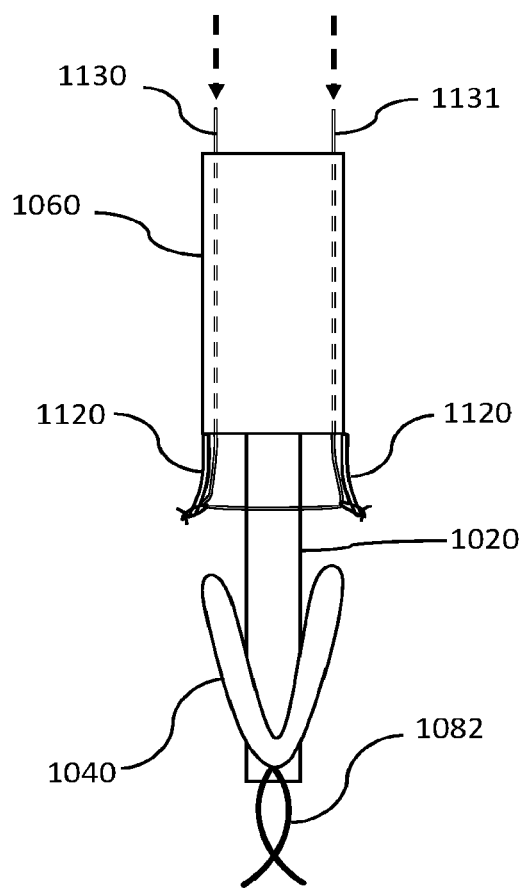
FIGS. 108-109 illustrate features that may be configured at the distal tip section of guide catheter and/or delivery catheter for shielding and/or retracting the fixation device.
Figure 109:
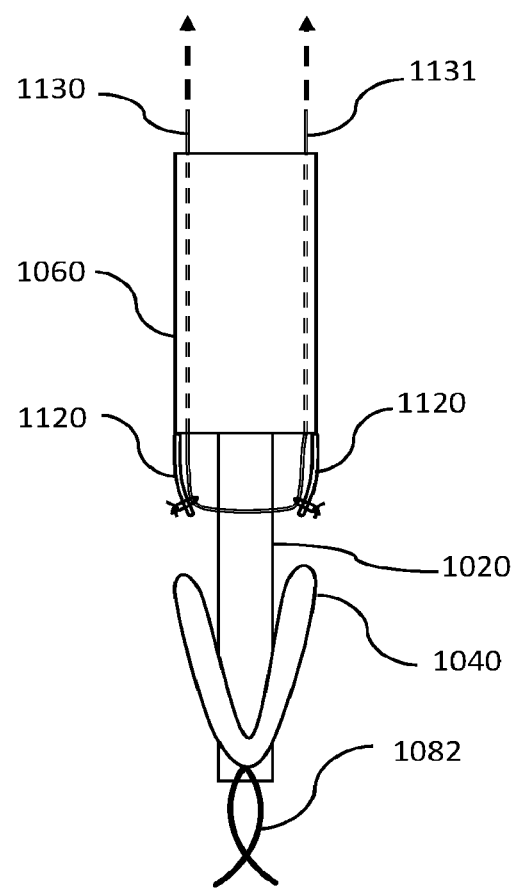

FIGS. 108-109 illustrate cross-section of a self-expanding bell/funnel shaped nested flat features 1120 (like flower petals) that may be attached to the guide catheter and/or delivery catheter to enclose/funnel the fixation device 1040 during the progression and/or retraction of the delivery system. The feature 1120 can be actuated using pullwires and/or sutures 1130, 1131, as indicated by the arrows, to collapse or expand.

Figure 110:
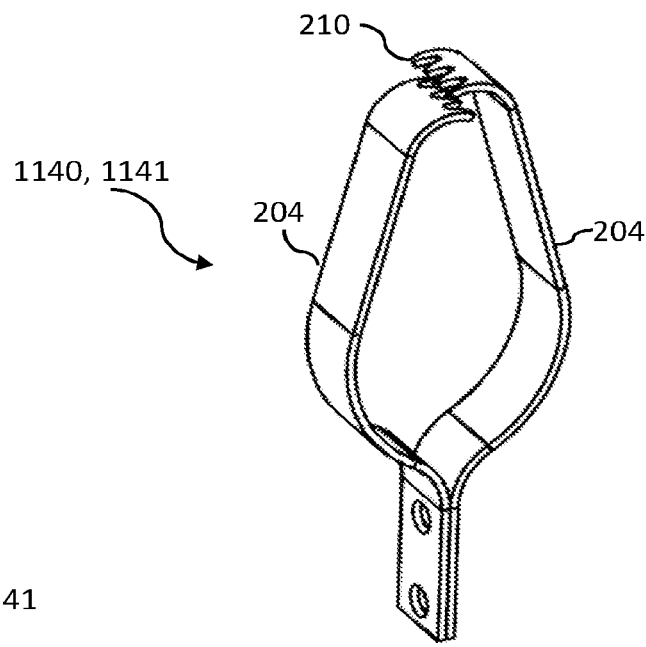
FIGS. 110 and 111 show two exemplary variations of a fixation device with claws at the tip of the arms.
Figure 111:
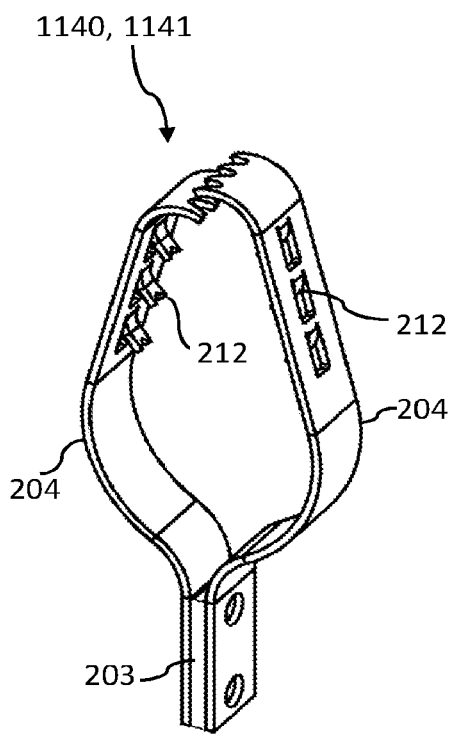

FIGS. 110 and 111 shows alternative embodiments of a tissue fixation device 1140, 1141 with a claw 210 on the proximal ends of each of the two outer arms 204. Claw 210 is used to increase surface area of the outer arms 204 in order to grasp more target tissue. The base 5 is not shown for simplicity.

Figure 112:
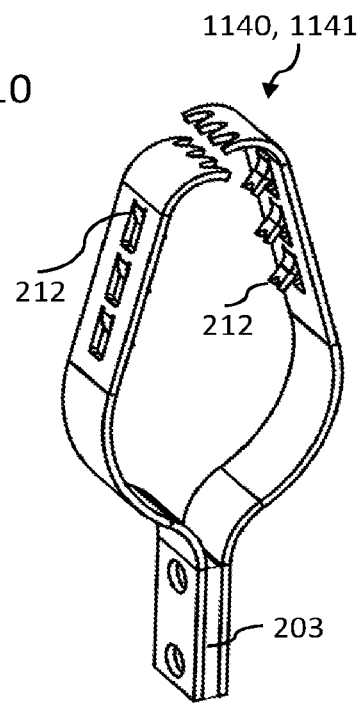
FIG. 112 shows an alternate embodiment of the fixation device shown in FIG. 111 with barbs on the interior of the arms.
Figures 113A, 113B:
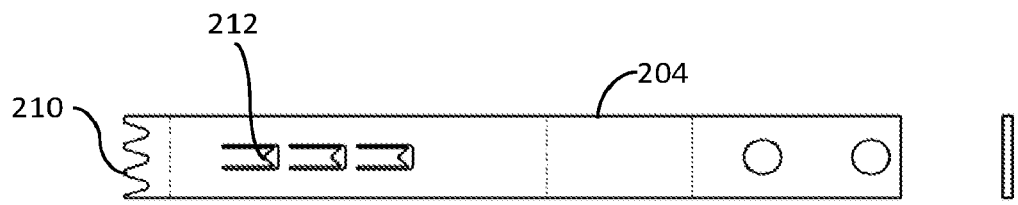
FIGS. 113A-113F shows alternative views including a flat-pattern of an exemplary fixation arm shown of the type shown FIG. 112.
Figures 113C, 113D, 113E, 113F:
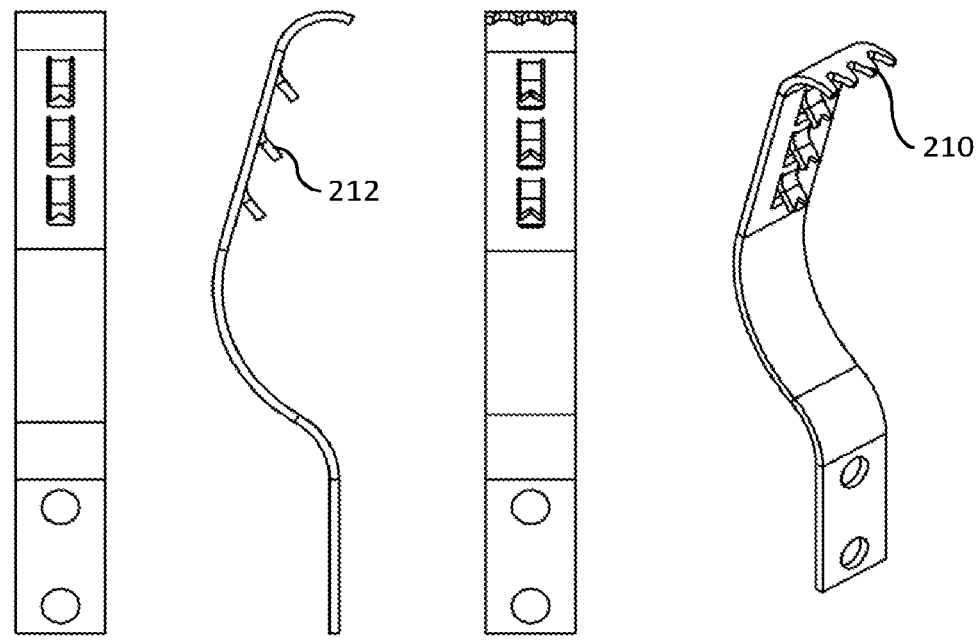

Further, FIG. 112 shows an alternative embodiment of the same tissue fixation device 1140, 1141 with the addition of barbs 212. The base 5 is not shown for simplicity.

FIGS. 113A-113F shows alternative views including a flat pattern illustration of the outer arms 204, detailing the preferred angles and positions of barbs 212 and claws 210.

Figure 114:
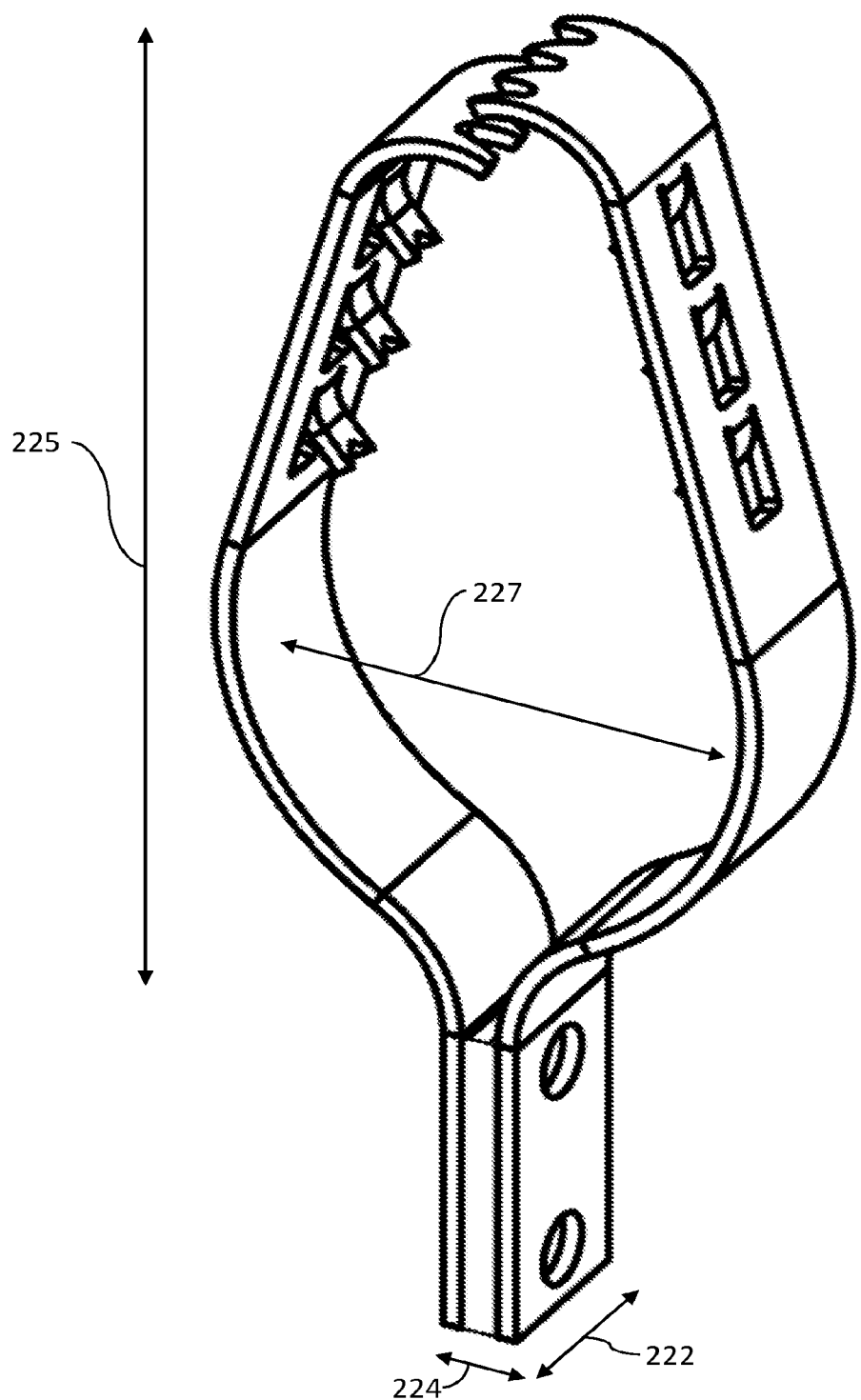
FIG. 114 illustrates the dimensions of a preferred embodiment of the fixation device.

FIG. 114 illustrates the functional length 225 of outer arms 204 and the functional width 227 of a tissue fixation device embodiment 1140, 1141. The thickness of the fixation device is modeled by length of device base 222 and width of device base 224. In a preferred embodiment, the functional length of arms 225 is manufactured to be >1.5× longer than functional width 227. As such, changing the functional length 225 and functional width 227 of the fixation device will vary the amount of tissue to grasp and/or force exerted and/or area of tissue engagement. Additionally, varying base length 222 and thickness of the arms 204 will improve and/or increase the amount of tissue grasping force.

Figure 12:
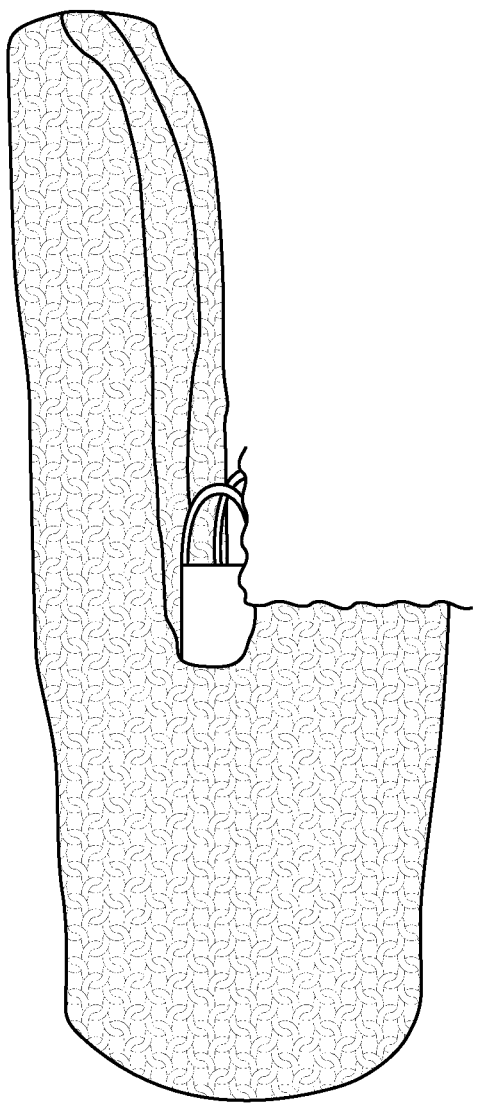
FIGS. 12-13 are photographic images of a prototype covered with polyester fabric.

Alternate embodiments/prototypes of the two-arm based tissue fixation devices 1140, 1141 can be seen in FIGS. 10-12.

In another exemplary and preferred embodiment, the two-arm fixation device 1140, 1141 may optionally comprise of an adjustable tether, as described in the 'SUMMARY OF THE INVENTION' section.

Figure 115:
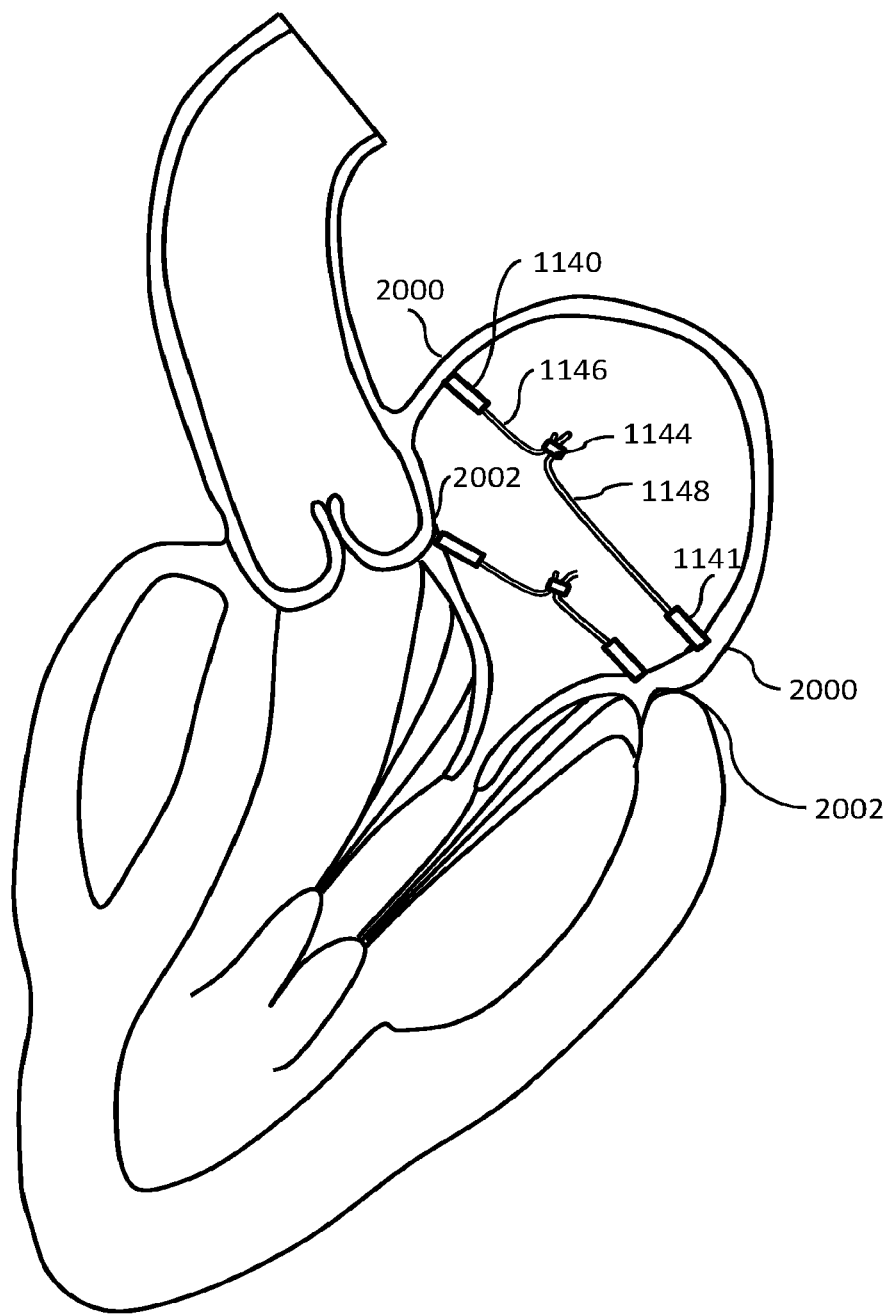
FIG. 115 illustrates tethered tissue grasping devices on the atrial side of the heart and on the mitral annulus.

FIG. 115 illustrates embodiments of the tethered tissue fixation devices used to coapt and/or cinch the target tissue closer. For example, tissue grasping device 1140 is coupled to tether 1146 while tissue grasping device 1141 is coupled to tether 1147. The tethers are cinched and affixed with connector 1144. Tethers 1146 and 1147 can be of metal wires and/or polymeric sutures. The tissue grasping devices can be positioned at locations 2000 or 2002. Location 2000 refers to the atrial wall of the heart and location 2002 refers to the mitral annulus. Structural and functional integrity of the heart is reinforced by cinching and/or coapting the valve annulus and/or strategic locations in the heart such as leaflet edges are some of the obvious advantages of this invention.

Figure 116:
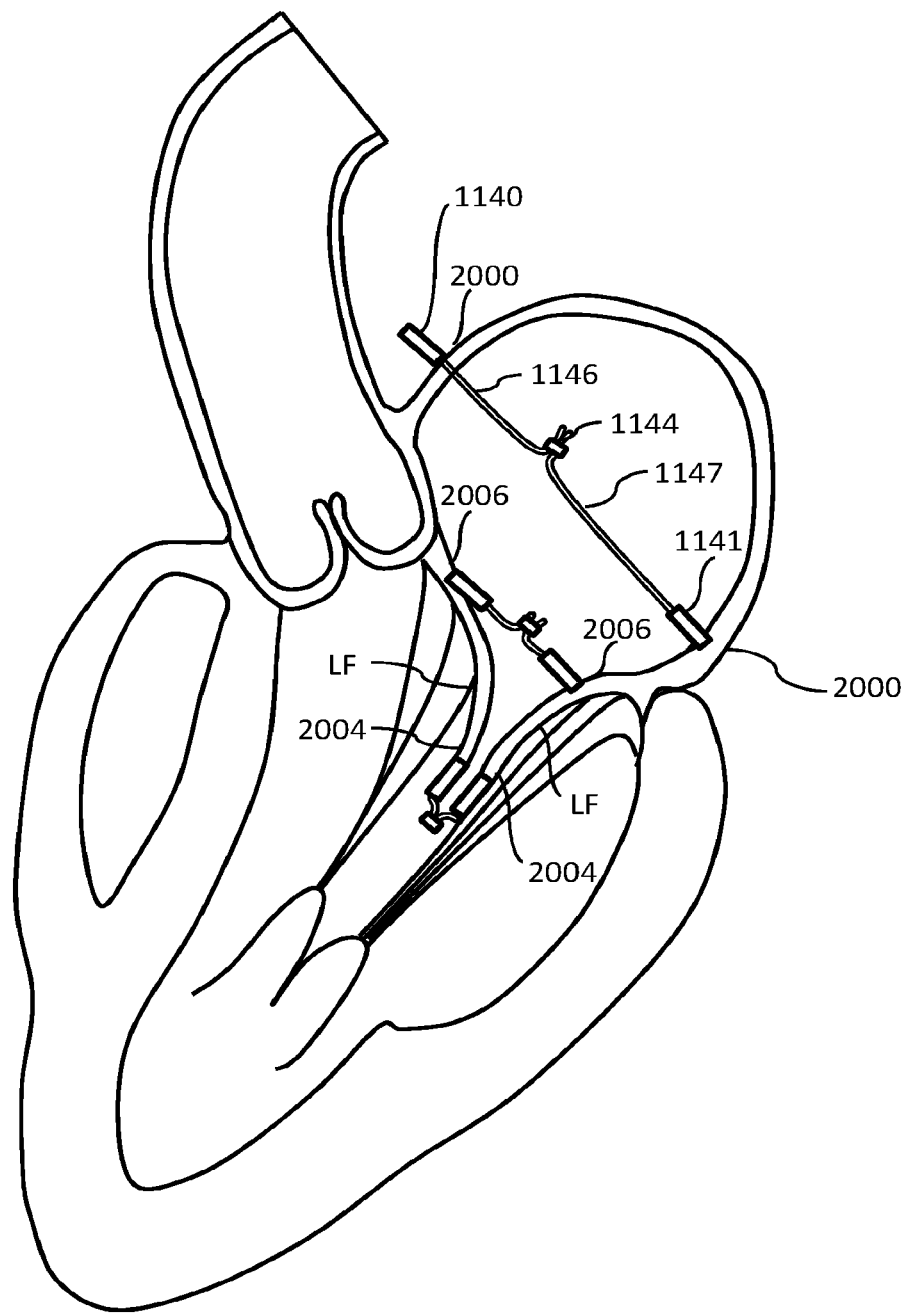
FIG. 116 illustrates tethered tissue grasping devices on the atrial side of the heart, mitral annulus, on the cusps of the leaflets and at the edges of the mitral valve.

FIG. 116 illustrates embodiments of the tethered tissue fixation devices at an exemplary and preferred location 2004, which is at the leaflet edge. Positioning the fixation device at location 2004 and coapting creates edge-to-edge Alfieri repair in a mitral valve to mitigate regurgitation. FIG. 116 additionally show other exemplary locations such as 2006, which is at the cusp of the leaflet.

Figure 117:
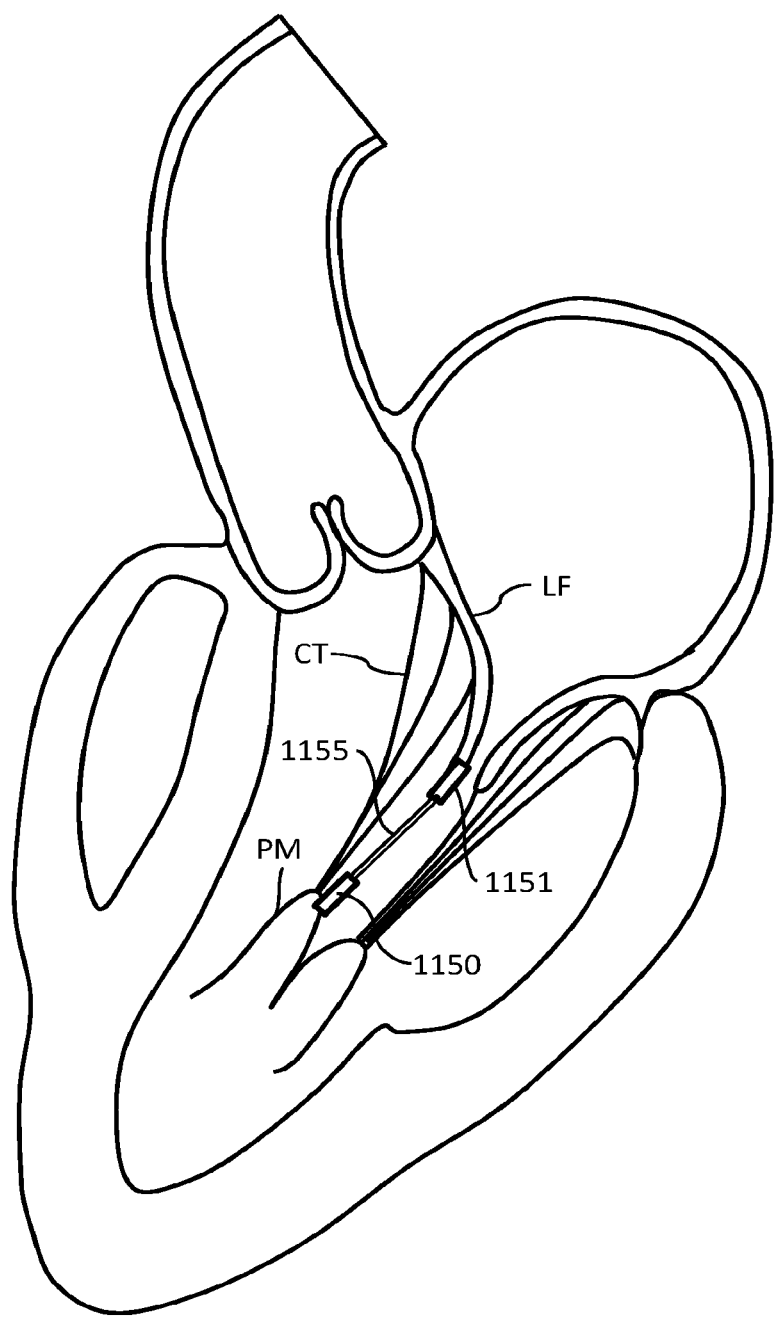
FIG. 117 illustrates tethered tissue grasping devices on a leaflet of the mitral valve and a papillary muscle of the left ventricle.
Figure 118A:
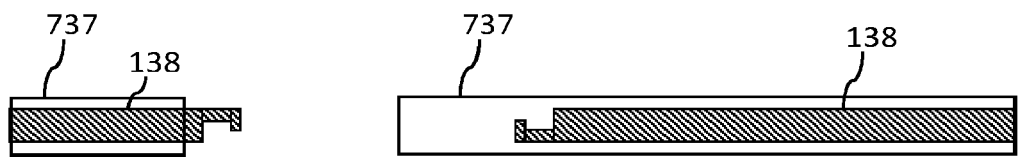
FIGS. 118A-118D show an actuation rod in a modular fashion that can be attached and/or detached within a catheter.
Figure 118B:
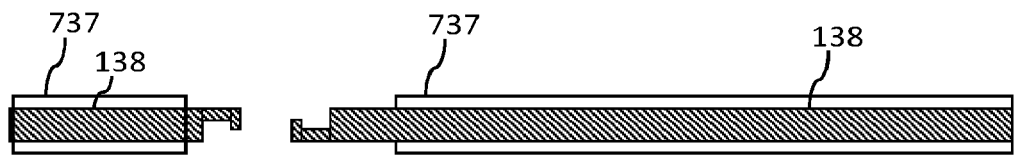
Figure 118C:
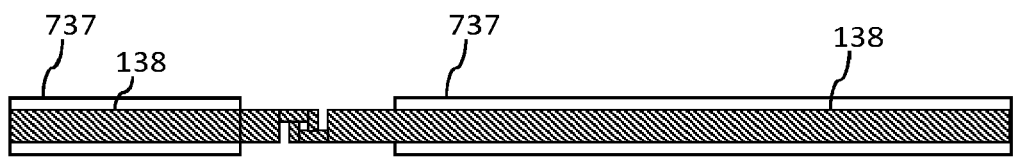
Figure 118D:
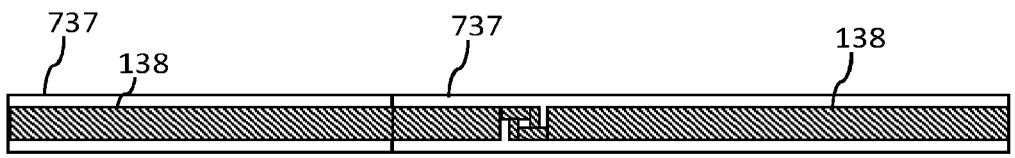

FIG. 117 illustrates an embodiment of a tethered tissue fixation devices 1150, 1151, wherein connector 1144 is not used. In this embodiment, fixation devices 1150 is coupled to fixation device 1151 via an adjustable tether 1155. Like tether 1146 and 1147, tether 1155 may be a metal wire or a suture. As can be seen in this figure, the fixation device embodiment 1150 is grasped on to the papillary muscle PM and embodiment 1151 is grasped on to the edge of a leaflet, thereby mimicking the functions of the chordae.

FIGS. 118A-118D show modular designs of the distal and proximal ends of actuation rod 138 in various unlocked (FIGS. 118A-118B) and locked (FIGS. 118C-118D) positions. This configuration allows easy removal and/or addition of actuation rod 138 within catheter 737 regarding surgical needs. Further, this modular design allows assembly and disassembly of the catheter system for easy and compact storage as cartridges.

Figures 119A, 119B, 119C:
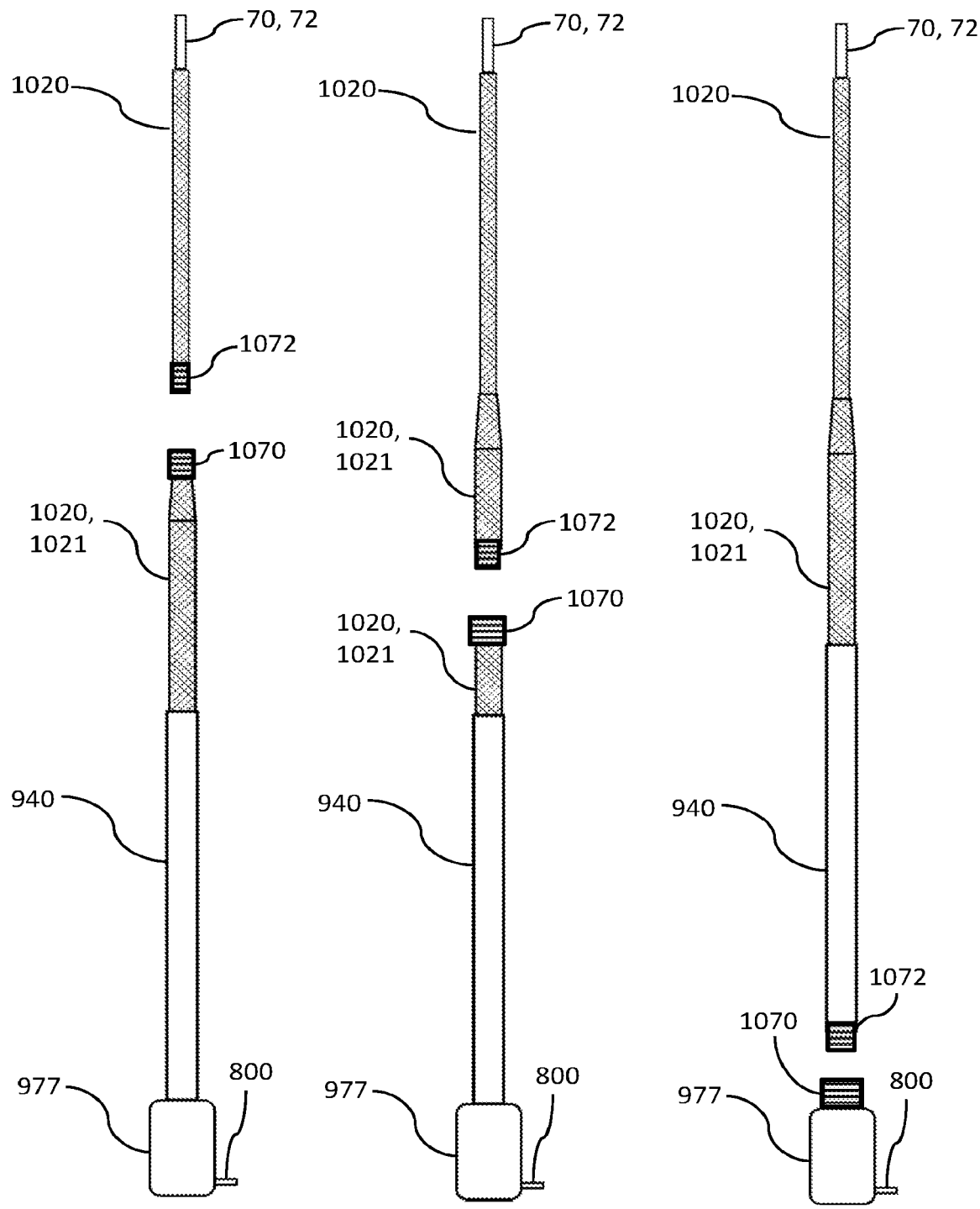
FIGS. 119A-119C show alternative embodiments of a modular catheter system.

FIG. 119A shows an alternative embodiment of a catheter with a modular configuration, wherein distal shaft of delivery catheter 1020 comprises of male connector 1072 at the proximal end. Male connector 1072 may be inserted into female connector 1070 configured at the distal end of distal shaft of delivery catheter 1020 or proximal shaft of delivery catheter 1021 to assemble or disassemble the catheter system for easy use and storage as cartridges. Further, the connectors may be positioned anywhere along a catheter system such that alternative configurations of catheter shafts or catheter system may be produced, as shown in FIG. 119B-119C

FIGS. 120A-120E show images of the prototype during bench testing of a retrieval system, wherein the fixation device comprises of retrieval sutures 1170, 1172 for the retrieval system to grasp and raise and/or lower the inner and outer arms.

Figure 120A:
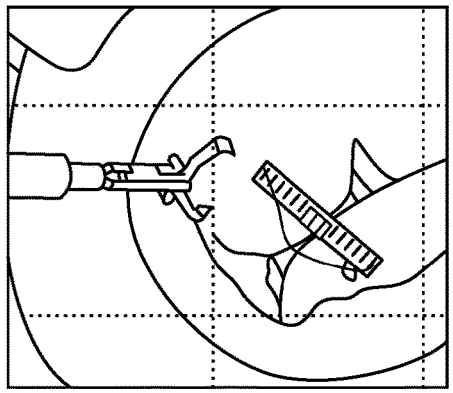
FIGS. 120A-120E show images of a retrieval system prototype using sutures.
Figure 120B:
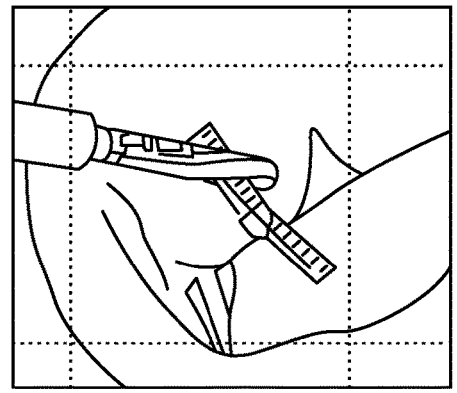
Figure 120C:
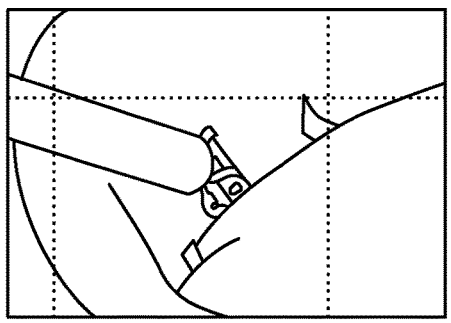
Figure 120D:
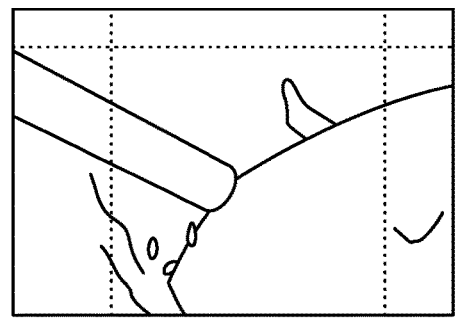
Figure 120E:
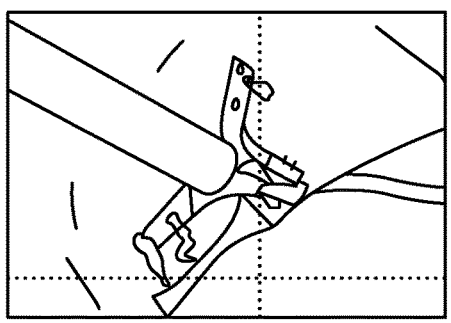
Figure 120F:
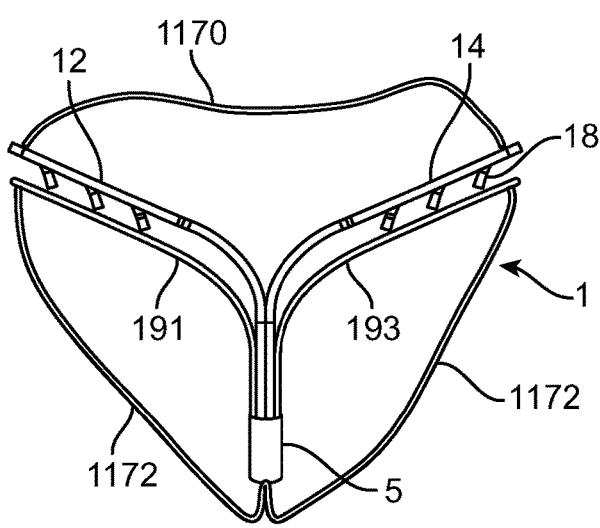
FIG. 120F show an alternative embodiment of the fixation device comprising of sutures utilized during retrieval.

FIG. 120F shows the schematic of an alternative embodiment of the fixation system comprising of inner arms 12 and 14 and outer arms 191 and 193. Retrieval sutures 1170, 1172 are connected to the inner and outer arms for the retrieval system of FIGS. 120A-120E to grasp in order to raise and/or lower the arms.

Anchoring of Release Rod:

The referenced application PCT/US2017/042003 describes Release rod. One or more distal portions of Release rod may comprise one or more anchoring portions that reduces the risk of inadvertent release of release rod from a delivery system. Examples of anchoring portions include, but are not limited to: bends, curves, expanded regions, wider regions, deployable elements, etc.

Guide and Delivery Catheter:

The referenced PCT describes two-catheter system to perform transcatheter percutaneous deployment. In a preferred embodiment, all the curves achieved using three-catheter system (for example as described in U.S. Pat. No. 7,226,467B2) is configured to be achieved using two catheter system. That is, the individual curves of Guide and Sleeve as described in U.S. Pat. No. 7,226,467B2, will be incorporated into a single steerable guide using common catheter manufacturing techniques.

The catheter is typically steered using pull wires or pull-push lumens while advancing or retracting. Hence, using common and typical electromechanical interface such as linear rollers, linear actuators, electro-pneumatic pistons, motors, a robotic interface can be created to duplicate human manipulations. Similarly, delivery catheter can be controlled. Current technology such as those used in robotic surgery is much more advanced and intricate than the movements and manipulations used in a percutaneous transcatheter based structural heart devices. Thus, remote or robotic control of catheter can be performed.

Additionally, in a preferred embodiment, the catheter can be configured to incorporate pressure sensing and dye infusing features. This can be done via: a) main lumen of the catheter shaft, b) a port or grove and or tubular lumen along the ID, OD, or in the wall of the steerable guide (and or delivery) catheter shaft and c) using thin film or spot pressure sensors at various strategic locations of the catheter shaft.

One or more guide catheters and delivery catheters disclosed herein may comprise one or more lumens that can act to accommodate one or more additional elements including, but not limited to: sensors (e.g. pressure sensors, flow sensors, optical sensors, ultrasound sensors, vibration sensors, doppler sensors, force sensors, etc.), one or more elements of Swan Ganz type catheters, OCT elements, gyroscopes, accelerometers, etc. In another embodiment, one or more sensors or elements disclosed herein may be inbuilt or embedded into one or more portions of the devices disclosed herein.

Sensors and actuators that may be used in relation to this invention, to improve the safety, ease of use, and efficacy of the delivery system and fixation device. Sensors and actuators may be used to assist and evaluate device delivery (acute) and efficacy (acute or chronic). Sensors and actuators maybe active or passive, removable or implantable and may provide acute or chronic physiological or non-physiological data to assess or evaluate patient health. Sensors and actuators maybe active or passive, removable or implantable and provide acute or chronic physiological or non-physiological data to access or evaluate implant integrity and or function. Sensors may be used for visualization: thermal, optical, ultrasonic (including ICE), OCT, fluoroscopic Sensors and actuators maybe electrical, mechanical, magnetic, RF, chemical or combination. Sensors and actuators may be wired or wireless and may communicate with mobile or fixed external interface. The catheters of the present invention may be used as a conduit for external sensors, for example pressure sensor replacing Swan-Ganz catheter. The term sensor, electrode, transducer, IC, circuit, chip and actuator may be used interchangeably. Sensors and actuators listed are for examples only. Any suitable metal or polymer or ceramic, organic or inorganic, flexible or rigid, matrix or material and their combinations may be used to produce the desired sensors and actuators. Further, motors may be used to steer the catheters and deploy the device. For example, motors may be used instead of manual knobs or levers to pull or push on the actuation sutures or steerable catheter pullwires or other common mechanisms.

All implant embodiments described in this invention may be optionally covered, wrapped, coated, or the like to improve biocompatibility and tissue interface. Suitable coverings can be fabric, web, fibrous, braid, woven or nonwoven. The coatings can be metallic, ceramic, polymeric, or combinations thereof. Suitable metallic coatings include titanium, TiN, tantalum, gold, platinum, and alloys thereof. Suitable ceramic and inorganic coatings include titanium dioxide, hydroxyapatite, CaP, and the like. Suitable polymeric coatings include fluoropolymers, e.g. PTFE, PFA, FEP, ECTFE, ETFE; parylene, polyester, PET, polypropylene, polyurethane, PEEK, PVDF, HDPE, LDPE, UHMWPE, phosphorylcholine, THV, and the like. Suitable biodegradable include poly(lactic acid), poly(glycolic acid), polydioxanone, poly(ε-caprolactone), polyanhydride, poly (ortho ester), copoly(ether-ester), polyamide, polylactone, poly(propylene fumarate), and their combinations. Such metallic, ceramic and/or polymeric coatings are listed as examples only. Any suitable metal, ceramic, polymer, and combination thereof may be used to produce a desirable coating.

In one particular exemplary embodiment of a medical method, a user assesses the regurgitation of valve leaflets through one or more medical imaging methods including, but not limited to fluoroscopy and ultrasound. Based on the assessment of coaptation depth, profile, disease and or size of the leaflets, one or more sizes of straight or curved or a combination shape device is implanted. The advantage of deploying a selected shape and size of implant is to improve efficacy, safety and minimize the number of device implants.

Any of the implant arms disclosed herein may comprise one or more telescoping elements.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present, or problems be solved.

Although the operations of some of the disclosed methods are described in a particular order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified elements. That is, if two of a particular elements are present, one of these elements is also present and thus "an" element is present. The terms "a plurality of" and "plural" mean two or more of the specified elements.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

The following is a listing of the reference numbers used in this application:
1 Exemplary embodiment of the fixation device
5 Base bracket
12 Flat-pattern of Inner arm, exemplary embodiment of a straight fixation device used to capture leaflet.
13 Flat pattern of Outer arm, exemplary embodiment of a straight fixation device used to capture leaflet.
14 Inner arm, exemplary embodiment of a fixation device used to capture leaflet.
15 Outer arm, exemplary embodiment of a fixation device used to capture leaflet.
18 Atraumatic barb-like frictional element of inner arm
20 Feature of inner arm 12 allowing the coupling to the base 5
21 Feature of inner arm 12 allowing the coupling to the base 5
24 Feature of inner arm 12 allowing sutures to loop through and manipulate the arms of the fixation device
25 Feature of inner arm 12 allowing sutures to loop through and manipulate the arms of the fixation device
26 Slot feature of inner arm 12 under barb 18

32 Feature of outer arm 14 allowing the coupling to the base 5
34 Feature of outer arm 14 allowing the coupling to the base 5
37 Slot feature of outer arm 14
38 Feature of outer arm 14 allowing sutures to loop through and manipulate the arms of the fixation device
39 Feature of outer arm 14 allowing sutures to loop through and manipulate the arms of the fixation device
40 Feature of outer arm 14 allowing sutures to loop through and manipulate the arms of the fixation device
46 Feature of outer arm 14 allowing sutures to loop through and manipulate the arms of the fixation device
50 Left bracket of base bracket 5
52 Right bracket of base bracket 5
56 Coupling feature of base bracket 5
60 Feature of bracket 50 allowing passage of screw
61 Feature of bracket 52 allowing passage of screw
62 Feature of bracket 50 allowing passage of screw
63 Feature of bracket 52 allowing passage of screw
65 Hole to pass release rod.
70 Release bar, the distal most component of the delivery catheter that interfaces with the fixation device.
72 Release bar, the distal most component of the delivery catheter that interfaces with the fixation device.
80 Feature of release bars 70, 72 allowing sutures to loop through and manipulate the arms of the fixation device.
81 Feature of release bars 70, 72 allowing for passage of sutures
82 Feature of release bars 70, 72 allowing for passage of sutures
83 Feature of release bars 70, 72 allowing for passage of sutures
84 Feature of release bars 70, 72 allowing for passage of sutures
85 Feature of release bars 70, 72 allowing for passage of sutures
86 Feature of release bars 70, 72 allowing for passage of sutures
87 Feature of release bars 70, 72 allowing for passage of sutures
88 Feature of release bars 70, 72 allowing for passage of sutures
95 Hinge component coupled to inverters 101 and 102
101 Right inverter
102 Left inverter
110 Feature of inverter 117 anchoring the inverter to release bars 70, 72
111 Feature of inverter 101 allowing suture to loop through and allow manipulation of the arms
112 Feature of inverter 102 allowing suture to loop through and allow manipulation of the arms
116 Embodiment of left inverter with stopper 142
117 Embodiment of right inverter with stopper 142
120 Manipulation of inner arms
121 Manipulation of inner arms
125 Segment of suture 131
126 Segment of suture 130
127 Segment of suture 131
128 Segment of suture 130
130 Suture allowing control of inner arm 12 or 14
131 Suture allowing control of inner arm 12 or 14
136 Manipulation of suture 130; straightens inner arm 12
138 Actuation rod with distal suture loop
139 Structural actuation tube with distal suture loop and proximal suture ends
142 Stop feature of inverters 116 and 117 to prevent the inverters from flipping to wrong side
150 Feature of release bars 70, 72 allowing passage of sutures, wires, plastic tube and/or metal tube
152 Feature of release bars 70, 72 allowing passage of release rod 160
160 Release rod that anchors fixation device to release bars 70, 72
174 Segment of suture 180
175 Segment of suture 181
176 Segment of suture 180
177 Segment of suture 181
178 Segment of suture 180
179 Segment of suture 181
180 Suture allowing control of outer arm 13 or 15
181 Suture allowing control of outer arm 13 or 15
191 Outer arm, exemplary embodiment of a fixation device used to capture leaflet
193 Outer arm, exemplary embodiment of a fixation device used to capture leaflet
192 Inner arm, exemplary embodiment of a fixation device used to capture leaflet
194 Inner arm, exemplary embodiment of a fixation device used to capture leaflet
195 Outer arm, exemplary embodiment of a fixation device used to capture leaflet
197 Outer arm, exemplary embodiment of a fixation device used to capture leaflet
204 Tissue grasping arm
210 Claw feature of tissue grasping arm 204
212 Barb feature of tissue grasping arm 204
222 Length of base of fixation device embodiment
224 Width of base of fixation device embodiment
225 Functional length of tissue grasping arm 204
227 Functional width of tissue grasping device
250 Band-like feature of inner arm 192 affixing wire loops together
252 Small wire loops within an arm made of wires, to pass actuating sutures through.
280 Suture loop allowing the passage of sutures to control the outer arms
281 Suture loop allowing the passage of sutures to control the outer arms
282 Suture loop allowing the passage of sutures to control the outer arms
283 Suture loop allowing the passage of sutures to control the inner arms
330 Actuation-rod of a handle, allowing manipulation of the outer arm
331 Actuation-rod of a handle, allowing manipulation of the inner arm
332 Actuation-rod of a handle, allowing manipulation of the inner arm
333 Actuation-rod of a handle, allowing manipulation of the outer arm
350 Exemplary embodiment of a custom handle for outer and inner arms manipulation
360 Short delivery shaft
372 Release knob of handle 350 allowing control of release rod 160
382 Opening of handle 350 for delivery shaft
400 Feature of handle for tightening screws to control 350
422 Set screw feature of handle 350 for fastening deliver shaft
462 Feature of handle 350 to manipulate arms
463 Feature of handle 350 to manipulate arms
464 Feature of handle 350 to manipulate arms 465 Feature of handle 350 to manipulate arms
466 Feature of handle 350 to flush line or sensor line or to manipulate arms
467 Feature of handle 350 to flush line or sensor line or to manipulate arms
468 Feature of handle 350 allowing coupling of release knob 372
500 Proximal threaded feature of handle 350 allowing control and manipulation of release knob 372
502 Distal threaded feature of handle 350 allowing control and manipulation of release knob 372
600 Bailout suture segment of curved fixation device
602 Bailout suture segment of curved fixation device
609 Bailout suture segment of curved fixation device
622 Suture loop allowing passage of suture 600
650 Embodiment of a curved fixation device
675 Manipulation of release rod 160
677 Manipulation of suture 602
681 Manipulation of release bar 72
700 Single lumen braided shaft
705 Multilumen braided shaft
725 Braid
727 Inner lumen of braided shaft
730 Peripheral lumen for guidewire, release rod and/or sutures
732 Single lumen shaft
734 Floating lumen to pass through guidewires, sutures, plastic tubes and/or metal tubes
736 Lumen of multi-lumen catheter allowing the passage of wires, sutures, plastic tubes and/or metal tubes
737 Lumen of multi-lumen catheter allowing the passage of wires, sutures, plastic tubes and/or metal tubes
739 Lumen of multi-lumen catheter allowing the passage of wires, sutures, plastic tubes and/or metal tubes
740 PEEK tubing/torque cable
800 Feature of catheter handle
850 Distal tip of guide catheter
900 Radiopaque marker(s) of steerable guide catheter
901 Intermediate steerable guide shaft section allowing stiffness transition for two-way and/or 4-way steering
905 Proximal shaft of steerable guide catheter
940 Stainless steel sheath to support delivery catheter
950 Stainless steel sheath to support steerable guide handle
975 Exemplary embodiment of a custom steerable guide catheter handle
977 Exemplary embodiment of a custom delivery catheter handle
980 Manipulation of the guide catheter
981 Manipulation of the guide catheter
982 Manipulation of the guide catheter
985 Manipulation of the delivery catheter
986 Manipulation of the delivery catheter
987 Manipulation of the delivery catheter
988 Manipulation of the delivery catheter
1000 Shaft of guide catheter
1010 Distal steerable guide shaft section allowing stiffness transition for two-way and/or 4-way steering
1020 Distal shaft of the delivery catheter that is potentially unsupported as it extends out of the guide catheter
1021 Proximal shaft of delivery catheter
1040 Exemplary embodiment of fixation device
1050 Balloon-like feature of feature 1060 stabilizing delivery catheter 1020 during procedure
1052 Third steerable guide catheter
1055 Bailout guide catheter
1057 Push-pull feature of bailout guide catheter 1055
1060 Feature that may be attached to guide catheter 1000 or delivery catheter 1020
1082 Suture loop
1100 Umbrella-like feature of feature 1060
1110 Umbrella-like feature of feature 1060
1115 Bumper-like feature of feature 1060
1120 Bell shaped nested flats
1130 Suture allowing manipulation of feature 1120
1131 Suture allowing manipulation of feature 1120
1140 Tissue grasping device
1141 Tissue grasping device
1144 Connector base
1146 Tether connecting tissue grasping arm 1040 to base 1044
1147 Tether connecting tissue grasping arm 1041 to base 1044
1150 Tissue grasping device with a tether
1151 Tissue grasping device with a tether
1155 Tether connecting tissue grasping arm 1150 to tissue grasping arm 1151
2000 Location of tissue grasping device at atrial wall
2002 Location of tissue grasping device at mitral annulus
2004 Location of tissue grasping device at leaflet edge of mitral valve
2006 Location of tissue grasping device at the cusp of the mitral valve leaflet
LF Leaflet of mitral valve
PM Papillary muscle of the left ventricle Although many embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. An endovascular heart valve repair system comprising:
a delivery catheter having a distal end configured to be introduced into a heart chamber adjacent to a pair of coapting heart valve leaflets, said delivery catheter including a release bar having a pair of inverters;
a valve repair leaflet grasping device comprising a hub configured to be removably attached to the release bar of the delivery catheter, a first pair of leaflet capture arms comprising a first inner arm and a first outer arm coupled to the hub, and a second pair of leaflet capture arms comprising a second inner arm and a second outer arm coupled to the hub; and a first set of control tethers positioned on or through the delivery catheter and having distal portions coupled to the outer arms and configured to selectively bias the outer arms into a valve leaflet capture position; and a second set of control tethers positioned on or through the delivery catheter and coupled to the inner arms and configured to selectively bias the inner arms into a valve leaflet capture position;

wherein the first set of control tethers are threaded through laterally spaced-apart locations on the inverters so that drawing each of the proximal portions of the of the first set of control tethers in a proximal direction causes the distal portions of each of the first set of control tethers to move in a distal direction to pull outer segments of each of the outer arms in a distal direction into the valve leaflet capture position.

2. An endovascular heart valve repair device as in claim 1, wherein drawing proximal portions of the of the second set of control tethers in a proximal direction causes distal portions of second set of control tethers to pull outer segments of the inner arms in a proximal direction into the valve leaflet capture position.

3. An endovascular heart valve repair device as in claim 1, wherein the pair of inverters comprises a first inverter extending laterally in a first direction from a distal tip of the delivery catheter and a second inverter extending laterally in a second direction from a distal tip of the delivery catheter.

4. An endovascular heart valve repair device as in claim 3, wherein the first and second directions are opposite to each other.

5. An endovascular heart valve repair device as in claim 4, wherein each of the first and second inverters is pivotally attached to the distal tip of the delivery catheter.

6. An endovascular heart valve repair device as in claim 5, wherein the pivotal attachment is configured so that the inverters laterally deploy when the first tethers are pulled proximally to apply an opening force to the inverters but are able to axially collapse in alignment with the delivery catheter in the absence of the opening force.

7. An endovascular heart valve repair device as in claim 6, wherein the first set of tethers pass from a distal end of the release bar, are slidably coupled to each of the inverters and the outer arms, and are fixedly attached to the release bar.

8. An endovascular heart valve repair device as in claim 7, wherein the second set of tethers pass from a distal end of the delivery catheter, are slidably coupled to each of the inner arms, and are fixedly attached to the release bar.

9. An endovascular heart valve repair device as in claim 6, wherein the first set of tethers pass from a distal end of the release bar, are slidably coupled to each of the inverters and the outer arms, and are removably attached to the release bar.

10. An endovascular heart valve repair device as in claim 1, wherein the inner and outer arms comprise inner and outer leaf springs.

11. An endovascular heart valve repair device as in claim 1, wherein the inner leaf springs are biased to open laterally outwardly away from the release bar and the outer leaf springs are biased to close laterally inwardly toward the release bar so that the leaflets may be captures therebetween when the leaf springs are unbiased.

12. An endovascular heart valve repair device as in claim 11, wherein the outward opening bias of the inner leaf springs is less than inward closing bias of the outer leaf springs.

13. An endovascular heart valve repair device as in claim 11, wherein the outer leaf springs are generally straight and lie closely over the release bar when unbiased so that the outer leaf springs will laterally close the inner leaf springs when all leaf springs are free from bias.

14. An endovascular heart valve repair device as in claim 1, wherein the distal portions of the first set of control tethers are attached to the free ends of the outer arms by suture loops.

15. An endovascular heart valve repair system comprising:

a delivery catheter having a distal tip configured to be introduced into a heart chamber adjacent to a pair of coapting heart valve leaflets, said delivery catheter including a release bar having a pair of inverters, wherein the pair of inverters comprises a first inverter extending laterally in a first direction from the distal end of the delivery catheter and a second inverter extending laterally in a second direction from the distal end of the delivery catheter, wherein the first and second directions are opposite to each other;

a valve repair leaflet grasping device comprising a hub configured to be removably attached to the release bar of the delivery catheter, a first pair of leaflet capture arms comprising a first inner arm and a first outer arm coupled to the hub, and a second pair of leaflet capture arms comprising a second inner arm and a second outer arm coupled to the hub; and a first set of control tethers positioned on or through the delivery catheter and coupled to the outer arms and configured to selectively bias the outer arms into a valve leaflet capture position; and a second set of control tethers positioned on or through the delivery catheter and coupled to the inner arms and configured to selectively bias the inner arms into a valve leaflet capture position;

wherein the first set of control tethers are threaded through laterally spaced-apart locations on the inverters so that drawing proximal portions of the of the first set of control tethers in a proximal direction causes distal portions of first set of control tethers to move in a distal direction to pull outer segments of the outer arms in a distal direction into the valve leaflet capture position.

16. An endovascular heart valve repair device as in claim 15, wherein each of the first and second inverters is pivotally attached to the distal tip of the delivery catheter.

17. An endovascular heart valve repair device as in claim 16, wherein the pivotal attachment is configured so that the inverters laterally deploy when the first tethers are pulled proximally to apply an opening force to the inverters but are able to axially collapse in alignment with the delivery catheter in the absence of the opening force.

18. An endovascular heart valve repair device as in claim 17, wherein the first set of tethers pass from a distal end of the release bar, are slidably coupled to each of the inverters and the outer arms, and are fixedly attached to the release bar.

19. An endovascular heart valve repair device as in claim 18, wherein the second set of tethers pass from a distal end of the delivery catheter, are slidably coupled to each of the inner arms, and are fixedly attached to the release bar.

20. An endovascular heart valve repair device as in claim 17, wherein the first set of tethers pass from a distal end of the release bar, are slidably coupled to each of the inverters and the outer arms, and are removably attached to the release bar.

* * * * *